(12) United States Patent
Guelcher et al.

(10) Patent No.: US 9,801,946 B2
(45) Date of Patent: *Oct. 31, 2017

(54) SYNTHETIC POLYURETHANE COMPOSITE

(71) Applicant: Vanderbilt University, Nashville, TN (US)

(72) Inventors: Scott A. Guelcher, Thompson Station, TN (US); Jerald Dumas, Nashville, TN (US); Edna M. Prieto, Nashville, TN (US); Anne Talley, Nashville, TN (US); Andrew Harmata, Nashville, TN (US); Katarzyna Zienkiewicz, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 130 days.

This patent is subject to a terminal disclaimer.

(21) Appl. No.: 13/868,077

(22) Filed: Apr. 22, 2013

(65) Prior Publication Data
US 2013/0236513 A1 Sep. 12, 2013

Related U.S. Application Data

(63) Continuation-in-part of application No. PCT/US2011/057551, filed on Oct. 24, 2011, which
(Continued)

(51) Int. Cl.
*A61K 47/46* (2006.01)
*A61K 47/02* (2006.01)
*A61K 38/18* (2006.01)

(52) U.S. Cl.
CPC ............ *A61K 47/46* (2013.01); *A61K 38/18* (2013.01); *A61K 38/1875* (2013.01); *A61K 47/02* (2013.01)

(58) Field of Classification Search
None
See application file for complete search history.

(56) References Cited

U.S. PATENT DOCUMENTS

| 4,743,259 A | 5/1988 | Bolander et al. |
|---|---|---|
| 4,880,610 A | 11/1989 | Constantz |

(Continued)

FOREIGN PATENT DOCUMENTS

| WO | 1998019718 | 5/1998 |
|---|---|---|
| WO | 2004009227 | 1/2004 |

(Continued)

OTHER PUBLICATIONS

Adhikari et al., Biodegradable injectable polyurethanes: Synthesis and evaluation for orthopaedic applications, Biomaterials 2008;29(28):3762-70.
(Continued)

*Primary Examiner* — Carlos Azpuru
*Assistant Examiner* — Casey Hagopian
(74) *Attorney, Agent, or Firm* — Stites & Harbison PLLC; Sean P. Ritchie; Richard S. Myers, Jr.

(57) ABSTRACT

Embodiments of the present inventions comprise composites of polyurethane(s), osteoconductive matrix, and, optionally, a growth factor. Embodiments further comprise methods of making such composite and uses thereof. The osteoconductive matrix can be a tricalcium phosphate, bioglass, or the like, and can include particles that are surface modified. Growth factors can be provided in powder form, including bone morphogenic proteins such as rhBMP-2. A composition may be moldable and/or injectable. After implantation or injection, a composition may be set to form a porous composite that provides mechanical strength and supports the in-growth of cells.

32 Claims, 25 Drawing Sheets

Related U.S. Application Data is a continuation-in-part of application No. 13/280,299, filed on Oct. 24, 2011, now abandoned, which is a continuation-in-part of application No. 12/608,850, filed on Oct. 29, 2009, now Pat. No. 9,333,276.

(60) Provisional application No. 61/406,098, filed on Oct. 22, 2010, provisional application No. 61/433,944, filed on Jan. 18, 2011, provisional application No. 61/109,892, filed on Oct. 30, 2008, provisional application No. 61/120,836, filed on Dec. 8, 2008, provisional application No. 61/242,758, filed on Sep. 15, 2009.

(56) References Cited

U.S. PATENT DOCUMENTS

| | | |
|---|---|---|
| 4,882,149 A | 11/1989 | Spector |
| RE33,161 E | 2/1990 | Brown et al. |
| 4,902,296 A | 2/1990 | Bolander et al. |
| RE33,221 E | 5/1990 | Brown et al. |
| 5,034,059 A | 7/1991 | Constantz |
| 5,047,031 A | 9/1991 | Constantz |
| 5,053,212 A | 10/1991 | Constantz |
| 5,129,905 A | 7/1992 | Constantz |
| 5,149,368 A | 9/1992 | Liu et al. |
| 5,262,166 A | 11/1993 | Liu et al. |
| 5,290,558 A | 3/1994 | O'Leary et al. |
| 5,336,264 A | 8/1994 | Constantz |
| 5,417,975 A | 5/1995 | Lussi et al. |
| 5,462,722 A | 10/1995 | Liu et al. |
| 5,507,813 A | 4/1996 | Dowd et al. |
| 5,525,148 A | 6/1996 | Chow et al. |
| 5,542,973 A | 8/1996 | Chow et al. |
| 5,573,771 A | 11/1996 | Geistlich et al. |
| 5,578,662 A | 11/1996 | Bennett |
| 5,605,713 A | 2/1997 | Boltong |
| 5,650,176 A | 7/1997 | Lee et al. |
| 5,717,006 A | 2/1998 | Daculsi et al. |
| 5,899,939 A | 5/1999 | Boyce et al. |
| 5,948,386 A | 9/1999 | Katti et al. |
| 6,001,394 A | 12/1999 | Daculsi et al. |
| 6,002,065 A | 12/1999 | Constantz |
| 6,066,681 A | 5/2000 | Kaplan |
| 6,123,731 A | 9/2000 | Boyce et al. |
| 6,123,781 A | 9/2000 | Shimazawa |
| 6,206,957 B1 | 3/2001 | Driessens et al. |
| 6,207,767 B1 | 3/2001 | Bennett |
| 6,294,041 B1 | 9/2001 | Boyce et al. |
| 6,294,187 B1 | 9/2001 | Boyce et al. |
| 6,306,177 B1 | 10/2001 | Felt |
| 6,332,779 B1 | 12/2001 | Boyce et al. |
| 6,339,130 B1 | 1/2002 | Bennett |
| 6,376,742 B1 | 4/2002 | Zdrahala |
| 6,399,693 B1 | 6/2002 | Brennan et al. |
| 6,696,073 B2 | 2/2004 | Boyce et al. |
| 7,291,345 B2 | 11/2007 | Winterbottom et al. |
| 7,985,414 B2 | 7/2011 | Knaack et al. |
| 8,002,843 B2 | 8/2011 | Knaack et al. |
| 8,425,893 B2 | 4/2013 | Knaack et al. |
| 9,333,276 B2 * | 5/2016 | Guelcher ............. A61L 27/44 |
| 2002/0028766 A1 * | 3/2002 | Papadimitriou ..... A61K 9/0014 514/21.92 |
| 2003/0144743 A1 | 7/2003 | Edwards et al. |
| 2004/0091462 A1 | 5/2004 | Lin et al. |
| 2004/0146543 A1 | 7/2004 | Shimp et al. |
| 2005/0013793 A1 | 1/2005 | Beckman |
| 2005/0220771 A1 * | 10/2005 | Deslauriers ............ A61L 27/18 424/93.7 |
| 2005/0238683 A1 | 10/2005 | Adhikari et al. |
| 2006/0034769 A1 | 2/2006 | Kohn et al. |
| 2006/0216323 A1 | 9/2006 | Knaack et al. |
| 2007/0100449 A1 | 5/2007 | O'Neil et al. |
| 2007/0190108 A1 | 8/2007 | Datta et al. |
| 2007/0191963 A1 | 8/2007 | Winterbottom et al. |
| 2007/0299151 A1 | 12/2007 | Guelcher et al. |
| 2009/0130174 A1 | 5/2009 | Guelcher et al. |
| 2009/0221784 A1 | 9/2009 | Guelcher et al. |
| 2010/0068171 A1 | 3/2010 | Guelcher et al. |
| 2010/0112032 A1 | 5/2010 | Guelcher et al. |
| 2010/0247672 A1 | 9/2010 | Guelcher et al. |
| 2010/0297082 A1 | 11/2010 | Guelcher et al. |
| 2011/0237704 A1 | 9/2011 | Guelcher et al. |
| 2012/0183622 A1 | 7/2012 | Guelcher et al. |

FOREIGN PATENT DOCUMENTS

| | | |
|---|---|---|
| WO | 2004069890 | 8/2004 |
| WO | 2006055261 | 5/2006 |
| WO | WO 2007017756 A2 * | 2/2007 |
| WO | 2007123536 | 11/2007 |
| WO | 2009026387 | 2/2009 |
| WO | 2009033088 | 3/2009 |
| WO | 20090033102 | 3/2009 |
| WO | 2010059389 | 5/2010 |
| WO | 2011075183 | 6/2011 |
| WO | 2014026052 | 8/2012 |
| WO | 2012134540 | 10/2012 |

OTHER PUBLICATIONS

Baker et al., Plast Reconstr Surg 2002;109:1789-1796.
Bennett S, Connolly K, Lee DR, Jiang Y, Buck D, Hollinger JO, Gruskin EA. Initial biocompatibility studies of a novel degradable polymeric bone substitute that hardens in situ. Bone 1996; 19(1, Supplement):101S-107S.
Bonzani et al., Synthesis of two-component injectable polyurethanes for bone tissue engineering, Biomaterials 2007;28:423-33; Hafeman et al., Pharm Res 2008;25(10):2387-99.
Boyce et al., Cellular Penetration and Bone Formation Depends Upon Allograft Bone Fraction in a Loadbearing Composite Implant. 2005. p. 133.
Chim et al., Biomaterials in Craniofacial Surgery Experimental Studies and Clinical Application, J Craniofac Surg 2009;20:29-33.
Clarkin et al., Comparison of an experimental bone cement with a commercial control, HydrosetTM, J Mater Sci: Mater Med 2009;20:1563-1570.
Ferrari and co-workers' in Ferrari RJ, Sinner JW, Bill JC, Brucksch WF. Compounding polyurethanes: Humid aging can be controlled by choosing the right intermediate. Ind. Eng. Chem. 1958;50(7):1041-1044.
Goma et al., Preparation, degradation, and calcification of biodegradable polyurethane foams for bone graft substitutes, J Biomed Mater Res Pt A 2003;67A(3):813-27.
Guelcher et al., Synthesis and In Vitro Biocompatibility of Injectable Polyurethane Foam Scaffolds, Tissue Eng 2006;12(5):1247-1259.
Guelcher et al., Tissue Engineering 2007;13(9):2321-2333.
Guelcher, Tissue Engineering: Part B, 14 (1) 2008, pp. 3-17.
Hafeman et al., Injectable Biodegradable Polyurethane Scaffolds with Release of Platelet-derived Growth Factor for Tissue Repair and Regeneration, Pharmaceutical Research 2008;25(10):2387-99.
Hasegawa et al., A 5-7 year in vivo study of high-strength hydroxyapatite/poly(L-lactide) composite rods for the internal fixation of bone fractures, Biomaterials 2006;27:1327-1332.
Hollier et al., Clin Plastic Surg 2004;31:423-428.
Hooper, et al., J. Bioactive and Compatible Polymers, 1995, 10:327-340.
Hurley, et al., Milit. Med. 1957, 101-104.
James et al., Biomaterials 20:2203-2213, 1999.
Karageorgiou et al., Biomaterials 26:5474-5491, 2005.
Kershaw, Pharm. J. 6:537, 1963.
Klaitwatter et al., J. Biomed. Mater. Res. Symp. 2:161, 1971.
Lewandrowski, et al., J. Biomed. Mater. Res., 1996, 31:365-372.
Lewis et al., J Biomed Mater Res Part B : Appl Biomater 2007;81B:371-386.
Malinin et al., Particulate Bone Allograft Incorporation in Regeneration of Osseous Defects; Importance of Particle Sizes, Open Orthop J 2007;1:19-24.

(56) References Cited

OTHER PUBLICATIONS

Moreira-Gonzalez et al., Clinical Outcome in Cranioplasty: Critical Review in Long-Term Follow-Up, J Craniofac Surg 2003;14:144-153.
Murphy et al., Tissue Engineering 8(1):43-52, 2002.
Neuendorf et al., Adhesion between biodegradable polymers and hydroxyapatite: Relevance to synthetic bone-like materials and tissue engineering scaffolds, Acta Biomater 2008;4:1288-1296.
Oertel, Günter, ed., Polyurethane Handbook, Hanser Gardner Publications, Inc. Cincinnati, Ohio, 99-108 (1994).
Pulapura, et al., Biopolymers, 1992, 32: 411-417.
Reddi, et al., Proc. Nat. Acad. Sci., 1972, 69:1601-1605.
Simmons, et al, Biotechnol. Appl. Biochem., 1993, 17:23-29.
Skarja et al., J App Poly Sci 2000;75:1522-34.
Storey at el., Hydrolyzable Poly (ester-urethane) Networks from L-Lysine Diisocyanate and D,L-Lactide/e-Caprolactone Homo- and Copolyester Triols, Journal of Polymer Science, Part A: Polymer Chemistry 1994;32(12):2345-2363.
Szycher, M, Szycher's Handbook of Polyurethanes, CRC Press, New York, New York, (1999).
Zhang J-Y, Beckman EJ, Piesco NJ, Agarwal S. A new peptide-based urethane polymer: synthesis, biodegradation, end potential to support cell growth in vitro. Biomaterials 2000;21 :1247-1258.
Zhang J, Doll B, Beckman J, Hollinger JO. Three-dimensional biocompatible ascorbic acid-containing scaffold for bone tissue engineering. Tissue Engineering 2003;9(6)1 143-1157.
Zhang J, Doll B, Beckman E, Hollinger JO. A biodegradable polyurethane-ascorbic acid scaffold for bone tissue engineering. J. Biomed. Mater. Res. 2003;67A(2):389-400.
Zhang J-Y, Beckman EJ, Hu J, Yuang G-G, Agarwal S, Hollinger JO. Synthesis, biodegradability, and biocompatibility of lysine diisocyanate-glucose polymers. Tissue Engineering 2002;8(5):771-785.
Larsson S, Stadelmann VA, Arnoldi J, Behrens M, Hess B, Procter P, et al. Injectable calcium phosphate cement for augmentation around cancellous bone screws. In vivo biomechanical studies. Journal of Biomechanics. 2012;45(7):1156-60.
Li, B., et al., The effects of rhBMP-2 released from biodegradable polyurethane/microsphere composite scaffolds on new bone formation in rat femora Biomaterials, 2009, 30(35), 6768-6779.
Libicher M, Hillmeier J, Liegibel U, Sommer U, Pyerin W, Vetter M, et al. Osseous integration of calcium phosphate in osteoporotic vertebral fractures after kyphoplasty: initial results from a clinical and experimental pilot study. Osteoporos Int. 2006;17(8):1208-15. Epub Jun. 13, 2006.
Lu, Q.-W., T.R. Hoye, and C.W. Macosko, Reactivity of common functional groups with urethanes: Models for reactive compatibilization of thermoplastic polyurethane blends. Journal of Polymer Science Part A: Polymer Chemistry, 2002. 40(14): p. 2310-2328.
Mader E. Study of fibre surface treatments for control of interphase properties in composites. Composites Science and Technology. 1997;57(8):1077-88.
Maestretti G, Cremer C, Otten P, Jakob RP. Prospective study of standalone balloon kyphoplasty with calcium phosphate cement augmentation in traumatic fractures. Eur Spine J. 2007;16(5):601-10. Epub Nov. 23, 2006.
Mishra, P.K., et al., Isocyanates induces DNA damage, apoptosis, oxidative stress, and inflammation in cultured human lymphocytes. Journal of Biochemical and Molecular Toxicology, 2008. 22(6): p. 429-440.
Mosse WKJ, Koppens ML, Gengenbach TR, Scanlon DB, Gras SL, Ducker WA. Peptides Grafted from Solids for the Control of Interfacial Properties. Langmuir. 2009;25(3):1488-94.
Nazarian A, Meier D, Mueller R, Snyder BD. Functional Dependence of Cancellous Bone Shear Properties on Trabecular Microstructure Evaluated Using Time-Lapsed Micro-Computed Tomographic Imaging and Torsion Testing. Journal of Orthopaedic Research. 2009;27(12):1667-74.

Olivier A, Raquez J-M, Dubois P, Damman P. Semi-crystalline poly(epsilon-caprolactone) brushes on gold substrate via "grafting from" method New insights with AFM characterization. European Polymer Journal. 2011;47(1):31-9.
Page JM, Prieto EM, Dumas JE, Zienkiewicz KJ, Wenke JC, Brown-Baer P, et al. Biocompatibility and chemical reaction kinetics of injectable, settable polyurethane/allograft bone biocomposites. Acta Biomaterialia. 2012;8(12):4405-16.
Penczek S, Duda A, Kowalski A, Libiszowski J, Majerska K, Biela T. On the mechanism of polymerization of cyclic esters induced by Tin(II) octoate. Macromolecular Symposia. 2000;157:61-70.
Pons, F., et al., Effect of toluene diisocyanate and its corresponding amines on viability and growth of human lung fibroblasts in culture. Cell Biology and Toxicology, 1999. 15(5): p. 333-340.
Ruppender NS, Merkel AR, Martin TJ, Mundy GR, Sterling JA, Guelcher SA. Matrix Rigidity Induces Osteolytic Gene Expression of Metastatic Breast Cancer Cells. Plos One. 2010;5(11).
Russell TA, Leighton RK. Comparison of Autogenous Bone Graft and Endothermic Calcium Phosphate Cement for Defect Augmentation in Tibial Plateau Fractures. Journal of Bone and Joint Surgery—American Volume. 2008;90A(10):2057-61.
Ryszkowska JL, Auguscik M, Sheikh A, Boccaccini AR. Biodegradable polyurethane composite scaffolds containing Bioglass (R) for bone tissue engineering. Composites Science and Technology. 2010;70(13):1894-908.
Saeri MR, Afshar A, Ghorbani M, Ehsani N, Sorrell CC. The wet precipitation process of hydroxyapatite. Materials Letters. 2003;57(24-25):4064-9.
Saravanapavan P, Jones JR, Pryce RS, Hench LL. Bioactivity of gel-glass powders in the CaO—SiO2 system: A comparison with ternary (CaO—P2O5—SiO2) and quaternary glasses (SiO2—CaO—P2O5—Na2O). J Biomed Mater Res Part A. 2003;66A(1):110-9.
Schwartz, Z., et al., Clinical evaluation of demineralized bone allograft in a hyaluronic acid carrier for sinus lift augmentation in humans: a computed tomography and histomorphometric study. Clinical Oral Implants Research, 2007. 18(2): p. 204-211.
Semsarzadeh, M.A. and A.H. Navarchian, Effects of NCO/OH ratio and catalyst concentration on structure, thermal stability, and crosslink density of poly(urethane-isocyanurate). Journal of Applied Polymer Science, 2003. 90(4): p. 963-972.
Simpson D, Keating JF. Outcome of tibial plateau fractures managed with calcium phosphate cement. Injury—International Journal of the Care of the Injured. 2004;35(9):913-8.
Sivak, W.N., et al., Catalyst-dependent drug loading of LDI-glycerol polyurethane foams leads to differing controlled release profiles. Acta Biomaterialia, 2008.4(5): p. 1263-1274.
Steven, F.S.J., D. S., Purification and amino acid composition of monomeric and polymeric collagens. . Biochem. J., 1967. 104: p. 534-536.
Tanner KE. Bioactive composites for bone tissue engineering. Proceedings of the Institution of Mechanical Engineers Part H—Journal of Engineering in Medicine. 2010;224(H12):1359-72.
Timmer, M.D., et al., In vitro cytotoxicity of injectable and biodegradable poly(propylene fumarate)-based networks: Unreacted macromers, cross-linked networks, and degradation products. Biomacromolecules, 2001 4(4): p. 1026-1033.
Verlaan JJ, Oner FC, Dhert WJA. Anterior spinal column augmentation with injectable bone cements. Biomaterials. 2006;27(3):290-301.
Verne E, Vitale-Brovarone C, Bui E, Bianchi CL, Boccaccini AR. Surface functionalization of bioactive glasses. J Biomed Mater Res Part A. 2009;90A(4):981-92.
Wagoner Johnson, A.J. and B.A. Herschler, A review of the mechanical behavior of CaP and CaP/polymer composites for applications in bone replacement and repair. Acta Biomaterialia, 2011. 7(1): p. 16-30.
Wang X, Yang J, Zhou J. Crystallization behavior of poly(epsilon-caprolactone) grafted on silicon surface. E-Polymers. 2011.
Wang Z, Lu B, Chen L, Chang J. Evaluation of an osteostimulative putty in the sheep spine. J Mater Sci-Mater Med. 2011;22(1)185-91.
Wang, Z., et al., Preparation and rapid degradation of nontoxic biodegradable polyurethanes based on poly(lactic acid)-poly(ethyl-

(56) References Cited

OTHER PUBLICATIONS ene glycol)-poly(lactic acid) and l-lysine diisocyanate. Polymer Chemistry, 2011. 2(3): p. 601-607.
Yoon KR, Lee KB, Chi YS, Yun WS, Joo SW, Choi IS. Surface-initiated, enzymatic polymerization of biodegradable polyesters. Advanced Materials. 2003;15(24):2063-+.
Yoshii T, Dumas JE, Okawa A, Spengler DM, Guelcher SA. Synthesis, characterization of calcium phosphates/polyurethane composites for weight-bearing implants. Journal of Biomedical Materials Research Part B—Applied Biomaterials. 2012;100B(1):32-40.
Miyazaki M, Morishita Y, He W, Hu M, Sintuu C, Hymanson HJ, et al. A porcine collagen-derived matrix as a carrier for recombinant human bone morphogenetic protein-2 enhances spinal fusion in rats. Spine J. Jan.-Feb. 2009;9(1):22-30.
Pisanova E, Mader E. Acid-base interactions and covalent bonding at a fiber-matrix interface: contribution to the work of adhesion and measured adhesion strength. Journal of Adhesion Science and Technology. 2000;14(3):415-36.
Anderson DD, Van Hofwegen C, Marsh JL, Brown TD. Is elevated contact stress predictive of post-traumatic osteoarthritis for imprecisely reduced tibial plafond fractures? J Orthop Res. Jan. 2011;29(1):33-9.
Urban RM, Turner TM, Hall DJ, Inoue N, Gitelis S. Increased bone formation using calcium sulfate-calcium phosphate composite graft. Clin Orthop Relat Res. Jun. 2007;459:110-7.
Ikenaga M, Hardouin P, Lemaitre J, Andrianjatovo H, Flautre B. Biomechanical characterization of a biodegradable calcium phosphate hydraulic cement: a comparison with porous biphasic calcium phosphate ceramics. J Biomed Mater Res. Apr. 1998;40(1):139-44.
Urban RM, Turner TM, Hall DJ, Infanger S, Cheema N, Lim TH. Healing of large defects treated with calcium sulfate pellets containing demineralized bone matrix particles. Orthopedics. May 2003;26(5 Suppl):s581-5.
Greish YE, Brown PW. Phase evolution during the formation of stoichiometric hydroxyapatite at 37.4 degrees C. J Biomed Mater Res B Appl Biamater. Oct. 15, 2003;67(1):632-7.
Otsu N. A threshold selection method for gray level histogram. IEEE Trans Syst Man Cybern. 1978;SMC-9(1)(62-66).
Allen MR, Hogan HA, Hobbs WA, Koivuniemi AS, Koivuniemi MC, Burr DB. Raloxifene enhances material-level mechanical properties of femoral cortical and trabecular bone. Endocrinology. 2007;148(8):3908-13.
Amendola L, Gasbarrini A, Fosco M, Simoes CE, Terzi S, Delure F, et al. Fenestrated pedicle screws for cement-augmented purchase in patients with bone softening: a review of 21 cases. J Orthop Traumatal. 2011;12(4):193-9.
Bagley, E.B., The seperation of elastic and visous effects in polymer flow. Transactions of the Society of Rheology, 1961: p. 355-368.
Barsbay M, Gueven G, Stenzel MH, Davis TP, Barner-Kowollik C, Barner L. Verification of controlled grafting of styrene from cellulose via radiation-induced RAFT polymerization. Macromolecules. 2007;40(20):7140-7.
Bashoor-Zedah, M., Baroud, G. and Bohner, M., Biomaterials, 2011, 32(27), 6362-6373.
Belfrage, O., et al., Acta Orthopaedica, 2011, 82(2), 228-233.
Bil M, Ryszkowska J, Roether JA, Bretcanu O, Boccaccini AR. Bioactivity of polyurethane-based scaffolds coated with Bioglass((R)). Biomedical Materials. 2007;2(2):93-101.
Blaker, et al., Expert review of medical devices, 2005, 2, 303.
Boccaccini AR, Blaker JJ. Bioactive composite materials for tissue engineering scaffolds. Expert Review of Medical Devices. 2005;2(3):303-17.
Bohner M. Design of ceramic-based cements and putties for bone graft substitution. Eur Cell Mater. 2010;20:1-12. Epub Jun. 25, 2010.
Bretcanu O, Misra S, Roy I, Renghini C, Fiori F, Boccaccini AR, et al. In vitro biocompatibility of 45S5 Bioglass (R)-derived glass-ceramic scaffolds coated with poly(3-hydroxybutyrate). Journal of Tissue Engineering and Regenerative Medicine. 2009;3(2):139-48.

Brown HR, Russell TP. Entanglements at polymer surfaces and interfaces. Macromolecules. 1996;29(2):798-800.
Buckley M.J. and E.J. Beckman, Adhesive Use in Oral and Maxillofacial Surgery. Oral and Maxillofacial Surgery Clinics of North America, 2010.22(1): p. 195-199.
Cammisa, F.P., et al., Two-year fusion rate equivalency between Grafton (R) DBM gel and autograft in posterolateral spine fusion. Spine, 2004. 29(6): p. 660-666.
Caracciolo, P., F. Buffa, and G. Abraham, Effect of the hard segment chemistry and structure on the thermal and mechanical properties of novel biomedical segmented poly(esterurethanes). Journal of Materials Science: Materials in Medicine, 2009. 20(1): p. 145-155.
Chan, C., et al., Evaluation of Bioglass/dextran composite as a bone graft substitute. International Journal of Oral and Maxillofacial Surgery, 2002. 31(1): p. 73-77.
Chazono, M., et al., Bone formation and bioresorption after implantation of injectable beta-tricalcium phosphate granules-hyaluronate complex in rabbit bone defects. Journal of Biomedical Materials Research Part A, 2004. 70A(4): p. 542-549.
Shen QZ, Rezwan K, Armitage D, Nazhat SN, Boccaccini AR. The surface functionalization of 45S5 Bioglass (R)-based glass-ceramic scaffolds and its impact on bioactivity. J Mater Sci: Mater Med. 2006;17(11):979-87.
Dumas, J.E., et al. Synthesis and Characterization of an Injectable Allograft Bone/polymer Composite Bone Void Filler with Tunable Mechanical Properties. Tissue Eng Part A, 2010. 16(8): p. 2505-18.
Dumas, J.E., et al., Synthesis, characterization, and remodeling of weight-bearing allograft bone/polyurethane composites in the rabbit. Acta Biomaterialia, 2010. 6(7): p. 2394-2406.
Elliott, S.L., et al., Identification of biodegradation products formed by L-phenylalanine based segmented polyurethaneureas. Journal of Biomaterials Science Polymer Edition, 2002. 13(6): p. 691-711.
Ertel, S.I., et al., In-Vitro Study of the Intrinsic Toxicity of Synthetic Surfaces to Cells. Journal of Biomedical Materials Research, 1994. 28(6): p. 667-675.
Fogler, H.S., Elements of Chemical Reaction Engineering. 4th Ed. ed. 1999, Upper Saddle River, NJ: Pearson Education.
88. Trabecular orientation. Journal of Biomechanics. 1996;29(10):1309-17.
Friedman, C.D., et al., BoneSource (TM) hydroxyapatite cement: A novel biomaterial for craniofacial skeletal tissue engineering and reconstruction. Journal of Biomedical Materials Research, 1998. 43(4): p. 428-432.
Garnier KB, Dumas R, Rumelhart C, Allot ME. Mechanical characterization in shear of human femoral cancellous bone: torsion and shear tests. Medical Engineering & Physics. 1999;21(9):641-9.
Gasparini, G., et al., Cranial Reshaping Using Methyl Methacrylate: Technical Note. Journal of Craniofacial Surgery, 2009. 20(1): p. 184-190.
GluckHirsch, J.B. and J.L. Kokini, Determination of the molecular weight between crosslinks of waxy maize starches using the theory of rubber elasticity. Journal of Rheology, 1997. 41(1): p. 129-139.
Guan, J.J., et al., Biodegradable poly(ether ester urethane)urea elastomers based on poly(ether ester) triblock copolymers and putrescine: synthesis, characterization and cytocompatibility. Biomaterials, 2004. 25(1): p. 85-96.
Gurarslan A, Shen J, Tonelli AE. Behavior of Poly(epsilon-caprolactone)s (PCLs) Coalesced from Their Stoichiometric Urea Inclusion Compounds and Their Use as Nucleants for Crystallizing PCL Melts: Dependence on PCL Molecular Weights. Macromolecules. 2012;45(6):2835-40.
Hafeman, A.E., et al., Characterization of the degradation mechanisms of lysine-derived aliphatic poly(ester urethane) scaffolds. Biomaterials, 2011. 32(2): p. 419-29.
Hall JA, Beuerlein MJ, McKee MD. Open reduction and internal fixation compared with circular fixator application for bicondylar tibial plateau fractures. Surgical technique. J Bone Joint Surg Am. 2009;91 Suppl 2 Pt 1:74-88. Epub Mar. 11, 2009.
Heiney PA, Gruneberg K, Fang JY, Dulcey C, Shashidhar R. Structure and growth of chromophore-functionalized (3-aminopropyl)triethoxysilane self-assembled on silicon. Langmuir. 2000;16(6):2651-7.

(56) References Cited

OTHER PUBLICATIONS

Hench LL. The story of Bioglass (R). J Mater Sci-Mater Med. 2006;17(11):967-78.
Hoppe A, Gueldal NS, Boccaccini AR. A review of the biological response to ionic dissolution products from bioactive glasses and glass-ceramics. Biomaterials. 2011;32(11):2757-74.
Hoven, V.P., et al., Surface-charged chitosan: Preparation and protein adsorption. Carbohydrate Polymers, 2007. 68(1): p. 44-53.
Jiang G, Evans ME, Jones IA, Rudd CD, Scotchford CA, Walker GS. Preparation of poly(epsilon-caprolactone)/continuous bioglass fibre composite using monomer transfer moulding for bone implant. Biomaterials. 2005;26(15):2281-8.
Jiang G, Walker GS, Jones IA, Rudd CD. XPS identification of surface-initiated polymerisation during monomer transfer moulding of poly(epsilon-caprolactone)/Bioglass (R) fibre composite. Appl Surf Sci. 2005;252(5):1854-62.
Jiang, et al., Journal of Applied Polymer Science, 2009, 114, 658.
Larsson S, Procter P. Optimising implant anchorage (augmentation) during fixation of osteoporotic fractures: Is there a role for bone-graft substitutes? Injury—International Journal of the Care of the Injured. 2011;42:S72-S6.
Kokubo et al. How useful is SBF in predicting in vivo bone bioactivity? Biomaterials, 2006;27(15):2907-15.
Kretlow, J.D., et al., Injectable Biomaterials for Regenerating Complex Craniofacial Tissues. Advanced Materials, 2009. 21(32-33): p. 3368-3393.
Kunze C, Freier T, Helwig E, Sandner B, Reif D, Wutzler A, et al. Surface modification of tricalcium phosphate for improvement of the interfacial compatibility with biodegradable polymers. Biomaterials. 2003;24(6):967-74.
Gautschi, O.P., S.P. Frey, and R. Zellweger, Bone morphogenetic proteins in clinical applications. ANZ J Surg, 2007. 77(8): p. 626-31.
Han, D., et al., Optimal delivery systems for bone morphogenetic proteins in orthopedic applications should model initial tissue repair structures by using a heparin-incorporated fibrin-fibronectin matrix. Med Hypotheses, 2008. 71(3): p. 374-8.
Garrison, K.R., et al., Clinical effectiveness and cost-effectiveness of bone morphogenetic proteins in the non-healing of fractures and spinal fusion: a systematic review. Health Technol Assess, 2007. 11(30): p. 1-150, iii-iv.
Shah, M.M., M.D. Smyth, and A.S. Woo, Adverse facial edema associated with off-label use of recombinant human bone morphogenetic protein-2 in cranial reconstruction for craniosynostosis. Case report. J Neurosurg Pediatr, 2008. 1(3): p. 255-7.
Ueeck BA. Penetrating injuries to the face: delayed versus primary treatment—considerations for delayed treatment. J oral Maxillofac Surg. Jun. 2007;65(6):1209-14.
Shermak MA, Wong L, Inoue N, Nicol T. Reconstruction of complex cranial wounds with demineralized bone matrix and bilayer artificial skin. J Craniofac Surg. May 2000;11(3):224-31.
Lemperle SM, Calhoun CJ, Curran RW, Holmes RE. Bony healing of large cranial and mandibular defects protected from soft-tissue interposition: A comparative study of spontaneous bone regeneration, osteoconduction, and cancellous autografting in dogs. Plast Reconstr Surg. Mar. 1998;101(3):660-72.
Khan Y, Yaszemski MJ, Mikos AG, Laurencin CT. Tissue engineering of bone: material and matrix considerations. J Bone Joint Surg Am. Feb. 2008;90 Suppl 1:36-42.
Tessier P. Autogenous bone grafts taken from the calvarium for facial and cranial applications. Clin Plast Surg. Oct. 1982;9(4):531-8.
Wan DC, Aalami OO, Wang Z, Nacamuli RP, Lorget F, Derynck R, et al. Differential gene expression between juvenile and adult dura mater: a window into what genes play a role in the regeneration of membranous bone. Plast Reconstr Surg. Sep. 15, 2006;118(4):851-61.
Smith DM, Cooper GM, Mooney MP, Marra KG, Losee JE. Bone morphogenetic protein 2 therapy for craniofacial surgery. J Craniofac Surg. Sep. 2008;19(5):1244-59.
Lew TA, Walker JA, Wenke JC, Blackbourne LH, Hale RG. Characterization of craniomaxillofacial battle injuries sustained by United States service members in the current conflicts of Iraq and Afghanistan. J oral Maxillofac Surg. Jan. 2009;68(1):3-7.
Kauvar DS, Wolf SE, Wade CE, Cancio LC, Renz EM, Holcomb JB. Burns sustained in combat explosions in Operations Iraqi and Enduring Freedom (OIF/OEF explosion burns). Burns. Nov. 2006;32(7):853-7.
Schmitz JP, Hollinger JO, Milam SB. Reconstruction of bone using calcium phosphate bone cements: A critical review. J Oral Maxillofac Surg. 1999;57:1122-6.
Elshahat A, Shermak MA, Inoue N, Chao EY, Manson P. The use of Novabone and Norian in cranioplasty: a comparative study. J Craniofac Surg. May 2004;15(3):483-9.
Moghadam HG, Sandor GK, Holmes HH, Clokie CM. Histomorphometric evaluation of bone regeneration using allogeneic and alloplastic bone substitutes. J oral Maxillofac Surg. Feb. 2004;62(2):202-13.
Clokie CM, Moghadam H, Jackson MT, Sandor GK. Closure of critical sized defects with allogenic and alloplastic bone substitutes. J Craniofac Surg. Jan. 2002;13(1):111-21; discussion 22-3.
Goldberg CS, Antonyshyn O, Midha R, Fialkov JA. Measuring Pulsatile Forces on the Human Cranium. J Craniofacial Surgery. 2005;16(1):134-9.
Spector J, Luchs J, Mehera B, Greenwald J, Smith L, Longaker M. Expression of bone morphogenetic proteins during membranous bone healing. Plastic Reconstr Surg. 2001;107:124-34.
Boerckel JD, Kolambkar YM, Dupont KM, Uhrig BA, Phelps EA, Stevens HY, et al. Effects of protein dose and delivery system on BMP-mediated bone regeneration. Biomaterials. Aug. 2011;32(22):5241-51.
Brown KV, Li B, Guda T, Perrien DS, Guelcher SA, Wenke JC. Improving Bone Formation in a Rat Femur Segmental Defect by Controlling Bone Morphogenetic Protein-2 Release. Tissue Eng Part A. Apr. 3, 2011.
Smith DM, Afifi AM, Cooper GM, Mooney MP, Marra KG, Losee JE. BMP-2-based repair of large-scale calvarial defects in an experimental model: regenerative surgery in cranioplasty. J Craniofac Surg. Sep. 2008;19(5):1315-22.
Haidar ZS, Hamdy RC, Tabrizian M. Delivery of recombinant bone morphogenetic proteins for bone regeneration and repair. Part A: Current challenges in BMP delivery. Biotechnol Lett. Dec. 2009;31(12):1817-24.
McKay WF, Peckham SM, Badura JM. A comprehensive clinical review of recombinant human bone morphogenetic protein-2 (INFUSE Bone Graft). Int Orthop. Dec. 2007;31(6):729-34.
Carter TG, Brar PS, Tolas A, Beirne OR. Off-Label Use of Recombinant Human Bone Morphogenetic Protein-2 (rhBMP-2) for Reconstruction of Mandibular Bone Defects in Humans. J oral Maxillofac Surg. 2008;66:1417-25.
Herford AS, Boyne PJ. Reconstruction of Mandibular Continuity Defects With Bone Morphogenetic Protein-2 (rhBMP-2). J oral Maxillofac Surg. 2008;66:616-24.
Panetta NJ, Gupta DM, Longaker MT. Bone tissue engineering scaffolds of today and tomorrow. J Craniofac Surg. Sep. 2009;20(5):1531-2.
Hollister SJ, Lin CY, Saito E, Schek RD, Taboas JM, Williams JM, et al. Engineering craniofacial scaffolds. Orthod Craniofac Res. Aug. 2005;8(3):162-73.
Li JQ, Salovey R. Model Filled Polymers: The Effect of Particle Size on the Rheology of Filled Poly(methylmethacrylate) Composites. Polym Eng Sci. 2004;44:452-62.
Baroud G, Cayer E, Bohner M. Rheological characterization of concentrated aqueous beta-tricalcium phosphate suspensions: the effect of liquid-to-powder ratio, milling time, and additives. Acta Biomater. May 2005;1(3):357-63.
Bohner M. Calcium orthophosphates in medicine: from ceramics to calcium phosphate cements. Injury. 2000;31(Supplement 4):S-D37-47.
Lewis G. Percutaneous Vertebroplasty and Kyphoplasty for the Stand-Alone Augmentation of Osteoporosis-Induced Vertebral Compression Fractures: Present Status and Future Directions. J Biomed Mater Res Part B : Appl Biomater. 2007;81B:371-86.

(56) References Cited

OTHER PUBLICATIONS

Clarkin OM, Boyd D, Madigan S, Towler MR. Comparison of an experimental bone cement with a commercial control, HydrosetTM. J Mater Sci: Mater Med. 2009;20:1563-70.

Bohner M, Baroud G. Injectability of calcium phosphate pastes. Biomaterials. 2005;26(13)1553-63.

Cherng A, Takagi S, Chow LC. Effects of hydroxypropyl methylcellulose and other gelling agents on the handling properties of calcium phosphate cement. J Biomed Mater Res. Jun. 5, 1997;35(3):273-7.

Gilardino MS, Cabiling DS, Bartlett SP. Long-term follow-up experience with carbonated calcium phosphate cement (Norian) for cranioplasty in children and adults. Plastic and reconstructive surgery. Mar. 2009;123(3):983-94.

Torquato S, Truskett TM, Debenedetti PG. Is Random Close Packing of Spheres Well Defined? Phys Rev Let. 2000;84(10):2064-7.

Donath K, Laass M, Gunzl HJ. The histopathology of different foreign-body reactions in oral soft tissue and bone tissue. Virchows Arch A Pathol Anat Histopathol. 1992;420(2):131-7.

Takaoka K, Koezuka M, Nakahara H. Telopeptide-depleted bovine skin collagen as a carrier for bone morphogenetic protein. J Orthop Res. Nov. 1991;9(6):902-7.

Haidar ZS, Hamdy RC, Tabrizian M. Delivery of recombinant bone morphogenetic proteins for bone regeneration and repair. Part B: Delivery systems for BMPs in orthopaedic and craniofacial tissue engineering. Biotechnol Lett. Dec. 2009;31(12):1825-35.

Sheehan JP, Sheehan JM, Seeherman H, Quigg M, Helm GA. The safety and utility of recombinant human bone morphogenetic protein-2 for cranial procedures in a nonhuman primate model. J Neurosurg. Jan. 2003;98(1):125-30.

Kolambkar YM, Dupont KM, Boerckel JD, Huebsch N, Mooney DJ, Hutmacher DW, et al. An alginate-based hybrid system for growth factor delivery in the functional repair of large bone defects. Biomaterials. Jan. 2011;32(1):65-74.

Geiger M, Li RH, Friess W. Collagen sponges for bone regeneration with rhBMP-2. Adv Drug Deliv Rev. Nov. 28, 2003;55(12)1613-29.

Santos MI, Unger RE, Sousa RA, Reis RL, Kirkpatrick CJ. Crosstalk between osteoblasts and endothelial cells co-cultured on a polycaprolactone-starch scaffold and the in vitro development of vascularization. Biomaterials. Sep. 2009;30(26):4407-15.

Unger RE, Sartoris A, Peters K, Matta A, Migliaresi C, Kunkel M, et al. Tissue-like self-assembly in cocultures of endothelial cells and osteoblasts and the formation of microcapillary-like structures on three-dimensional porous biomaterials. Biomaterials. Sep. 2007;28(27):3965-76.

Szpalski M, Gunzburg R. Recombinant human bone morphogenetic protein-2: a novel osteoinductive alternative to autogenous bone graft? Acta Orthop Belg. Apr. 2005;71(2):133-48.

Jensen ED, Pham L, Billington CJ, Jr., Espe K, Carlson AE, Westendorf JJ, et al. Bone morphogenic protein 2 directly enhances differentiation of murine osteoclast precursors. J Cell Biochem. Mar. 1, 2010;109(4):672-82.

Okamoto M, Murai J, Yoshikawa H, Tsumaki N. Bone morphogenetic proteins in bone stimulate osteoclasts and osteoblasts during bone development. J Bone Miner Res. Jul. 2006;21(7):1022-33.

McGee MA, Findlay DM, Howie DW, Carbone A, Ward P, Stamenkov R, et al. The use of OP-1 in femoral impaction grafting in a sheep model. J Orthop Res. Sep. 2004;22(5):1008-15.

\* cited by examiner

SYNTHETIC POLYURETHANE COMPOSITE

RELATED APPLICATIONS

This application is a continuation-in-part of PCT International Application No. PCT/US11/57551, filed Oct., 24, 2011, which claims priority from U.S. Provisional Application Ser. No. 61/406,098, filed Oct. 22, 2010, and U.S. Provisional Application Ser. No. 61/433,944, filed Jan. 18, 2011; and a continuation-in-part of U.S. patent application Ser. No. 13/280,299, which is a continuation-in-part of Ser. No. 12/608,850, which claims priority from U.S. Provisional Application Ser. No. 61/242,758, filed Sep. 15, 2009, U.S. Provisional Application Ser. No 61/120,836, filed Dec. 8, 2008, and U.S. Provisional Application Ser. No. 61/109,892, filed Oct. 30, 2008; the entire disclosures of which are incorporated herein by this reference.

GOVERNMENT SUPPORT

This invention was made with government support under Grant Nos. W81XWH-04-2-0031, W81XWH-07-1-0211, and W81XWH-08-2-0034 awarded by the Department of Defense, and Grant No. DMR-0847711 awarded by the National Science Foundation. The United States Government has certain rights to this invention.

JOINT RESEARCH AGREEMENT

The present invention relates to subject matter developed pursuant to a Joint Reach Agreement between Vanderbilt University and Medtronic Sofamor Danek USA, Inc.

TECHNICAL FIELD

Embodiments of the present invention include composites and methods of using the composites. In particular, some embodiments include composites that comprise polyurethane, an osteoconductive matrix, and, optionally, a bioactive agent. Some embodiments include putty and injectable bone void filler composites that can be used for bone healing and/or weight-bearing applications.

BACKGROUND

There is a compelling clinical need for functional biomaterials that are weight-bearing and actively remodel. For example, the treatment of tibial fractures is frequently complicated by delayed union and nonunion. The standard of care for treatment of displaced tibial plateau fractures (e.g., split and localized depression fractures) is internal fixation, which in some cases requires grafting with autologous bone to augment the internal fixation. Inadequate anatomical reduction of tibial plateau fractures has been associated with a high (30-80%) incidence of arthritic change in the knee. In order to eliminate the need for invasive internal fixation devices, the potential of calcium phosphate bone cements to maintain anatomical reduction of tibial plateau fractures has been investigated. In a retrospective analysis of 26 patients, 61% of patients treated with buttress plating and bone grafting experienced loss of reduction after one year compared to 23% of patients treated with calcium phosphate cement. Thus the bone cement preserved anatomical reduction, presumably due to its compressive strength exceeding that of the trabecular bone in the tibial plateau. However, the cement is not biofunctional, since it does not extensively remodel and is not replaced by new bone.

Osteonecrosis of the femoral head, which typically leads to hip replacement at a young age (<40 years) and afflicts ~15,000 new patients each year, is another orthopaedic condition where treatment with functional biomaterials could improve patient outcomes. Hip replacement outcomes are not satisfactory, with failure rates ranging from 10-50% after five years. Non-invasive techniques, such as core decompression and nonvascularized bone grafting, have been used to treat early-stage osteonecrosis before collapse of the femoral head necessitates hip replacement. However, the results are varied with a 60-80% success rate, and outcomes are generally better in patients with very early-stage disease. Therefore, a non-invasive therapy accomplishing more predictable outcomes is desirable.

Injectable, functionally weight-bearing biomaterials that both possess initial mechanical strength comparable to host bone and maintain their initial strength while actively remodeling to form new bone would transform clinical management of a number of orthopaedic conditions. Functionally weight-bearing biomaterials for treatment of bone defects ideally possess five qualities: (1) biocompatibility of the material and its breakdown products, (2) injectability to enable less invasive application and fill irregularly shaped defects, (3) weight-bearing properties with strength comparable to that of healthy host bone at the defect site, (4) support of rapid cellular infiltration and remodeling at a rate that does not inhibit bone repair, and (5) delivery of biologics with proper release kinetics to accelerate bone formation and remodeling. Such a weight-bearing and/or biologically active biomaterial are not available.

Instead, commercially available injectable materials marketed as bone void fillers include calcium phosphate-based bone cements, which are osteoconductive, have compressive strengths comparable to trabecular bone (e.g., 5-40 MPa), and have fast setting times (<15 min). However, current calcium phosphates are subject to brittle fracture and graft migration, potentially leading to infections and requiring additional surgeries for repair or removal. To accelerate cellular infiltration and remodeling, implantable scaffolds with interconnected pores have been investigated, but interconnected pores have long been considered to significantly diminish the initial load-bearing properties of the materials, rendering them largely unsuitable for weight-bearing devices. Also, resorbable polymers have been blended with ceramics to yield weight-bearing composite implants that integrate and resorb, but these materials incorporate relatively low (e.g., 5-20 vol %) volumes of ceramic particles and the rate of remodeling is slow (<30% bony ingrowth after 4 years in a rabbit IM rod model) and scaled with the rate of polymer degradation. Furthermore, the incorporated particle generally have a size that is less than 20 µm.

Hence, there are remains a need for functional biomaterials that comprise synthetic allograft substitutes. There also remains a need for such composites that are injectable void fillers and/or putties, and that can have weight-bearing capabilities. Thus while currently available biomaterials address individually the requirements of a functional weight-bearing biomaterial, there is no device available that possesses more than three of the five key characteristics.

DEFINITIONS

The term "bioactive agent" is used herein to refer to compounds or entities that alter, promote, speed, prolong, inhibit, activate, or otherwise affect biological or chemical events in a subject (e.g., a human). For example, bioactive agents may include, but are not limited to osteogenic, osteoinductive, and osteoconductive agents, anti-HIV substances, anti-cancer substances, antibiotics, immunosuppressants, anti-viral agents, enzyme inhibitors, growth factors, neurotoxins, opioids, hypnotics, anti-histamines, lubricants, tranquilizers, anti-convulsants, muscle relaxants, anti-Parkinson agents, anti-spasmodics and muscle contractants including channel blockers, miotics and anti-cholinergics, anti-glaucoma compounds, anti-parasite agents, anti-protozoal agents, and/or anti-fungal agents, modulators of cell-extracellular matrix interactions including cell growth inhibitors and anti-adhesion molecules, vasodilating agents, inhibitors of DNA, RNA, or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotics, targeting agents, chemotactic factors, receptors, neurotransmitters, proteins, cell response modifiers, cells, peptides, polynucleotides, viruses, and vaccines. In certain embodiments, the bioactive agent is a drug. In certain embodiments, the bioactive agent is a small molecule.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, the United States Pharmacopeia-25/National Formulary-20, published by the United States Pharmcopeial Convention, Inc., Rockville Md., 2001, and the "Pharmazeutische Wirkstoffe", edited by Von Keemann et al., Stuttgart/New York, 1987, all of which are incorporated herein by reference. Drugs for human use listed by the U.S. Food and Drug Administration (FDA) under 21 C.F.R. §§330.5, 331 through 361, and 440 through 460, and drugs for veterinary use listed by the FDA under 21 C.F.R. §§500 through 589, all of which are incorporated herein by reference, are also considered acceptable for use in accordance with the present invention.

The term "bioactive glass" as used herein, refers to a group of glass-ceramic biomaterials that may be surface reactive. Certain bioactive glasses (bioglass), comprises $SiO_2$, $Na_2O$, CaO $P_2O_5$, and combinations thereof. An example of bioactive glass is Bioglass, including Bioglass 42S5. Various characteristics of bioactive glass make embodiments of bioactive glass suitable for use in PUR composites. For illustrative non-limiting purposes only, below are composition (wt %), structure, and index of bioactivity for various bioactive glasses.

|  | 45S5 | 45S5, 4F | 52S4, 6 | KGC Ceravital ® | A/W-GC |
|---|---|---|---|---|---|
| $SiO_2$ | 45 | 45 | 52 | 46.2 | 34.2 |
| $P_2O_5$ | 6 | 6 | 6 | — | 16.3 |
| CaO | 24.5 | 14.7 | 21 | 20.2 | 44.9 |
| $Ca(PO_3)_2$ | — | — | — | 25.5 | — |
| $CaF_2$ | — | 9.8 | — | — | 0.5 |
| MgO | — | — | — | 2.9 | 4.6 |
| $Na_2O$ | 24.5 | 25.5 | 21 | 4.8 | — |
| $K_2O$ | — | — | — | 0.4 | — |
| Structure | Glass | Glass | Glass | Glass-ceramic | Glass-ceramic |
| $I_B$ | 12.5 | 12.5 | 10.5 | 5.6 | 6.0 |

Certain bioactive glass may comprise less than 60 mol % $SiO_2$, high $Na_2O$ and CaO content, and a high CaO/$P_2O_5$ ratio.

The terms, "biodegradable", "bioerodable", or "resorbable" materials, as used herein, are intended to describe materials that degrade under physiological conditions to form a product that can be metabolized or excreted without damage to the subject. In certain embodiments, the product is metabolized or excreted without permanent damage to the subject. Biodegradable materials may be hydrolytically degradable, may require cellular and/or enzymatic action to fully degrade, or both. Biodegradable materials also include materials that are broken down within cells. Degradation may occur by hydrolysis, oxidation, enzymatic processes, phagocytosis, or other processes.

The term "biocompatible" as used herein, is intended to describe materials that, upon administration in vivo, do not induce undesirable side effects. In some embodiments, the material does not induce irreversible, undesirable side effects. In certain embodiments, a material is biocompatible if it does not induce long term undesirable side effects. In certain embodiments, the risks and benefits of administering a material are weighed in order to determine whether a material is sufficiently biocompatible to be administered to a subject.

The term "biomolecules" as used herein, refers to classes of molecules (e.g., proteins, amino acids, peptides, polynucleotides, nucleotides, carbohydrates, sugars, lipids, nucleoproteins, glycoproteins, lipoproteins, steroids, natural products, etc.) that are commonly found or produced in cells, whether the molecules themselves are naturally-occurring or artificially created (e.g., by synthetic or recombinant methods). For example, biomolecules include, but are not limited to, enzymes, receptors, glycosaminoglycans, neurotransmitters, hormones, cytokines, cell response modifiers such as growth factors and chemotactic factors, antibodies, vaccines, haptens, toxins, interferons, ribozymes, anti-sense agents, plasmids, DNA, and RNA. Exemplary growth factors include but are not limited to bone morphogenic proteins (BMP's) and their active fragments or subunits. In some embodiments, the biomolecule is a growth factor, chemotactic factor, cytokine, extracellular matrix molecule, or a fragment or derivative thereof, for example, a cell attachment sequence such as a peptide containing the sequence, RGD.

The term "carbohydrate" as used herein, refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers The term "composite" as used herein, is used to refer to a unified combination of two or more distinct materials. The composite may be homogeneous or heterogeneous. For example, a composite may be a combination of bone particles and a polymer; or a combination of bone particles, polymers and antibiotics. In certain embodiments, the composite has a particular orientation. In this regard, the terms "putty", "injectable filler", "bone void filler", "moldable composition", and the like, may also be used herein, possibly interchangeably, to refer to various embodiments of composites.

In this regard, in some instances a putty composite is a composite that generally lends itself to being moldable, and that have a relatively higher initial viscosity. Putties can comprise relatively high osteoconductive solid particulate (e.g., osteoconductive matrix) content (particle content) (e.g., >45 wt %-55 wt %). Specific putties can be weight-bearing, and some are weight-bearing at least when initially implanted in a subject. On the other hand, bone void fillers, injectable composites, and the like can refer to composites that are injectable. Bone void fillers can have relatively low osteoconductive solid particulate (e.g., osteoconductive matrix) content (e.g., <45 wt %-55 wt %).

The term "flowable polymer material" as used herein, refers to a flowable composition including one or more of monomers, pre-polymers, oligomers, low molecular weight polymers, uncross-linked polymers, partially cross-linked polymers, partially polymerized polymers, polymers, or combinations thereof that have been rendered formable. One skilled in the art will recognize that a flowable polymer material need not be a polymer but may be polymerizable. In some embodiments, flowable polymer materials include polymers that have been heated past their glass transition or melting point. Alternatively or in addition, a flowable polymer material may include partially polymerized polymer, telechelic polymer, or prepolymer. A pre-polymer is a low molecular weight oligomer typically produced through step growth polymerization. The pre-polymer is formed with an excess of one of the components to produce molecules that are all terminated with the same group. For example, a diol and an excess of a diisocyanate may be polymerized to produce isocyanate terminated prepolymer that may be combined with a diol to form a polyurethane. Alternatively or in addition, a flowable polymer material may be a polymer material/solvent mixture that sets when the solvent is removed.

The terms "modified" and "unmodified", as used herein, refers to whether substances are modified by another substance in any manner. For example, bioactive glass can be modified if its surface is modified by functionalizing the surface of the bioactive glass particles with a modifying substance, such as silane coupling angent 3-aminopropyltriethoxysilane. Similarly, TCP may be modified by functionalizing TCP with a modifying substance, such as polycaprolactone. Thus, the term modified generally refers to substances that are surface functionalized or have additional components relative to the initial unmodified substance.

The term "nontoxic" is used herein to refer to substances which, upon ingestion, inhalation, or absorption through the skin by a human or animal, do not cause, either acutely or chronically, damage to living tissue, impairment of the central nervous system, severe illness or death.

The term "osteoconductive" as used herein, refers to the ability of a substance or material to provide surfaces for osteoblast cells to adhere, proliferate, and/or synthesize new bone. Osteoconductive materials include (but are not limited to): cortical-cancellous bone chips ("CCC"); hydroxyapatite ("HA"); tricalcium phosphate ("TCP"); bioactive glass such as Bioglass 45S5; mixtures of HA/TCP/bioactive glass; other calcium phosphates; calcium carbonate; calcium sulfate; collogen; DBM; other allograft material; and other synthetic allografts. A gathering of one or more types of osteoconductive materials can form an "osteoconductive matrix." Furthermore, some osteoconductive matrix materials and particles can be referred to as "synthetic allograft" and the like.

The term "osteogenic" as used herein, refers to the ability of a substance or material that can induce bone formation.

The term "osteoinductive" as used herein, refers to the quality of being able to recruit cells (e.g., osteoblasts) from the host that have the potential to stimulate new bone formation and induce ectopic bone formation. In general, osteoinductive materials are capable of inducing heterotopic ossification, that is, bone formation in extraskeletal soft tissues (e.g., muscle).

The term "osteoimplant" is used herein in its broadest sense and is not intended to be limited to any particular shapes, sizes, configurations, compositions, or applications. Osteoimplant refers to any device or material for implantation that aids or augments bone formation or healing. Osteoimplants are often applied at a bone defect site, e.g., one resulting from injury, defect brought about during the course of surgery, infection, malignancy, inflammation, or developmental malformation. Osteoimplants can be used in a variety of orthopedic, neurosurgical, dental, and oral and maxillofacial surgical procedures such as the repair of simple and compound fractures and non-unions, external, and internal fixations, joint reconstructions such as arthrodesis, general arthroplasty, deficit filling, disectomy, laminectomy, anterior cerival and thoracic operations, spinal fusions, etc.

The term "osteotherapeutic material" is used herein to refer to a material that promotes bone growth, including, but are not limited to, osteoinductive, osteoconductive, osteogenic and osteopromotive materials. Further, osteotherapeutic materials, or factors, include: bone morphogenic protein ("BMP") such as BMP 2, BMP 4, and BMP 7 (OP1); demineralized bone matrix ("DBM"), platelet-derived growth factor ("PDGF"); insulin-like growth factors I and II; fibroblast growth factors ("FGF's"); transforming growth factor beta ("TGF-beta."); platelet rich plasma (PRP); vescular endothelial growth factor (VEGF); growth hormones; small peptides; genes; stem cells, autologous bone, allogenic bone, bone marrow, biopolymers and bioceramics.

The terms "polynucleotide", "nucleic acid", or "oligonucleotide" as used herein, refer to a polymer of nucleotides. The terms "polynucleotide", "nucleic acid", and "oligonucleotide", may be used interchangeably. Typically, a polynucleotide comprises at least three nucleotides. DNAs and RNAs are exemplary polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thithymidine, inosine, pyrrolo-pyrimidine, 3-methyl adenosine, C5-propynylcytidine, C5-propynyluridine, C5-bromouridine, C5-fluorouridine, C5iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyriboses, arabinose, and hexose), or modified phosphate groups (e.g., phosphorothioates and 5'-N-phosphoramidite linkages). The polymer may also be a short strand of nucleic acids such as RNAi, siRNA, or shRNA.

The terms "polypeptide", "peptide", or "protein" as used herein, include a string of at least three amino acids linked together by peptide bonds. The terms "polypeptide", "peptide", and "protein", may be used interchangeably. In some embodiments, peptides may contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The terms "polysaccharide" or "oligosaccharide" as used herein, refer to any polymer or oligomer of carbohydrate residues. Polymers or oligomers may consist of anywhere from two to hundreds to thousands of sugar units or more. "Oligosaccharide" generally refers to a relatively low molecular weight polymer, while "polysaccharide" typically refers to a higher molecular weight polymer. Polysaccharides may be purified from natural sources such as plants or may be synthesized de novo in the laboratory. Polysaccharides isolated from natural sources may be modified chemically to change their chemical or physical properties (e.g., reduced, oxidized, phosphorylated, cross-linked). Carbohydrate polymers or oligomers may include natural sugars (e.g., glucose, fructose, galactose, mannose, arabinose, ribose, xylose, etc.) and/or modified sugars (e.g., 2'-fluororibose, 2'-deoxyribose, etc.). Polysaccharides may also be either straight or branched. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, poly(dextrose), and fructose. In some embodiments, glycosaminoglycans are considered polysaccharides. Sugar alcohol, as used herein, refers to any polyol such as sorbitol, mannitol, xylitol, galactitol, erythritol, inositol, ribitol, dulcitol, adonitol, arabitol, dithioerythritol, dithiothreitol, glycerol, isomalt, and hydrogenated starch hydrolysates.

The term "porogen" as used herein, refers to a chemical compound that may be part of the inventive composite and upon implantation/injection or prior to implantation/injection diffuses, dissolves, and/or degrades to leave a pore in the osteoimplant composite. A porogen may be introduced into the composite during manufacture, during preparation of the composite (e.g., in the operating room), or after implantation/injection. A porogen essentially reserves space in the composite while the composite is being molded but once the composite is implanted the porogen diffuses, dissolves, or degrades, thereby inducing porosity into the composite. In this way porogens provide latent pores. In certain embodiments, the porogen may be leached out of the composite before implantation/injection. This resulting porosity of the implant generated during manufacture or after implantation/injection (i.e., "latent porosity") is thought to allow infiltration by cells, bone formation, bone remodeling, osteoinduction, osteoconduction, and/or faster degradation of the osteoimplant. A porogen may be a gas (e.g., carbon dioxide, nitrogen, or other inert gas), liquid (e.g., water, biological fluid), or solid. Porogens are typically water soluble such as salts, sugars (e.g., sugar alcohols), polysaccharides (e.g., dextran (poly(dextrose)), water soluble small molecules, etc. Porogens can also be natural or synthetic polymers, oligomers, or monomers that are water soluble or degrade quickly under physiological conditions. Exemplary polymers include polyethylene glycol, poly(vinylpyrollidone), pullulan, poly(glycolide), poly(lactide), poly(lactide-co-glycolide), other polyesters, and starches. In certain embodiments, bone particles utilized in provided composites or compositions may act as porogens. For example, osteoclasts resorb allograft and make pores in composites.

In some embodiments, porogens may refer to a blowing agent (i.e., an agent that participates in a chemical reaction to generate a gas). Water may act as such a blowing agent or porogen.

The term "porosity" as used herein, refers to the average amount of non-solid space contained in a material (e.g., a composite of the present invention). Such space is considered void of volume even if it contains a substance that is liquid at ambient or physiological temperature, e.g., 0.5° C. to 50° C. Porosity or void volume of a composite can be defined as the ratio of the total volume of the pores (i.e., void volume) in the material to the overall volume of composites. In some embodiments, porosity (defined as the volume fraction pores, can be calculated from composite foam density, which can be measured gravimetrically. Porosity may in certain embodiments refer to "latent porosity" wherein pores are only formed upon diffusion, dissolution, or degradation of a material occupying the pores. In such an instance, pores may be formed after implantation/injection. It will be appreciated by these of ordinary skill in the art that the porosity of a provided composite or composition may change over time, in some embodiments, after implantation/injection (e.g., after leaching of a porogen, when osteoclasts resorbing allograft bone, etc.). For the purpose of the present disclosure, implantation/injection may be considered to be "time zero" ($T_0$). In some embodiments, the present invention provides composites and/or compositions having a porosity of at least about 30%, at least about 40%, at least about 50%, at least about 60%, at least about 70%, at least about 80%, at least about 90% or more than 90%, at time zero. In certain embodiments, pre-molded composites and/or compositions may have a porosity of at least about 30%, at least about 40%, at least about 50%, at least about 60%, at least about 70%, at least about 80%, at least about 90% or more than 90%, at time zero. In certain embodiments, injectable composites and/or compositions may have a porosity of as low as 3% at time zero. In certain embodiments, injectable composites and/or compositions may cure in situ and have a porosity of at least about 30%, at least about 40%, at least about 50%, at least about 60%, at least about 70%, at least about 80%, at least about 90% or more than 90% after curing.

The term "remodeling" as used herein, describes the process by which native bone, processed bone allograft, whole bone sections employed as grafts, and/or other bony tissues are replaced with new cell-containing host bone tissue by the action of osteoclasts and osteoblasts. Remodeling also describes the process by which non-bony native tissue and tissue grafts are removed and replaced with new, cell-containing tissue in vivo. Remodeling also describes how inorganic materials (e.g., calcium-phosphate materials, such as β-tricalcium phosphate) is replaced with living bone.

The term "setting time" as used herein, is approximated by the tack-free time (TFT), which is defined as the time at which the material could be touched with a spatula with no adhesion of the spatula to the foam. At the TFT, the wound could be closed without altering the properties of the material.

The term "shaped" as used herein, is intended to characterize a material (e.g., composite) or an osteoimplant refers to a material or osteoimplant of a determined or regular form or configuration in contrast to an indeterminate or vague form or configuration (as in the case of a lump or other solid matrix of special form). Materials may be shaped into any shape, configuration, or size. For example, materials can be shaped as sheets, blocks, plates, disks, cones, pins, screws, tubes, teeth, bones, portions of bones, wedges, cylinders, threaded cylinders, and the like, as well as more complex geometric configurations.

The term "subject", as used herein, refers to a target of administration. The subject of the herein disclosed subject-matter may be any organism, including vertebrates, such as a mammals, fish, birds, reptiles, or amphibian. Thus, the subject of the herein disclosed subject matter may be a human or non human. A subject may be unicellular or multicellular. Veterinary therapeutic uses are provided in accordance with the presently disclosed subject matter. The term "subject" does not denote a particular age or sex. Adult and newborn subjects, as well as fetuses, whether male or female, are intended to be covered.

The term "wet compressive strength" as used herein, refers to the compressive strength of an osteoimplant after being immersed in physiological saline (e.g., phosphate-buffered saline (PBS), water containing 0.9 g NaCl/100 ml water, etc.) for a minimum of 12 hours (e.g., 24 hours). Compressive strength and modulus are well-known measurements of mechanical properties and is measured using the procedure described herein.

The term "working time" as used herein, is defined in the ISO9917 standard as "the period of time, measured from the start of mixing, during which it is possible to manipulate a dental material without an adverse effect on its properties" (Clarkin et al., *J Mater Sci: Mater Med* 2009; 20:1563-1570). In some embodiments, the working time for a two-component polyurethane is determined by the gel point, the time at which the crosslink density of the polymer network is sufficiently high that the material gels and no longer flows. According to the present invention, the working time is measured by loading the syringe with the reactive composite and injecting <0.25 ml every 30s. The working time is noted as the time at which the material was more difficult to inject, indicating a significant change in viscosity.

The term "working time" as used herein, is defined in the ISO9917 standard as "the period of time, measured from the start of mixing, during which it is possible to manipulate a dental material without an adverse effect on its properties" (Clarkin et al., *J Mater Sci: Mater Med* 2009; 20:1563-1570). In some embodiments, the working time for a two-component polyurethane is determined by the gel point, the time at which the crosslink density of the polymer network is sufficiently high that the material gels and no longer flows. According to the present invention, the working time is measured by loading the syringe with the reactive composite and injecting <0.25 ml every 30 s. The working time is noted as the time at which the material was more difficult to inject, indicating a significant change in viscosity.

DESCRIPTION OF EXEMPLARY EMBODIMENTS

Figure 1:
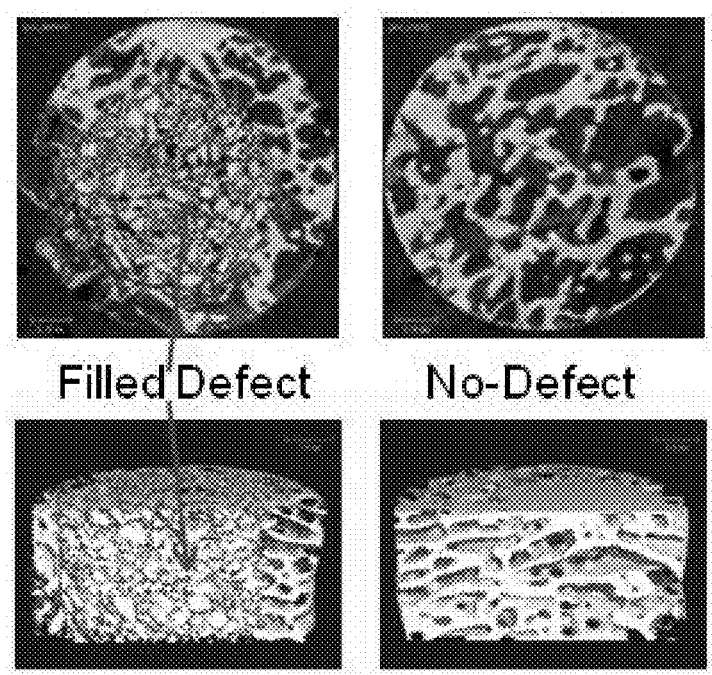
FIG. 1 shows μCT images of an explanted bone core with (left) and without (right) allograft/PUR filling the defect. Top: Cross-sectional slices of the core. Bottom: 'cut-through' 3D renderings. Note that the composite is surrounded by host bone. Bone cores with the filled defect will be tested to determine the compressive strength of the composite after 6 and 12 weeks of remodeling.

The presently-disclosed subject matter includes composites. In some embodiments the composites include polyurethane, an osteoconductive matrix (synthetic allograft), and/or a bioactive agent. In specific embodiments the osteoconductive matrix comprises osteoconductive particles, such as tricalcium phosphate or bioglass particles. Still further, in some embodiments the osteoconductive matrix or the particles that comprise the osteoconductive matrix are surface modified. The bioactive agent provided in some composites can be a growth factor (e.g., osteoinductor), such as recombinant human bone morphogenetic protein 2 (rhBMP-2).

Accordingly, some embodiments relates to a polyurethane composite that comprises possess characteristics of functionally weight-bearing biomaterials. Some embodied composites are two-component polyurethane (PUR) composites that are useful for injectable applications because they can be processed as a reactive liquid that subsequently cures in situ to form a solid composite. Furthermore, the isocyanate groups in the polyurethane of some composites can react with functional groups on the surface of the particles of the osteoconductive matrix to improve interfacial bonding.

Thus, to accomplish the goal of fabricating a weight-bearing biomaterial that actively remodels, embodiments of the invention include compression-molded composites comprising osteoconductive matrix embedded in a two-component PUR component. Embodiments of composites in accordance with the present invention exhibit all five key characteristics of biocompatibility, injectability, weight-bearing properties, rapid cellular infiltration, and sustained release of biologics. Other embodiments are flowable, injectable void fillers that can be used to fill defects, and particularly irregularly shaped bone defects.

Polymer Component

In terms of the polymer component, synthetic polymers can be designed with properties targeted for a given clinical application. According to the present invention, polyurethanes (PUR) are a useful class of biomaterials due to the fact that they can be injectable or moldable as a reactive liquid that subsequently cures to form a porous composite. These materials also have tunable degradation rates, which are shown to be highly dependent on the choice of polyol and isocyanate components (Hafeman et al., *Pharmaceutical Research* 2008; 25(10):2387-99; Storey et al., *J Poly Sci Pt A: Poly Chem* 1994; 32:2345-63; Skarja et al., *J App Poly Sci* 2000; 75:1522-34). Polyurethanes have tunable mechanical properties, which can also be enhanced with the addition of osteoconductive matrix and/or other components (Adhikari et al., *Biomaterials* 2008; 29:3762-70; Goma et al., *J Biomed Mater Res Pt A* 2003; 67A(3):813-27) and exhibit elastomeric rather than brittle mechanical properties.

Polyurethanes can be made by reacting together the components of a two-component composition, one of which includes a polyisocyanate while the other includes a component having two or more hydroxyl groups (i.e., polyols) to react with the polyisocyanate. For example, U.S. Pat. No. 6,306,177, discloses a method for repairing a tissue site using polyurethanes, the content of which is incorporated by reference.

It is to be understood that by "a two-component composition" it means a composition comprising two essential types of polymer components. In some embodiments, such a composition may additionally comprise one or more other optional components.

In some embodiments, polyurethane is a polymer that has been rendered formable through combination of two liquid components (i.e., a polyisocyanate prepolymer and a polyol). In some embodiments, a polyisocyanate prepolymer or a polyol may be a molecule with two or three isocyanate or hydroxyl groups respectively. In some embodiments, a polyisocyanate prepolymer or a polyol may have at least four isocyanate or hydroxyl groups respectively.

Synthesis of porous polyurethane results from a balance of two simultaneous reactions. Reactions, in some embodiments, are illustrated below in Scheme 1. One is a gelling reaction, where an isocyanates and a polyester polyol react to form urethane bonds. The one is a blowing reaction. An isocyanate can react with water to form carbon dioxide gas, which acts as a lowing agent to form pores of polyurethane foam. The relative rates of these reactions determine the scaffold morphology, working time, and setting time.

Exemplary gelling and blowing reactions in forming of polyurethane are shown in Scheme 1 below, where $R_1$, $R_2$ and $R_3$, for example, can be oligomers of caprolactone, lactide and glycolide respectively.

Gelling reaction

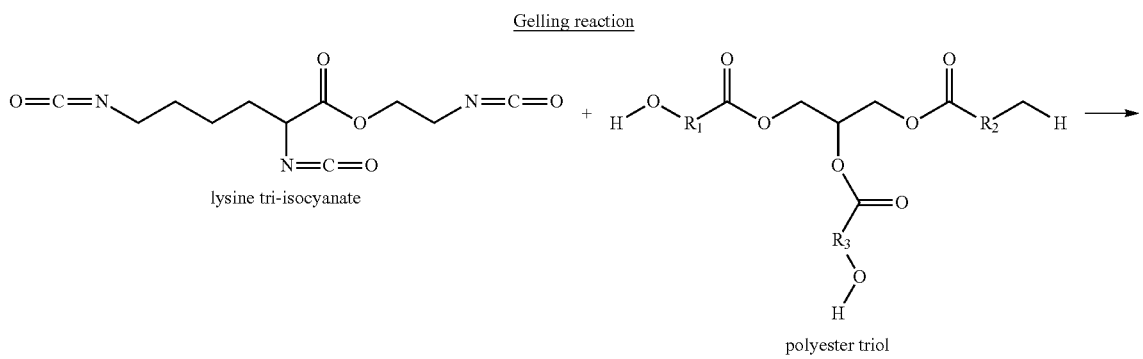

lysine tri-isocyanate polyester triol

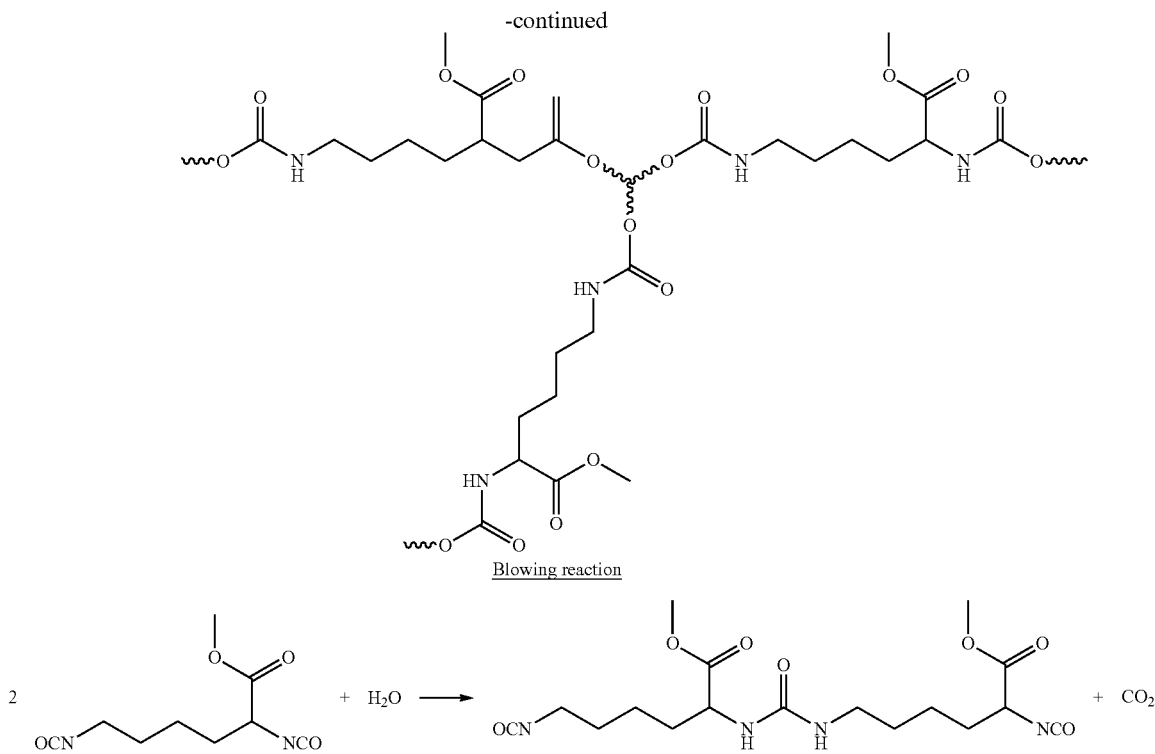

Blowing reaction

Biodegradable polyurethane scaffolds synthesized from aliphatic polyisocyanates been shown to degrade into non-toxic compounds and support cell attachment and proliferation in vitro. A variety of polyurethane polymers suitable for use in the present invention are known in the art, many of which are listed in commonly owned applications: U.S. Ser. No. 10/759,904 filed on Jan. 16, 2004, entitled "Biodegradable polyurethanes and use thereof" and published under No. 2005-0013793; U.S. Ser. No. 11/667,090 filed on Nov. 5, 2005, entitled "Degradable polyurethane foams" and published under No. 2007-0299151; U.S. Ser. No. 12/298,158 filed on Apr. 24, 2006, entitled "Biodegradable polyurethanes" and published under No. 2009-0221784; all of which are incorporated herein by reference. Polyurethanes described in U.S. Ser. No. 11/336,127 filed on Jan. 19, 2006 and published under No. 2006-0216323, which is entitled "Polyurethanes for Osteoimplants" and incorporated herein by reference, may be used in some embodiments of the present invention.

Polyurethanes foams may be prepared by contacting an isocyanate-terminated prepolymer (component 1, e.g, polyisocyanate prepolymer) with a hardener (component 2) that includes at least a polyol (e.g., a polyester polyol) and water, a catalyst and optionally, a stabilizer, a porogen, PEG, etc. In some embodiments, multiple polyurethanes (e.g., different structures, difference molecular weights) may be used in a composite/composition of the present invention. In some embodiments, other biocompatible and/or biodegradable polymers may be used with polyurethanes in accordance with the present invention. In some embodiments, biocompatible co-polymers and/or polymer blends of any combination thereof may be exploited.

Polyurethanes used in accordance with the present invention can be adjusted to produce polymers having various physiochemical properties and morphologies including, for example, flexible foams, rigid foams, elastomers, coatings, adhesives, and sealants. The properties of polyurethanes are controlled by choice of the raw materials and their relative concentrations. For example, thermoplastic elastomers are characterized by a low degree of cross-linking and are typically segmented polymers, consisting of alternating hard (diisocyanates and chain extenders) and soft (polyols) segments. Thermoplastic elastomers are formed from the reaction of diisocyanates with long-chain diols and short-chain diol or diamine chain extenders. In some embodiments, pores in bone/polyurethanes composites in the present invention are interconnected and have a diameter ranging from approximately 50 to approximately 1000 microns.

Prepolymer. Polyurethane prepolymers can be prepared by contacting a polyol with an excess (typically a large excess) of a polyisocyanate. The resulting prepolymer intermediate includes an adduct of polyisocyanates and polyols solubilized in an excess of polyisocyanates. Prepolymer can, in some embodiments, be formed by using an approximately stoichiometric amount of polyisocyanates in forming a prepolymer and subsequently adding additional polyisocyanates. The prepolymer therefore exhibits both low viscosity, which facilitates processing, and improved miscibility as a result of the polyisocyanate-polyol adduct. Polyurethane networks can, for example, then be prepared by reactive liquid molding, wherein the prepolymer is contacted with a polyester polyol to form a reactive liquid mixture (i.e., a two-component composition) which is then cast into a mold and cured.

Polyisocyanates or multi-isocyanate compounds for use in the present invention include aliphatic polyisocyanates. Exemplary aliphatic polyisocyanates include, but are not limited to, lysine diisocyanate, an alkyl ester of lysine diisocyanate (for example, the methyl ester or the ethyl ester), lysine triisocyanate, hexamethylene diisocyanate, isophorone diisocyanate (IPDI), 4,4'-dicyclohexylmethane diisocyanate ($H_{12}$MDI), cyclohexyl diisocyanate, 2,2,4-(2, 2,4)-trimethylhexamethylene diisocyanate (TMDI), dimers prepared form aliphatic polyisocyanates, trimers prepared from aliphatic polyisocyanates and/or mixtures thereof. In some embodiments, hexamethylene diisocyanate (HDI) trimer sold as Desmodur N3300A may be a polyisocyanate utilized in the present invention. In some embodiments, polyisocyanates used in the present invention includes approximately 10 to 55% NCO by weight (wt % NCO=100*(42/Mw)). In some embodiments, polyisocyanates include approximately 15 to 50% NCO.

Polyisocyanate prepolymers provide an additional degree of control over the structure of biodegradable polyurethanes. Prepared by reacting polyols with isocyanates, NCO-terminated prepolymers are oligomeric intermediates with isocyanate functionality as shown in Scheme 1. To increase reaction rates, urethane catalysts (e.g., tertiary amines) and/or elevated temperatures (60-90° C.) may be used (see, Guelcher, *Tissue Engineering: Part B*, 14 (1) 2008, pp 3-17).

Polyols used to react with polyisocyanates in preparation of NCO-terminated prepolymers refer to molecules having at least two functional groups to react with isocyanate groups. In some embodiments, polyols have a molecular weight of no more than 1000 g/mol. In some embodiments, polyols have a rang of molecular weight between about 100 g/mol to about 500 g/mol. In some embodiments, polyols have a rang of molecular weight between about 200 g/mol to about 400 g/mol. In certain embodiments, polyols (e.g., PEG) have a molecular weight of about 200 g/mol. Exemplary polyols include, but are not limited to, PEG, glycerol, pentaerythritol, dipentaerythritol, tripentaerythritol, 1,2,4-butanetriol, trimethylolpropane, 1,2,3-trihydroxyhexane, myo-inositol, ascorbic acid, a saccharide, or sugar alcohols (e.g., mannitol, xylitol, sorbitol etc.). In some embodiments, polyols may comprise multiple chemical entities having reactive hydrogen functional groups (e.g., hydroxy groups, primary amine groups and/or secondary amine groups) to react with the isocyanate functionality of polyisocyanates.

In some embodiments, polyisocyanate prepolymers are resorbable. Zhang and coworkers synthesized biodegradable lysine diisocyanate ethyl ester (LDI)/glucose polyurethane foams proposed for tissue engineering applications. In those studies, NCO-terminated prepolymers were prepared from LDI and glucose. The prepolymers were chain-extended with water to yield biocompatible foams which supported the growth of rabbit bone marrow stromal cells in vitro and were non-immunogenic in vivo. (see Zhang, et al., *Biomaterials* 21: 1247-1258 (2000), and Zhang, et al., *Tiss. Eng.*, 8(5): 771-785 (2002), both of which are incorporated herein by reference).

In some embodiments, prepared polyisocyanate prepolymer can be a flowable liquid at processing conditions. In general, the processing temperature is no greater than 60° C. In some embodiments, the processing temperature is ambient temperature (25° C.).

In some embodiments the ratio of polyisocyanate to polyol can be adjusted to modify different characteristics of the prepolymer, including its reactivity, viscosity, or the like. In this regard, some embodiments of prepolymers comprise a 2:1 molar ratio of polyisocyanate to polyol. In other embodiments the molar ratio of polyisocyanate to polyol is about 1.5:1, about 1.6:1, about 1.7:1, about 1.8:1, about 1.9:1, about 2.0:1, about 2.1:1, about 2.2:1, about 2.3:1, about 2.4:1, about 2.5:1, about 2.6:1, about 2.7:1, about 2.8:1, about 2.9:1, or about 3.0:1.

In this regard, the viscosity of the prepolymer can also vary depending on different factors. In some embodiments the viscosity of the prepolymer will vary depending on the molar ratio of polyisocyanate to polyol that is used. The viscosity can be tuned so that the composite has desirable workable characteristics (e.g., injectable, putty, etc.), among other things. In some embodiments the viscosity of the prepolymer can be about 10,000 cSt, about 11,000 cSt, about 12,000 cSt, about 13,000 cSt, about 14,000 cSt, about 15,000 cSt, about 16,000 cSt, about 17,000 cSt, about 18,000 cSt, about 19,000 cSt, about 20,000 cSt, about 21,000 cSt, about 22,000 cSt, about 23,000 cSt, about 24,000 cSt, about 25,000 cSt, about 26,000 cSt, about 27,000 cSt, about 28,000 cSt, about 29,000 cSt, or about 30,000 cSt.

Polyols. Polyols utilized in accordance with the present invention can be amine- and/or hydroxyl-terminated compounds and include, but are not limited to, polyether polyols (such as polyethylene glycol (PEG or PEO), polytetramethylene etherglycol (PTMEG), polypropylene oxide glycol (PPO)); amine-terminated polyethers; polyester polyols (such as polybutylene adipate, caprolactone polyesters, castor oil); and polycarbonates (such as poly(1,6-hexanediol) carbonate). In some embodiments, polyols may be (1) molecules having multiple hydroxyl or amine functionality, such as glucose, polysaccharides, and castor oil; and (2) molecules (such as fatty acids, triglycerides, and phospholipids) that have been hydroxylated by known chemical synthesis techniques to yield polyols.

Polyols used in the present invention may be polyester polyols. In some embodiments, polyester polyols may include polyalkylene glycol esters or polyesters prepared from cyclic esters. In some embodiments, polyester polyols may include poly(ethylene adipate), poly(ethylene glutarate), poly(ethylene azelate), poly(trimethylene glutarate), poly(pentamethylene glutarate), poly(diethylene glutarate), poly(diethylene adipate), poly(triethylene adipate), poly(1,2-propylene adipate), mixtures thereof, and/or copolymers thereof. In some embodiments, polyester polyols can include, polyesters prepared from caprolactone, glycolide, D, L-lactide, mixtures thereof, and/or copolymers thereof. In some embodiments, polyester polyols can, for example, include polyesters prepared from castor-oil. When polyurethanes degrade, their degradation products can be the polyols from which they were prepared from.

In some embodiments, polyester polyols can be miscible with prepared prepolymers used in reactive liquid mixtures (i.e., two-component composition) of the present invention. In some embodiments, surfactants or other additives may be included in the reactive liquid mixtures to help homogenous mixing.

The glass transition temperature (Tg) of polyester polyols used in the reactive liquids to form polyurethanes can be less than 60° C., less than 37° C. (approximately human body temperature) or even less than 25° C. In addition to affecting flowability at processing conditions, Tg can also affect degradation. In general, a Tg of greater than approximately 37° C. will result in slower degradation within the body, while a Tg below approximately 37° C. will result in faster degradation.

Molecular weight of polyester polyols used in the reactive liquids to form polyurethanes can, for example, be adjusted to control the mechanical properties of polyurethanes utilized in accordance with the present invention. In that regard, using polyester polyols of higher molecular weight results in greater compliance or elasticity. In some embodiments, polyester polyols used in the reactive liquids may have a molecular weight less than approximately 3000 Da. In certain embodiments, the molecular weight may be in the range of approximately 200 to 2500 Da or 300 to 2000 Da.

In some embodiments, the molecular weight may be approximately in the range of approximately 450 to 1800 Da or 450 to 1200 Da.

In some embodiments, a polyester polyol comprise poly(caprolactone-co-lactide-co-glycolide), which has a molecular weight in a range of 200 Da to 2500 Da, or 300 Da to 2000 Da.

In some embodiments, polyols may include multiply types of polyols with different structures, molecular weight, properties, etc.

Additional Components. In accordance with the present invention, two-component compositions (i.e., polyprepolymers and polyols) to form porous composites may be used with other agents and/or catalysts. Zhang et al. have found that water may be an adequate blowing agent for a lysine diisocyanate/PEG/glycerol polyurethane (see Zhang, et al., *Tissue Eng.* 2003 (6):1143-57) and may also be used to form porous structures in polyurethanes. Other blowing agents include dry ice or other agents that release carbon dioxide or other gases into the composite. Alternatively, or in addition, porogens (see detail discussion below) such as salts may be mixed in with reagents and then dissolved after polymerization to leave behind small voids.

Two-component compositions and/or the prepared composites used in the present invention may include one or more additional components. In some embodiments, inventive compositions and/or composites may include, water, a catalyst (e.g., gelling catalyst, blowing catalyst, etc.), a stabilizer, a plasticizer, a porogen, a chain extender (for making of polyurethanes), a pore opener (such as calcium stearate, to control pore morphology), a wetting or lubricating agent, etc. (See, U.S. Ser. No. 10/759,904 published under No. 2005-0013793, and U.S. Ser. No. 11/625,119 published under No. 2007-0191963; both of which are incorporated herein by reference).

In some embodiments, inventive compositions and/or composites may include and/or be combined with a solid filler (e.g., carboxymethylcellulose (CMC) and hyaluronic acid (HA)). For example, when composites used in wound healing, solid fillers can help absorb excess moisture in the wounds from blood and serum and allow for proper foaming.

In certain embodiments, additional biocompatible polymers (e.g., PEG) or co-polymers can be used with compositions and composites in the present invention.

Water. Water may be a blowing agent to generate porous polyurethane-based composites. Porosity of bone/polymer composites increased with increasing water content, and biodegradation rate accelerated with decreasing polyester half-life, thereby yielding a family of materials with tunable properties that are usefull in the present invention. See, Guelcher et al., Tissue Engineering, 13(9), 2007, pp 2321-2333, which is incorporated by reference.

In some embodiments, an amount of water is about 0.5, 1, 1.5, 2, 3, 4 5, 6, 7, 8, 9, 10 parts per hundred parts (pphp) polyol. In some embodiments, water has an approximate rang of any of such amounts.

Catalyst. In some embodiments, at least one catalyst is added to form reactive liquid mixture (i.e., two-component compositions). A catalyst, for example, can be non-toxic (in a concentration that may remain in the polymer).

A catalyst can, for example, be present in two-component compositions in a concentration in the range of approximately 0.5 to 5 parts per hundred parts polyol (pphp) and, for example, in the range of approximately 0.5 to 2, or 2 to 3 pphp. A catalyst can, for example, be an amine compound. In some embodiments, catalyst may be an organometallic compound or a tertiary amine compound. In some embodiments the catalyst may be stannous octoate (an organobismuth compound), triethylene diamine, bis(dimethylaminoethyl)ether, dimethylethanolamine, dibutyltin dilaurate, and Coscat organometallic catalysts manufactured by Vertullus (a bismuth based catalyst), or any combination thereof.

Stabilizer. In some embodiments, a stabilizer is nontoxic (in a concentration remaining in the polyurethane foam) and can include a non-ionic surfactant, an anionic surfactant or combinations thereof. For example, a stabilizer can be a polyethersiloxane, a salt of a fatty sulfonic acid or a salt of a fatty acid. In certain embodiments, a stabilizer is a polyethersiloxane, and the concentration of polyethersiloxane in a reactive liquid mixture can, for example, be in the range of approximately 0.25 to 4 parts per hundred polyol. In some embodiments, polyethersiloxane stabilizer are hydrolyzable.

In some embodiments, the stabilizer can be a salt of a fatty sulfonic acid. Concentration of a salt of the fatty sulfonic acid in a reactive liquid mixture can be in the range of approximately 0.5 to 5 parts per hundred polyol. Examples of suitable stabilizers include a sulfated castor oil or sodium ricinoleicsulfonate.

Stabilizers can be added to a reactive liquid mixture of the present invention to, for example, disperse prepolymers, polyols and other additional components, stabilize the rising carbon dioxide bubbles, and/or control pore sizes of inventive composites. Although there has been a great deal of study of stabilizers, the operation of stabilizers during foaming is not completely understood. Without limitation to any mechanism of operation, it is believed that stabilizers preserve the thermodynamically unstable state of a polyurethane foam during the time of rising by surface forces until the foam is hardened. In that regard, foam stabilizers lower the surface tension of the mixture of starting materials and operate as emulsifiers for the system. Stabilizers, catalysts and other polyurethane reaction components are discussed, for example, in Oertel, Günter, ed., *Polyurethane Handbook*, Hanser Gardner Publications, Inc. Cincinnati, Ohio, 99-108 (1994). A specific effect of stabilizers is believed to be the formation of surfactant monolayers at the interface of higher viscosity of bulk phase, thereby increasing the elasticity of surface and stabilizing expanding foam bubbles.

Chain Extender. To prepare high-molecular-weight polymers, prepolymers are chain extended by adding a short-chain (e.g., <500 g/mol) polyamine or polyol. In certain embodiments, water may act as a chain extender. In some embodiments, addition of chain extenders with a functionality of two (e.g., diols and diamines) yields linear alternating block copolymers.

Plasticizer. In some embodiments, inventive compositions and/or composites include one or more plasticizers. Plasticizers are typically compounds added to polymers or plastics to soften them or make them more pliable. According to the present invention, plasticizers soften, make workable, or otherwise improve the handling properties of polymers or composites. Plasticizers also allow inventive composites to be moldable at a lower temperature, thereby avoiding heat induced tissue necrosis during implantation. Plasticizer may evaporate or otherwise diffuse out of the composite over time, thereby allowing composites to harden or set. Without being bound to any theory, plasticizer are thought to work by embedding themselves between the chains of polymers. This forces polymer chains apart and thus lowers the glass transition temperature of polymers. In general, the more plasticizer added, the more flexible the resulting polymers or composites will be.

In some embodiments, plasticizers are based on an ester of a polycarboxylic acid with linear or branched aliphatic alcohols of moderate chain length. For example, some plasticizers are adipate-based. Examples of adipate-based plasticizers include bis(2-ethylhexyl)adipate (DOA), dimethyl adipate (DMAD), monomethyl adipate (MMAD), and dioctyl adipate (DOA). Other plasticizers are based on maleates, sebacates, or citrates such as bibutyl maleate (DBM), diisobutylmaleate (DIBM), dibutyl sebacate (DBS), triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC), and trimethylcitrate (TMC). Other plasticizers are phthalate based. Examples of phthalate-based plasticizers are N-methyl phthalate, bis(2-ethylhexyl) phthalate (DEHP), diisononyl phthalate (DINP), bis(n-butyl) phthalate (DBP), butyl benzyl phthalate (BBzP), diisodecyl phthalate (DOP), diethyl phthalate (DEP), diisobutyl phthalate (DIBP), and di-n-hexyl phthalate. Other suitable plasticizers include liquid polyhydroxy compounds such as glycerol, polyethylene glycol (PEG), triethylene glycol, sorbitol, monacetin, diacetin, and mixtures thereof. Other plasticizers include trimellitates (e.g., trimethyl trimellitate (TMTM), tri-(2-ethylhexyl)trimellitate (TEHTM-MG), tri-(n-octyl,n-decyl)trimellitate (ATM), tri-(heptyl,nonyl)trimellitate (LTM), n-octyl trimellitate (OTM)), benzoates, epoxidized vegetable oils, sulfonamides (e.g., N-ethyl toluene sulfonamide (ETSA), N-(2-hydroxypropyl)benzene sulfonamide (HP BSA), N-(n-butyl) butyl sulfonamide (BBSA-NBBS)), organophosphates (e.g., tricresyl phosphate (TCP), tributyl phosphate (TBP)), glycols/polyethers (e.g., triethylene glycol dihexanoate, tetraethylene glycol diheptanoate), and polymeric plasticizers. Other plasticizers are described in *Handbook of Plasticizers* (G. Wypych, Ed., ChemTec Publishing, 2004), which is incorporated herein by reference. In certain embodiments, other polymers are added to the composite as plasticizers. In certain particular embodiments, polymers with the same chemical structure as those used in the composite are used but with lower molecular weights to soften the overall composite. In other embodiments, different polymers with lower melting points and/or lower viscosities than those of the polymer component of the composite are used.

In some embodiments, polymers used as plasticizer are poly(ethylene glycol) (PEG). PEG used as a plasticizer is typically a low molecular weight PEG such as those having an average molecular weight of 1000 to 10000 g/mol, for example, from 4000 to 8000 g/mol. In certain embodiments, PEG 4000, PEG 5000, PEG 6000, PEG 7000, PEG 8000 or combinations thereof are used in inventive composites. For example, plasticizer (PEG) is useful in making more moldable composites that include poly(lactide), poly(D,L-lactide), poly(lactide-co-glycolide), poly(D,L-lactide-co-glycolide), or poly(caprolactone). Plasticizer may comprise 1-40% of inventive composites by weight. In some embodiments, the plasticizer is 10-30% by weight. In some embodiments, the plasticizer is approximately 10%, 15%, 20%, 25%, 30% or 40% by weight. In other embodiments, a plasticizer is not used in the composite. For example, in some polycaprolactone-containing composites, a plasticizer is not used.

In some embodiments, inert plasticizers may be used. In some embodiments, a plasticizer may not be used in the present invention.

Porogen. Porosity of inventive composites may be accomplished using any means known in the art. Exemplary methods of creating porosity in a composite include, but are not limited to, particular leaching processes, gas foaming processing, supercritical carbon dioxide processing, sintering, phase transformation, freeze-drying, cross-linking, molding, porogen melting, polymerization, melt-blowing, and salt fusion (Murphy et al., *Tissue Engineering* 8(1):43-52, 2002; incorporated herein by reference). For a review, see Karageorgiou et al., *Biomaterials* 26:5474-5491, 2005; incorporated herein by reference. Porosity may be a feature of inventive composites during manufacture or before implantation, or porosity may only be available after implantation. For example, a implanted composite may include latent pores. These latent pores may arise from including porogens in the composite.

Porogens may be any chemical compound that will reserve a space within the composite while the composite is being molded and will diffuse, dissolve, and/or degrade prior to or after implantation or injection leaving a pore in the composite. Porogens may have the property of not being appreciably changed in shape and/or size during the procedure to make the composite moldable. For example, a porogen should retain its shape during the heating of the composite to make it moldable. Therefore, a porogen does not melt upon heating of the composite to make it moldable. In certain embodiments, a porogen has a melting point greater than about 60° C., greater than about 70° C., greater than about 80° C., greater than about 85° C., or greater than about 90° C.

Porogens may be of any shape or size. A porogen may be spheroidal, cuboidal, rectangular, elonganted, tubular, fibrous, disc-shaped, platelet-shaped, polygonal, etc. In certain embodiments, the porogen is granular with a diameter ranging from approximately 100 microns to approximately 800 microns. In certain embodiments, a porogen is elongated, tubular, or fibrous. Such porogens provide increased connectivity of pores of inventive composite and/or also allow for a lesser percentage of the porogen in the composite.

Amount of porogens may vary in inventive composite from 1% to 80% by weight. In certain embodiments, the plasticizer makes up from about 5% to about 80% by weight of the composite. In certain embodiments, a plasticizer makes up from about 10% to about 50% by weight of the composite. Pores in inventive composites are thought to improve the osteoinductivity or osteoconductivity of the composite by providing holes for cells such as osteoblasts, osteoclasts, fibroblasts, cells of the osteoblast lineage, stem cells, etc. Pores provide inventive composites with biological in growth capacity. Pores may also provide for easier degradation of inventive composites as bone is formed and/or remodeled. In some embodiments, a porogen is biocompatible.

A porogen may be a gas, liquid, or solid. Exemplary gases that may act as porogens include carbon dioxide, nitrogen, argon, or air. Exemplary liquids include water, organic solvents, or biological fluids (e.g., blood, lymph, plasma). Gaseous or liquid porogen may diffuse out of the osteoimplant before or after implantation thereby providing pores for biological in-growth. Solid porogens may be crystalline or amorphous. Examples of possible solid porogens include water soluble compounds. Exemplary porogens include carbohydrates (e.g., sorbitol, dextran (poly(dextrose)), starch), salts, sugar alcohols, natural polymers, synthetic polymers, and small molecules.

In some embodiments, carbohydrates are used as porogens in inventive composites. A carbohydrate may be a monosaccharide, disaccharide, or polysaccharide. The carbohydrate may be a natural or synthetic carbohydrate. In some embodiments, the carbohydrate is a biocompatible, biodegradable carbohydrate. In certain embodiments, the carbohydrate is a polysaccharide. Exemplary polysaccharides include cellulose, starch, amylose, dextran, poly(dextrose), glycogen, etc.

In certain embodiments, a polysaccharide is dextran. Very high molecular weight dextran has been found particularly useful as a porogen. For example, the molecular weight of the dextran may range from about 500,000 g/mol to about 10,000,000 g/mol, preferably from about 1,000,000 g/mol to about 3,000,000 g/mol. In certain embodiments, the dextran has a molecular weight of approximately 2,000,000 g/mol. Dextrans with a molecular weight higher than 10,000,000 g/mol may also be used as porogens. Dextran may be used in any form (e.g., particles, granules, fibers, elongated fibers) as a porogen. In certain embodiments, fibers or elongated fibers of dextran are used as a porogen in inventive composites. Fibers of dextran may be formed using any known method including extrusion and precipitation. Fibers may be prepared by precipitation by adding an aqueous solution of dextran (e.g., 5-25% dextran) to a less polar solvent such as a 90-100% alcohol (e.g., ethanol) solution. The dextran precipitates out in fibers that are particularly useful as porogens in the inventive composite. Once the composite with dextran as a porogen is implanted into a subject, the dextran dissolves away very quickly. Within approximately 24 hours, substantially all of dextran is out of composites leaving behind pores in the osteoimplant composite. An advantage of using dextran in a composite is that dextran exhibits a hemostatic property in extravascular space. Therefore, dextran in a composite can decrease bleeding at or near the site of implantation.

Small molecules including pharmaceutical agents may also be used as porogens in the inventive composites. Examples of polymers that may be used as plasticizers include poly(vinyl pyrollidone), pullulan, poly(glycolide), poly(lactide), and poly(lactide-co-glycolide). Typically low molecular weight polymers are used as porogens. In certain embodiments, a porogen is poly(vinyl pyrrolidone) or a derivative thereof. Plasticizers that are removed faster than the surrounding composite can also be considered porogens.

Osteoconductive Matrix

In addition to a polyurethane component, the presently-disclosed composites can further comprise an osteoconductive matrix. In some embodiments, the osteoconductive matrix can be a particulate material, inorganic material, synthetic materials including synthetic allografts, bone allografts, or combinations thereof. The elements that make up an osteoconductive matrix may not always be mutually exclusive. The terms "osteoconductive matrix," "osteoconductive particles," "synthetic allograft" and the like are used interchangeably with respect to certain materials.

The osteoconductive matrix may comprise particulate materials. These materials may be any type of additional components comprising inorganic materials and/or other bone substitute materials (i.e., compositions similar to natural bone such as collagen, biocompatible polymers, osteoinductive agents, other commercial bone graft products, any composite graft, etc.), may be utilized in the present invention. Inorganic materials, including but not limited to, calcium phosphate materials, and other bone substitute materials, may also be exploited for use as particulate inclusions in the inventive composites. Exemplary materials utilized in accordance with the present invention include aragonite, dahlite, calcite, amorphous calcium carbonate, vaterite, weddellite, whewellite, struvite, urate, ferrihydrite, francolite, monohydrocalcite, magnetite, goethite, dentin, calcium carbonate, calcium sulfate, calcium phosphosilicate, sodium phosphate, calcium aluminate, calcium phosphate, hydroxyapatite, α-tricalcium phosphate, dicalcium phosphate, β-tricalcium phosphate, tetracalcium phosphate, amorphous calcium phosphate, octacalcium phosphate, and bioactive glass (bioglass) (e.g., 45S5 bioglass, Mo-Sci Corporation, Rolla, Mo.). Substituted calcium phosphate phases are also contemplated for use with the invention, including but not limited to fluorapatite, chlorapatite, magnesium-substituted tricalcium phosphate, and carbonate hydroxyapatite. In certain embodiments, the inorganic material is a substituted form of hydroxyapatite. For example, hydroxyapatite may be substituted with other ions such as fluoride, chloride, magnesium, sodium, potassium, and groups such as silicates, silicon dioxides, carbonates, etc. Additional calcium phosphate phases suitable for use with the invention include those disclosed in U.S. Pat. Nos. RE 33,161 and RE 33,221 to Brown et al.; U.S. Pat. Nos. 4,880,610; 5,034,059; 5,047,031; 5,053,212; 5,129,905; 5,336,264; and 6,002,065 to Constantz et al.; U.S. Pat. Nos. 5,149,368; 5,262,166 and 5,462,722 to Liu et al.; U.S. Pat. Nos. 5,525,148 and 5,542,973 to Chow et al., U.S. Pat Nos. 5,717,006 and 6,001,394 to Daculsi et al., U.S. Pat. No. 5,605,713 to Boltong et al., U.S. Pat. No. 5,650,176 to Lee et al., and U.S. Pat. No. 6,206,957 to Driessens et al, and biologically-derived or biomimetic materials such as those identified in Lowenstam H A, Weiner S, *On Biomineralization*, Oxford University Press, 1989; each of which is incorporated herein by reference.

In some embodiments, particles that comprise the osteoconductive matrix have a medium or mean diameter about 1200 microns, 1100 microns, 1000 microns, 900 microns, 800 microns, 700 microns, 600 microns, 500 microns, 400 microns, 300 microns, 200 microns, 100 microns, etc. In some embodiments, diameters of the particles are within a range between any of such sizes. For example, medium or mean diameters of particles have a range from approximately 100 microns to approximately 1000 microns.

In this regard, without being bound by theory or mechanism, it has been found that remodeling proceeds from the external surface to the interior through the process of creeping substitution, and limited remodeling of current allograft devices is conjectured to be due in part to their low specific surface area. Embodiments including osteoconductive matrix (e.g., particles of a size of 100-500 µm) in a porous polymer component can increase the rate of remodeling by increasing the specific surface area. In certain embodiments, particle sizes less than 100 µm do not result in optimal remodeling, and particularly so for particles smaller than 50 µm. Without being bound by theory or mechanism, this is believed to be due to the fact that osteoclasts are unable to efficiently recognize particles smaller than 100 µm, and therefore these relatively small particles may cause an inflammatory response. Particles larger than about 500 µm also can result in less than optimal remodeling for embodiments of the present invention.

As for irregularly shaped particles, recited dimension ranges may represent the length of the greatest or smallest dimension of the particle. As examples, particles can be disk shaped or pin shaped, with tapered ends having an average diameter of from about 100 microns to about 500 microns. As will be appreciated by one of skill in the art, for injectable composites, the maximum particle size will depend in part on the size of the cannula or needle through which the material will be delivered.

Processing of osteoconductive matrix to particles may be adjusted to optimize for the desired size and/or distribution of particles. The properties of resulting inventive composites (e.g., mechanical properties) may also be engineered by adjusting weight percent, shapes, sizes, distribution, etc. of particles that comprise an osteoconductive matrix. For example, an inventive composite may be made more viscous and load bearing by including a higher percentage of particles.

Additional embodiments comprise PUR composites that include combinations of synthetic allograft (e.g., synthetic allograft) and bone allograft. These embodiments may comprise similar total allograft content as the strictly synthetic or bone allograft embodiments, but the ratio of allograft to synthetic allograft may be varied to any extent. For instance, PUR composites may comprise bone allograft and synthetic allograft in a ratio of 1:99 to a ratio of 99:1. Thus, embodiments may comprise mixtures of synthetic and non-synthetic allograft to meet the limitations of a particular circumstance.

Surface Modification. Osteoconductive matrix utilized in accordance with the present invention may be optionally treated to enhance their interaction with polyurethanes and/or to confer other properties to osteoconductive matrix. Surface modification may provide a chemical substance that is strongly bonded to the surface of particles that comprise an osteoconductive matrix, e.g., covalently bonded to the surface. Particles may, alternatively or additionally, be coated with a material to facilitate interaction with polymers of inventive composites.

In some embodiments, silane coupling agents are used to surface modify particles that make the osteoconductive matrix. Silane has at least two sections, a set of leaving groups and at least an active group. An active group may be connected to the silicon atom in the silane by an elongated tether group. An exemplary silane coupling agent is 3-trimethoxysilylpropylmethacrylate, available from Union Carbide. Three methoxy groups are leaving groups, and the methacrylate active group is connected to the silicon atom by a propyl tether group. In some embodiments, a leaving group is an alkoxy group such as methoxy or ethoxy. Depending on the solvent used to link the coupling agent to osteoconductive matrix, hydrogen or alkyl groups such as methyl or ethyl may serve as leaving groups. The length of tethers determines the intimacy of connection between polymers and osteoconductive matrix particles.

An exemplary list of silanes that may be used with the present invention is provided in U.S. Patent Publication No. 2004/0146543, the contents of which are incorporated herein by reference. Silanes are available from companies such as Union Carbide, AP Resources Co. (Seoul, South Korea), and BASF.

The active group of silanes may be incorporated directly into polymers or may be used to attach a second chemical group to osteoconductive matrix. For example, if a particular monomer polymerizes through a functional group that is not commercially available as a silane, the monomer may be attached to the active group.

Osteoconductive matrix can also be surface-modified with polyester polymers. The polyester polymers may be any recognized by those of ordinary skill in the art as being biodegradable and suitable for use in composites, and include any of the polyester polymers described herein. In specific embodiments the polyester polymers include polycaprolactone.

Still further, in some embodiments the osteoconductive matrix is surface-modified by two or more different molecules. For instance, in some embodiments the particles that comprise the osteoconductive matrix are first surface-modified with a silane, and then a polyester polymer is coupled to the silane that is bound to the osteoconductive particles.

Components to Deliver

Alternatively or additionally, composites of the present invention may have one or more components to deliver when implanted, including biomolecules, small molecules, bioactive agents, etc., to promote bone growth and connective tissue regeneration, and/or to accelerate healing. Examples of materials that can be incorporated include chemotactic factors, angiogenic factors, bone cell inducers and stimulators, including the general class of cytokines such as the TGF-β superfamily of bone growth factors, the family of bone morphogenic proteins, osteoinductors, and/or bone marrow or bone forming precursor cells, isolated using standard techniques. Sources and amounts of such materials that can be included are known to those skilled in the art.

Biologically active materials, comprising biomolecules, small molecules, and bioactive agents may also be included in inventive composites to, for example, stimulate particular metabolic functions, recruit cells, or reduce inflammation. For example, nucleic acid vectors, including plasmids and viral vectors, that will be introduced into the patient's cells and cause the production of growth factors such as bone morphogenetic proteins may be included in a composite. Biologically active agents include, but are not limited to, antiviral agent, antimicrobial agent, antibiotic agent, amino acid, peptide, protein, glycoprotein, lipoprotein, antibody, steroidal compound, antibiotic, antimycotic, cytokine, vitamin, carbohydrate, lipid, extracellular matrix, extracellular matrix component, chemotherapeutic agent, cytotoxic agent, growth factor, anti-rejection agent, analgesic, anti-inflammatory agent, viral vector, protein synthesis co-factor, hormone, endocrine tissue, synthesizer, enzyme, polymer-cell scaffolding agent with parenchymal cells, angiogenic drug, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, hydroxyapatite, and penetraction enhancer. Additional exemplary substances include chemotactic factors, angiogenic factors, analgesics, antibiotics, anti-inflammatory agents, bone morphogenic proteins, and other growth factors that promote cell-directed degradation or remodeling of the polymer phase of the composite and/or development of new tissue (e.g., bone). RNAi or other technologies may also be used to reduce the production of various factors.

In some embodiments, inventive composites include antibiotics. Antibiotics may be bacteriocidial or bacteriostatic. An anti-microbial agent may be included in composites. For example, anti-viral agents, anti-protazoal agents, anti-parasitic agents, etc. may be include in composites. Other suitable biostatic/biocidal agents include antibiotics, povidone, sugars, and mixtures thereof. Exemplary antibiotics include, but not limit to, Amikacin, Gentamicin, Kanamycin, Neomycin, Netilmicin, Streptomycin, Tobramycin, Paromomycin, Geldanamycin, Herbimycin, Loravabef, etc. (See, *The Merck Manual of Medical Information—Home Edition*, 1999).

Inventive composites may also be seeded with cells. In some embodiments, a patient's own cells are obtained and used in inventive composites. Certain types of cells (e.g., osteoblasts, fibroblasts, stem cells, cells of the osteoblast lineage, etc.) may be selected for use in the composite. Cells may be harvested from marrow, blood, fat, bone, muscle, connective tissue, skin, or other tissues or organs. In some embodiments, a patient's own cells may be harvested, optionally selected, expanded, and used in the inventive composite. In other embodiments, a patient's cells may be harvested, selected without expansion, and used in the inventive composite. Alternatively, exogenous cells may be employed. Exemplary cells for use with the invention include mesenchymal stem cells and connective tissue cells, including osteoblasts, osteoclasts, fibroblasts, preosteoblasts, and partially differentiated cells of the osteoblast lineage. Cells may be genetically engineered. For example, cells may be engineered to produce a bone morphogenic protein.

In some embodiments the composite further comprises a biomolecule (e.g., a protein) encapsulated in a polymeric microsphere or nanoparticles. In certain embodiments, BMP-2 encapsulated in PLGA microspheres may be embedded in a bone/polyurethane composite used in accordance with the present invention. Sustained release of BMP-2 can be achieved due to the diffusional barriers presented by both the PLGA and Polyurethane of the inventive composite. Thus, release kinetics of growth factors (e.g., BMP-2) can be tuned by varying size of PLGA microspheres as well as the composition and/or porosity of polyurethane composite.

To enhance biodegradation in vivo, composites of the present invention can also include different enzymes. Examples of suitable enzymes or similar reagents are proteases or hydrolases with ester-hydrolyzing capabilities. Such enzymes include, but are not limited to, proteinase K, bromelaine, pronase E, cellulase, dextranase, elastase, plasmin streptokinase, trypsin, chymotrypsin, papain, chymopapain, collagenase, subtilisin, chlostridopeptidase A, ficin, carboxypeptidase A, pectinase, pectinesterase, an oxireductase, an oxidase, or the like. The inclusion of an appropriate amount of such a degradation enhancing agent can be used to regulate implant duration.

Components to deliver may not be covalently bonded to a component of the composite. In some embodiments, components may be selectively distributed on or near the surface of inventive composites using the layering techniques described above. While surface of inventive composite will be mixed somewhat as the composite is manipulated in implant site, thickness of the surface layer will ensure that at least a portion of the surface layer of the composite remains at surface of the implant. Alternatively or in addition, biologically active components may be covalently linked to the osteoconductive matrix before combination with the polymer. As discussed above, for example, silane coupling agents having amine, carboxyl, hydroxyl, or mercapto groups may be attached to the osteoconductive matrix through the silane and then to reactive groups on a biomolecule, small molecule, or bioactive agent.

Bone Morphogenetic Protein. Certain embodiments comprise rhBMP-2, and of these certain embodiments, some have been found to reduce or eliminate resorption gaps formed when re-mineralization lags behind resorption in non-rhBMP2, or other osteoinductive material, embodiments. Without being bound by theory or mechanism, it is anticipated that certain embodiments of the present invention that release of rhBMP2 into pores created by resorption of osteoconductive matrix will reduce the time period between resorption and remineralization, resulting in more consistent mechanical properties and fewer resorption gaps.

Composites may be prepared by reactive liquid molding. rhBMP2 is added as a labile powder to the hardener component of the reactive PUR. Embodiments of the present invention are capable of incorporating rhBMP2 as a powder, which allows for both easy and highly tunable application of rhBMP2. Addition of rhBMP2 as a labile powder may results in a burst followed by a sustained release for >21 days, which may promote the most extensive bone formation. The labile powder approach is the simplest to use in a clinical environment.

The dosage of rhBMP2 will vary depending on the subject to be treated with the composite, the site to be treated, and the like. Exemplary embodiments of composites can comprise rhBMP-2 at a concentration of about 50 μg/ml, about 100 μg/ml, about 200 μg/ml, about 300 μg/ml, about 400 μg/ml, about 500 μg/ml, about 600 μg/ml, about 700 μg/ml, about 800 μg/ml, about 900 μg/ml, about 1000 μg/ml, about 1250 μg/ml, about 1500 μg/ml, about 1750 μg/ml, or about 2000 μg/ml.

Preparation of Composite

In general, inventive composites are prepared by combining osteoconductive matrix, polymers and optionally any additional components. To form inventive composites, osteoconductive matrix as discussed herein may be combined with a reactive liquid (i.e., a two-component composition) thereby forming a naturally injectable or moldable composite or a composite that can be made injectable or moldable. Alternatively, osteoconductive matrix may be combined with polyisocyanate prepolymers or polyols first and then combined with other components.

In some embodiments, osteoconductive matrix may be combined first with a hardener that includes polyols, water, catalysts and optionally a solvent, a diluent, a stabilizer, a porogen, a plasticizer, etc., and then combined with a polyisocyanate prepolymer. In some embodiments, a hardener (e.g., a polyol, water and a catalyst) may be mixed with a prepolymer, followed by addition of osteoconductive matrix. In some embodiments, in order to enhance storage stability of two-component compositions, the two (liquid) component process may be modified to an alternative three (liquid)-component process wherein a catalyst and water may be dissolved in a solution separating from reactive polyols. For example, polyester polyols may be first mixed with a solution of a catalyst and water, followed by addition of osteoconductive matrix, and finally addition of NCO-terminated prepolymers.

In some embodiments, additional components or components to be delivered may be combined with a reactive liquid prior to injection. In some embodiments, they may be combined with one of polymer precursors (i.e., prepolymers and polyols) prior to mixing the precursors in forming of a reactive liquid/paste.

Porous composites can be prepared by incorporating a small amount (e.g., <5 wt %) of water which reacts with prepolymers to form carbon dioxide, a biocompativle blowing agent. Resulting reactive liquid/paste may be injectable through a 12-ga syringe needle into molds or targeted site to set in situ. In some embodiments, gel time is great than 3 min, 4 min, 5 min, 6 min, 7 min, or 8 min. In some embodiments, cure time is less than 20 min, 18 min, 16 min, 14 min, 12 min, or 10 min.

In some embodiments, catalysts can be used to assist forming porous composites. In general, the more blowing catalyst used, the high porosity of inventive composites may be achieved.

Polymers and osteoconductive matrix may be combined by any method known to those skilled in the art. For example, a homogenous mixture of polymers and/or polymer precursors (e.g., prepolymers, polyols, etc.) and osteoconductive matrix may be pressed together at ambient or elevated temperatures. At elevated temperatures, a process may also be accomplished without pressure. In some embodiments, polymers or precursors are not held at a temperature of greater than approximately 60° C. for a significant time during mixing to prevent thermal damage to any biological component (e.g., growth factors or cells) of a composite. In some embodiments, temperature is not a concern because osteoconductive matrix and polymer precursors used in the present invention have a low reaction exotherm.

Alternatively or in addition, osteoconductive matrix may be mixed or folded into a polymer softened by heat or a solvent. Alternatively, a moldable polymer may be formed into a sheet that is then covered with a layer of osteoconductive matrix. Osteoconductive matrix may then be forced into the polymer sheet using pressure. In another embodiment, particles of an osteoconductive matrix are individually coated with polymers or polymer precursors, for example, using a tumbler, spray coater, or a fluidized bed, before being mixed with a larger quantity of polymer. This facilitates even coating of the particles and improves integration of the particles and polymer component of the composite.

In some embodiments, an inventive composite is produced with an injectable composition and then set in situ. For example, cross-link density of a low molecular weight polymer may be increased by exposing it to electromagnetic radiation (e.g., UV light) or an alternative energy source. In some embodiments, compositions utilized in the present invention becomes moldable at an elevated temperature into a pre-determined shape. Composites may become set when composites are implanted and allowed to cool to body temperature (approximately 37° C.).

The invention also provides methods of preparing inventive composites by combining osteoconductive matrix and polyurethane precursors and resulting in naturally flowable compositions. Alternatively or additionally, the invention provides methods to make a porous composite include adding a solvent or pharmaceutically acceptable excipient to render a flowable or moldable composition. Such a composition may then be injected or placed into the site of implantation. As solvent or excipient diffuses out of the composite, it may become set in place.

Polymer processing techniques may also be used to combine osteoconductive matrix with a polyurethane or precursors (e.g., polyisocyanates and polyols). In some embodiments, a composition of polyurethane may be rendered formable (e.g., by heating or with a solvent) and combined with osteoconductive matrix by injection molding or extrusion forming. Alternatively, polyurethanes and osteoconductive matrix may be mixed in a solvent and cast with or without pressure. For example, a solvent may be dichloromethane. In some embodiments, a composition of particle and polymer utilized in the present invention is naturally injectable or moldable in a solvent-free condition.

In some embodiments, osteoconductive matrix may be mixed with a polymer precursor according to standard composite processing techniques. For example, regularly shaped osteoconductive matrix particles may simply be suspended in a precursor. A polymer precursor may be mechanically stirred to distribute the particles or bubbled with a gas, preferably one that is oxygen- and moisture-free. Once components of a composition are mixed, it may be desirable to store it in a container that imparts a static pressure to prevent separation of the osteoconductive matrix and the polymer precursor, which may have different densities.

Interaction of polymer components with osteoconductive matrix may also be enhanced by coating individual particles of the osteoconductive matrix with a polymer precursor before combining them with bulk precursors. The coating enhances the association of the polymer component of the composite with the osteoconductive matrix. For example, individual particles may be spray coated with a monomer or prepolymer. Alternatively, the individual particles may be coated using a tumbler—particles and a solid polymer material are tumbled together to coat the particles. A fluidized bed coater may also be used to coat the particles. In addition, the particles may simply be dipped into liquid or powdered polymer precursor. All of these techniques will be familiar to those skilled in the art.

Inventive composites utilized in the present invention may include practically any ratio of polyurethane and osteoconductive matrix. Certain embodiments comprise about 10 wt % osteoconductive matrix, about 15 wt % osteoconductive matrix, about 20 wt % osteoconductive matrix, about 25 wt % osteoconductive matrix, about 30 wt % osteoconductive matrix, about 35 wt % osteoconductive matrix, about 40 wt % osteoconductive matrix, about 45 wt % osteoconductive matrix, about 50 wt % osteoconductive matrix, about 55 wt % osteoconductive matrix, about 60 wt % osteoconductive matrix, about 65 wt % osteoconductive matrix, about 70 wt % osteoconductive matrix, about 75 wt % osteoconductive matrix, about 80 wt % osteoconductive matrix, about 85 wt % osteoconductive matrix, or about 90 wt % osteoconductive matrix.

Still further, cured composites may comprise about 10 vol %, about 20 vol %, about 30 vol %, about 40 vol %, about 50 vol %, about 60 vol % or about 70 vol % of osteoconductive matrix. In this regard, the vol % initially present in the reactive mixture that is to cure into a composite can affect the characteristics and workability of the composites. Furthermore, composites may change during curing, and, for example, a reactive liquid that comprises approximately 35 vol % osteoconductive matrix can expand during curing so that the cured composite comprises about 15 vol %-20 vol % osteoconductive matrix.

Desired proportion may depend on factors such as injection sites, shape and size of the osteoconductive matrix, how evenly polymer is distributed among osteoconductive matrix, desired flowability of composites, desired handling of composites, desired moldability of composites, and mechanical and degradation properties of composites. The proportions of polymers and osteoconductive matrix can influence various characteristics of the composite, for example, its mechanical properties, including fatigue strength, the degradation rate, and the rate of biological incorporation. In addition, the cellular response to the composite will vary with the proportion of polymer and osteoconductive matrix. In some embodiments, the desired proportion of osteoconductive matrix may be determined not only by the desired biological properties of the injected material but by the desired mechanical properties of the injected material. That is, an increased proportion of osteoconductive matrix will increase the viscosity of the composite, making it more difficult to inject or mold. A larger proportion of osteoconductive matrix having a wide size distribution may give similar properties to a mixture having a smaller proportion of more evenly sized osteoconductive matrix particles.

In this regard, the terms "putty", "injectable filler", "bone void filler", "moldable composition", and the like, as used herein, refer to the various embodiments of PUR composites. These composites may all comprise PUR, osteoconductive matrix, and, optionally, a bioactive agent, such as rhBMP-2. For certain embodiments, there is a physical distinction between moldable or putty composites versus injectable or bone void filler composites.

Putty composites refer to composites that generally lend themselves to being moldable. Putties therefore tend to have a relatively higher initial viscosity, which is imparted by having a high relative concentration of osteoconductive matrix. Putties can lend themselves to being hand or machine molded to retain a particular shape around a bone injury site. Putty may also refer to composites that have relatively high osteoconductive solid particulate content (e.g., >45 wt %-55 wt %), such as allograft or synthetic allograft. Specific putties are also capable of functioning as weight-bearing composites. On the other hand, bone void fillers, injectable composites, and the like generally lend themselves to being injected, for instance through a syringe, into or onto an injury site. Thus, bone void fillers may be injected into and swell to fill a bone injury site. Bone void fillers tend to have relatively low osteoconductive matrix content (e.g., <45 wt %-55 wt %).

Inventive composites of the present invention can exhibit high degrees of porosity over a wide range of effective pore sizes. Thus, composites may have, at once, macroporosity, mesoporosity and microporosity. Macroporosity is characterized by pore diameters greater than about 100 microns. Mesoporosity is characterized by pore diameters between about 100 microns about 10 microns; and microporosity occurs when pores have diameters below about 10 microns. In some embodiments, the composite has a porosity of at least about 0.1%, at least about 10%, at least about 20%, at least about 30%, at least about 40%, at least about 50%, at least about 60%, at least about 70%, at least about 80%, at least about 90% or more than 90%. In some embodiments, inventive composites have a porosity in a range of 1%-20%, 30%-40%, 40%-45%, or 45%-50%. Advantages of a porous composite over non-porous composite include, but are not limited to, more extensive cellular and tissue in-growth into the composite, more continuous supply of nutrients, more thorough infiltration of therapeutics, and enhanced revascularization, allowing bone growth and repair to take place more efficiently. Furthermore, in certain embodiments, the porosity of the composite may be used to load the composite with biologically active agents such as drugs, small molecules, cells, peptides, polynucleotides, growth factors, osteogenic factors, etc, for delivery at the implant site. Porosity may also render certain composites of the present invention compressible.

In some embodiments, pores of inventive composite may be over 100 microns wide for the invasion of cells and bony in-growth (Klaitwatter et al., J. Biomed. Mater. Res. Symp. 2:161, 1971; which is incorporated herein by reference). In certain embodiments, the pore size may be in a ranges of approximately 50 microns to approximately 750 microns, for example, of approximately 100 microns to approximately 500 microns.

Embodiments also include polyurethane and osteoconductive matrix composites that exhibit tough mechanical properties and undergo plastic deformation. For example, embodiments may have compressive and bending strengths at yield exceeding 150 MPa and 50 MPa, respectively, and yield strains ≅5%. The inclusion of osteoconductive matrix can further enhance the mechanical characteristics of exemplary composites. For instance, certain PUR/bioglass embodiments are particularly strong, exhibiting yield strength and Young's modulus of about 60 MPa and about 2200 MPa, respectively. In other embodiments while compressive modulus may be in an approximate 50-350 MPa.

In some embodiments, compressive strength of dry inventive composites may be in an approximate range of 4-10 MPa, while compressive modulus may be in an approximate range of 150-450 MPa. Compressive strength of the wet composites can be about 1 MPa, about 10 MPa, about 20 MPa, about 30 MPa, about 40 MPa, about 50 MPa, about 60 MPa, about 70 MPa, about 80 MPa, about 90 MPa, or about 100 MPa. In some embodiments the wet torsional strength of composites is about 1 MPa, about 5 MPa, about 10 MPa, about 15 MPa, about 20 MPa, about 25 MPa, about 30 MPa, or about 35 MPa.

After implantation, inventive composites are allowed to remain at the site providing the strength desired while at the same time promoting healing of the bone and/or bone growth. Polyurethane of composites may be degraded or be resorbed as new bone is formed at the implantation site. Polymer may be resorbed over approximately 1 month to approximately 1 years. Composites may start to be remodeled in as little as a week as the composite is infiltrated with cells or new bone in-growth. A remodeling process may continue for weeks, months, or years. For example, polyurethanes used in accordance with the present invention may be resorbed within about 4-8 weeks, 2-6 months, or 6-12 months. A degradation rate is defined as the mass loss as a function of time, and it can be measured by immersing the sample in phosphate buffered saline or medium and measuring the sample mass as a function of time.

In this regard, some embodiments that achieve certain rates of new bone formation and polymer degradation at all stages have superior healing characteristics. In some embodiments the rate of new bone formation degradation over the rate of polymer degradation ($r_{NB}/r_{PD}$) is at least about 0.1, at least about 0.2, at least about 0.3, at least about 0.4, at least about 0.5, at least about 0.6, at least about 0.6, at least about 0.7, at least about 0.8, at least about 0.9, at least about 1.0, at least about 2.0, at least about 3.0, at least about 4.0, at least about 5.0, at least about 6.0, at least about 7.0, at least about 8.0, at least about 9.0, or at least about 10.0. Accordingly, in some embodiments $r_{NB}/r_{PD}$ is about 0.1 to about 10.0. In some embodiments new bone formation can be increased by addition of growth factors (e.g., rhBMP-2), and healing can also be improved, particularly at later stages, by utilizing a more slowly degrading polymer.

One skilled in the art will recognize that standard experimental techniques may be used to test these properties for a range of compositions to optimize a composite for a desired application. For example, standard mechanical testing instruments may be used to test the compressive strength and stiffness of composites. Cells may be cultured on composites for an appropriate period of time, and metabolic products and amount of proliferation (e.g., the number of cells in comparison to the number of cells seeded) may be analyzed. Weight change of composites may be measured after incubation in saline or other fluids. Repeated analysis will demonstrate whether degradation of a composite is linear or not, and mechanical testing of incubated materials will show changes in mechanical properties as a composite degrades. Such testing may also be used to compare enzymatic and non-enzymatic degradation of a composite and to determine levels of enzymatic degradation. A composite that is degraded is transformed into living bone upon implantation.

Use and Application of Composite

Polymers or polymer precursors, and osteoconductive matrix may be supplied separately, e.g., in a kit, and mixed immediately prior to implantation, injection or molding. A kit may contain a preset supply of osteoconductive matrix having, e.g., certain sizes, shapes, and levels of demineralization. Surface of osteoconductive matrix particles may have been optionally modified using one or more of techniques described herein. Alternatively, a kit may provide several different types of osteoconductive matrix.

Composites of the present invention may be used in a wide variety of clinical applications. A method of preparing and using polyurethanes for orthopedic applications utilized in the present invention may include the steps of providing a curable osteoconductive matrix/polyurethane composition, mixing parts of a composition, and curing a composition in a tissue site wherein a composition is sufficiently flowable to permit injection by minimally invasive techniques. In some embodiments, a flowable composition to inject may be pressed by hand or machine. In some embodiments, a moldable composition may be pre-molded and implanted into a target site. Injectable or moldable compositions utilized in the present invention may be processed (e.g., mixed, pressed, molded, etc.) by hand or machine.

Inventive composites and/or compositions may be used as injectable materials with or without exhibiting high mechanical strength (i.e., load-bearing or non-load bearing, respectively). In some embodiments, inventive composites and/or compositions may be used as moldable materials. For example, compositions (e.g., prepolymer, monomers, reactive liquids/pastes, polymers, osteoconductive matrix, additional components, etc.) in the present invention can be pre-molded into pre-determined shapes. Upon implantation, the pre-molded composite may further cure in situ and provide mechanical strength (i.e., load-bearing). A few examples of potential applications are discussed in more detail below.

In some embodiments, compositions and/or composites of the present invention may be used as a bone void filler. Bone fractures and defects, which result from trauma, injury, infection, malignancy or developmental malformation can be difficult to heal in certain circumstances. If a defect or gap is larger than a certain critical size, natural bone is unable to bridge or fill the defect or gap. These are several deficiencies that may be associated with the presence of a void in a bone. Bone void may compromise mechanical integrity of bone, making bone potentially susceptible to fracture until void becomes ingrown with native bone. Accordingly, it is of interest to fill such voids with a substance which helps voids to eventually fill with naturally grown bone. Open fractures and defects in practically any bone may be filled with composites according to various embodiments without the need for periosteal flap or other material for retaining a composite in fracture or defect. Even where a composite is not required to bear weight, physiological forces will tend to encourage remodeling of a composite to a shape reminiscent of original tissues.

Many orthopedic, periodontal, neurosurgical, oral and maxillofacial surgical procedures require drilling or cutting into bone in order to harvest autologous implants used in procedures or to create openings for the insertion of implants. In either case voids are created in bones. In addition to all the deficiencies associated with bone void mentioned above, surgically created bone voids may provide an opportunity for incubation and proliferation of any infective agents that are introduced during a surgical procedure. Another common side effect of any surgery is ecchymosis in surrounding tissues which results from bleeding of the traumatized tissues. Finally, surgical trauma to bone and surrounding tissues is known to be a significant source of post-operative pain and inflammation. Surgical bone voids are sometimes filled by the surgeon with autologous bone chips that are generated during trimming of bony ends of a graft to accommodate graft placement, thus accelerating healing. However, the volume of these chips is typically not sufficient to completely fill the void. Composites and/or compositions of the present invention, may be used to fill surgically created bone voids.

Inventive composites may be administered to a subject in need thereof using any technique known in the art. A subject is typically a patient with a disorder or disease related to bone. In certain embodiments, a subject has a bony defect such as a fracture. Any bone disease or disorder (i.e., condition) may be treated using inventive composites/compositions including genetic diseases, congenital abnormalities, fractures, iatrogenic defects, bone cancer, bone metastases, inflammatory diseases (e.g., rheumatoid arthritis), autoimmune diseases, metabolic diseases, and degenerative bone disease (e.g., osteoarthritis). In certain embodiments, inventive composites are formulated for repair of a simple fracture, compound fracture, or non-union; as an external fixation device or internal fixation device; for joint reconstruction, arthrodesis, arthroplasty, or cup arthroplasty of hips; for femoral or humeral head replacement; for femoral head surface replacement or total joint replacement; for repair of vertebral column, spinal fusion or internal vertebral fixation; for tumor surgery; for deficit filling; for discectomy; for laminectomy; for excision of spinal tumors; for an anterior cervical or thoracic operation; for the repairs of a spinal injury; for scoliosis, for lordosis or kyphosis treatment; for intermaxillary fixation of a fracture; for mentoplasty; for temporomandibular joint replacement; for alveolar ridge augmentation and reconstruction; as an inlay osteoimplant; for implant placement and revision; for sinus lift; for a cosmetic procedure; and, for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones, or metatarsal bones, and for repair of bone surrounding cysts and tumors.

Composites and/or compositions of the present invention can be used as bone void fillers either alone or in combination with one or more other conventional devices, for example, to fill the space between a device and bone. Examples of such devices include, but are not limited to, bone fixation plates (e.g., cranofacial, maxillofacial, orthopedic, skeletal, and the like); screws, tacks, clips, staples, nails, pins or rods, anchors (e.g., for suture, bone, and the like), scaffolds, scents, meshes (e.g., rigid, expandable, woven, knitted, weaved, etc), sponges, implants for cell encapsulation or tissue engineering, drug delivery (e.g., carriers, bone ingrowth induction catalysts such as bone morphogenic proteins, growth factors (e.g., PDGF, VEGF and BMP-2), peptides, antivirals, antibiotics, etc), monofilament or multifilament structures, sheets, coatings, membranes (e.g., porous, microporous, resorbable, etc), foams (e.g., open cell or close cell), screw augmentation, cranial, reconstruction, and/or combinations thereof.

EXAMPLES

The presently-disclosed subject matter is further illustrated by the following specific but non-limiting example.

The example may include compilations of data that are representative of data gathered at various times during the course of development and experimentation related to the presently-disclosed subject matter.

Example 1

Polyester Triol, LTI-PEG Prepolymer, and Allograft Synthesis and Characterization.

Poly(μ-caprolactone-co-glycolide-co-DL-lactide) triols with an equivalent weight of 300 g eq$^{-1}$ and a backbone comprising 60 wt % caprolactone, 30% glycolide, and 10% lactide (T6C3G1L300) are synthesized using known techniques. Preliminary experiments have shown this polymer undergoes approximately 80% degradation after 12 weeks in vivo. Appropriate amounts of dried glycerol and g-caprolactone (Aldrich), glycolide and DL-lactide (Polysciences), and stannous octoate (Aldrich, 0.1 wt-%) are mixed in a 100-ml flask and heated under an argon atmosphere with mechanical stirring to 140° C. for 24 h. The triol is washed with hexane and characterized by NMR, OH number, and GPC. An LTI-PEG prepolymer is synthesized by charging lysine triisocyanate (LTI, Osteotech) to a 50 mL flask, adding PEG200 (Aldrich, 200 g mol$^{-1}$, 2:1 mol LTI:mol PEG) dropwise under intense stirring at 60° C., and reacting overnight. The hydroxyl number of the polyester triol and % NCO of the prepolymer is measured by titration (Metrohm Titrino) and molecular weight by gel permeation chromatography (Waters Alliance). Mineralized allograft bone particles (Osteotech) is prepared by comminuting debrided and cleaned cortical bone in a mill, sieving (106-500 μm diameter), defatting in 70% denatured alcohol for >1 h, washing with sterile deionized water, lyophilizing for >6 h at −35° C., and vacuum-drying for >12 h at 35° C. and 500 mtorr. Lyophilized bone particles are treated with supercritical carbon-dioxide at 105° C. for >25 min, packed under argon, and gamma-irradiated at 25-35 KGy.

Composite Fabrication.

Defatted allograft bone particles are mixed with prepolymer, polyester triol, and catalyst solution, mixed for 60s, and cast into a mold as described previously. The catalyst solution is prepared as a mixture of 10% triethylene diamine catalyst (TEDA, Aldrich) in dipropylene glycol, and is added at sufficient concentration to yield a working time of 3-5 min and a cure time of 10-12 min. A sufficient amount of LTI-PEG prepolymer is added to yield an index of 115 (15% excess of isocyanate equivalents). The reactive mixture is injected into molds and cured at 37° C. for 24 h. Composites are incubated in PBS for one week, and the mass swelling ratio ($Q_m$) is calculated as the ratio of the wet and dry weights of the composite. Composition is determined by FT-IR (Bruker), and the free NCO is reported as the ratio of area under the NCO peak (2230 cm$^{-1}$) to that under the C=O stretching vibration (1760 cm$^{-1}$) peak. The density of the scaffolds is determined gravimetrically, and the porosity, defined as the volume fraction pores, is calculated from the composite foam density. Scanning electron microscope (SEM) micrographs (Hitachi S-4200) are used to determine pore size. In vitro degradation is determined by incubating specimens in PBS at 37° C. for up to 36 weeks and measuring the mass loss weekly.

In Vitro (Initial) Mechanical Properties.

Specimens for compression, torsional, and flexural testing are incubated in PBS at 37° C. for 24 h prior to testing. Cylindrical compression specimens (6 mm D×12 mm H) are loaded at 25 mm/min by the platens of a material testing system (Bionix 858, MTS). Upon converting the force vs. displacement to engineering stress vs. engineering strain, the modulus of elasticity (linear slope), yield strength (stress at 0.2% offset), and energy-to-failure (area under curve) is recorded. For torsion testing, each 'hour glass' specimen (gauge region: 10 mm long×2 mm diameter) is twisted at 40 deg/s until failure. The torque vs. twist data is then be converted to a shear stress (μ) vs strain (μ) curve using $\mu=\theta a/L$ and $\mu=[\theta(dT/d\theta)+3T]/2$, where θ is the angle of twist in radians, a is the radius of specimen, L is the gauge length of the specimen, and T is the torque. Ultimate torque and torsional modulus is measured as the maximum torque endured by the specimen and the slope of the initial linear portion of the curve, respectively. The bending strength and modulus of elasticity is determined from 3-point bending tests in which parallelepipeds (40 mm×4 mm×2 mm) are loaded at 3 mm/min using a bench-top material testing system (Dynamight, Instron). Peak force and stiffness are converted to the material properties using the flexural equations from beam theory. Dynamic mechanical properties (E', E", and tan μ) of 13.5 mm×25 mm×2 mm slabs are measured in 3-point bending mode (TA Instruments Q800 DMA). Both frequency (0.1-10 Hz) and temperature (−50-150° C.) sweeps are performed to determine the viscoelastic properties of the composites.

Remodeling of Allograft/PUR Composites in a Rabbit Femoral Condyle Model.

Composites are prepared as described previously and injected into unicortical bilateral plug defects in the femoral condyles of NZW rabbits. Allograft bone particles, catalyst solution, polyester triol, and LTI-PEG prepolymer are irradiated using a dose of approximately 25 kGY. Glycopyrrolate is administered at 0.01 mg/kg IM followed by ketamine at 40 mg/kg IM. Bilateral defects of approximately 6.1 mm diameter by 11 mm in depth are drilled in the metaphysis of the distal femurs of each rabbit. Composites from each treatment group (Table 2) is subsequently injected into each defect. Treatment groups for each composite are dispersed randomly among the rabbits. Rabbits are euthanized at the appropriate time points using Fatal-plus (2.2 mL/10 kg) intra-venously. After sacrifice, femurs are extracted and placed in a 1× phosphate buffer solution for 2 hours followed by dehydration in a series of ethanol and fixation in 10% formalin for 3 weeks. Testing of biomaterial composites found this difference or greater in maximum strength measures when the porosity was increased from 15% to 30%.

Ex vivo μCT is used to quantify the volume of new bone in the defect volume for the composites. Cross sectional contiguous μCT images of the entire defect are acquired at 70 kV and 114 mA with an isotropic voxel size of 30 μm on a Scanco μCT40 (Scanco Medical AG, Switzerland). A volume of interest comprising the entire defect is selected for analysis as defined by the perimeter of intact host bone around the defect site. Scanco software is used to determine fractional bone volume (BV/TV), which is used as the primary endpoint, and the architecture of the bone as published previously by the CoI. Additional analyses includes quantification of the mineralization void volume, average thickness between the resorbing implant and the new bone that is filling the defect, and, when possible, analysis of allograft volume.

Following μCT analysis, all specimens are dehydrated and embedded in MMA for non-decalcified histology. Central, 4-6 μm thick sections are cut and stained with H&E to assess inflammation, Safranin-O/Fast Green for cartilage, and Masson's trichrome for new bone and implant volume. The areas of inflammation, new bone, fibrous tissue, cartilage, and implant relative to the defect area are measured at low magnification using Osteomeasure software (Osteometrics, Decatur, Ga.). The volume of the demineralized zone in the composite is also measured relative to defect area, new bone area, and implant area.

An 8-mm trephine tool attached to a drill-press is used to core filled defects in rats. The ends of the cored defects are ground on silicon carbide paper to make them parallel. The cylindrical specimen of host bone surrounding the composite is imaged by μCT (FIG. 1) to verify the integrity of the filled defect and quantify both the BV/TV and apparent volumetric mineral density of the specimen. Following hydration in PBS, explanted specimens are placed between two compression platens and loaded at 25 mm/min. Force is recorded from an appropriately sized load cell and displacement is recorded from an extensometer attached to the platens (data collection at 50 Hz). The resulting force-displacement curve is converted to an engineering stress-engineering strain curve using the initial cross-sectional area of the specimen and the gage of the extensometer. Apparent modulus (slope of the linear portion of the curve), apparent yield strength (stress at proportional limit), and apparent peak strength (maximum stress is recorded).

Statistical analysis includes one-way ANOVA to test dose-dependent effects of the factors (either initial porosity or rhBMP-2) on compressive strength; BV/TV; and the areas of demineralized tissue, allograft, residual polymer, and new bone formation within the implant. Individual differences among groups at each time period are determined by the Fisher protected least significant difference test for multiple comparisons with significance established at $p<0.05$.

Remodeling of allograft/PUR composites depends on several parameters, including allograft volume fraction, initial porosity, and polymer composition. For allograft contents <50 vol %, the number of mechanical defects resulting from allograft particle-particle contacts is minimal, and therefore mechanical strength increases with increasing allograft volume fraction. Therefore, to maximize initial strength, the allograft content was selected as the highest possible level that supports injection through a syringe (34 vol %). Raman, μCT, and histomorphometry show enhanced new bone formation, accelerated PUR degradation, and minimized volume of the resorption front at higher porosity. However, initial strength decreases with increasing porosity. Therefore, in one embodiment of the present invention, an intermediate porosity of ~30% provides the necessary balance between biological and mechanical requirements. Data have shown that the composition of the polymer does not significantly affect the remodeling process if it is biocompatible and biodegradable. The present inventors have polyurethanes synthesized from an LTI-PEG prepolymer and poly(μ-caprolactone(60%)-co-glycolide(30%)-co-DL-lactide(10%)) triol (300 g eq$^{-1}$) and investigated in the rabbit studies. This polymer degrades to ~80% of its initial mass to non-toxic decomposition products after 12 weeks in a rabbit calvarial defect model. Without being bound by theory or mechanism, this degradation rate is suitable, but if necessary the degradation rate is decreased by varying the composition of the polyester triol or decreasing its equivalent weight. Alternatively, to increase the degradation rate, the equivalent weight of the polyester triol is increased, or a triol sensitive to MMP-mediated degradation is synthesized.

Example 2

Figure 2:
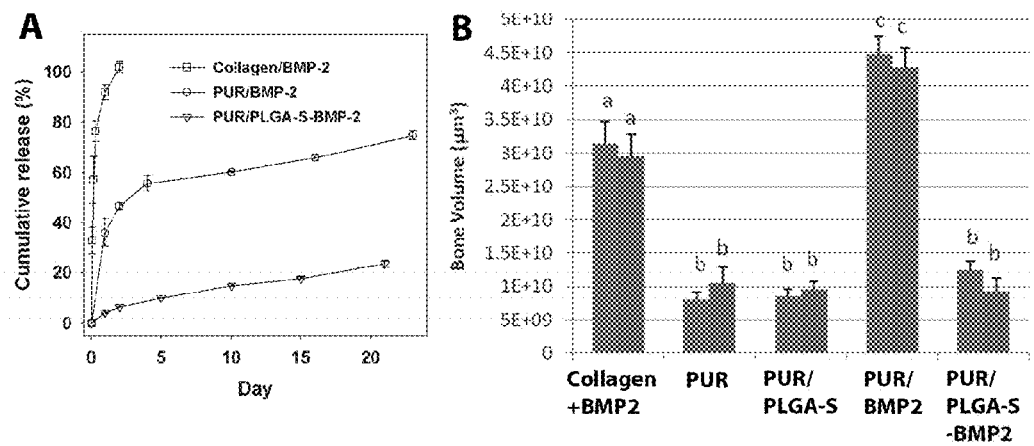
FIG. 2 shows data for PUR scaffolds incorporating 60 μg/ml rhBMP2 implanted into 6-mm femoral segmental defects in rats support cellular infiltration and new bone formation. (A) In vitro release kinetics measured for PUR scaffolds and collagen sponge. (B)μCT data show that PUR scaffolds exhibiting a burst followed by sustained release yield higher bone volume compared to a collagen sponge (burst release) and PUR scaffolds without the burst release. Blue: 4 weeks, Red: 8 weeks. (C) 1.25× and (D) 20× images of PUR/BMP-2 histological sections stained with trichrome show formation of new blood vessels (BV) and bone (NB) at 8 weeks.
Figure 2:
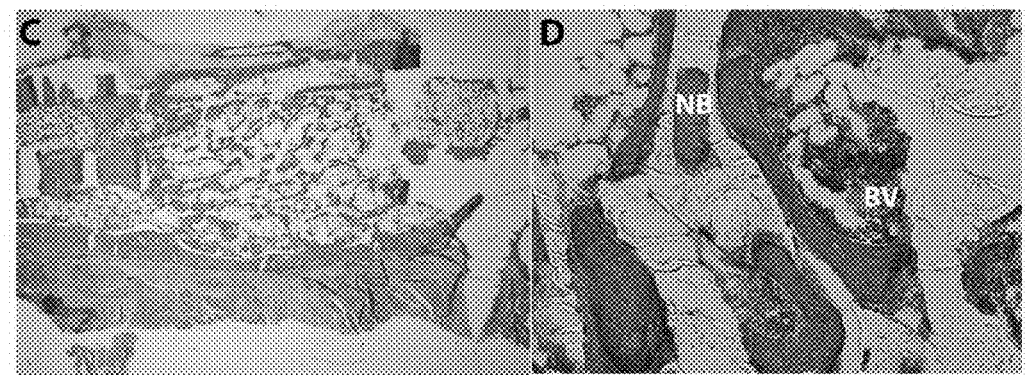

This Example shows that embodiments of the present invention are capable of producing a sustained release of rhBMP2 from PUR scaffolds, which increases new bone formation relative to a collagen sponge in a rat femoral segmental defect model. rhBMP2 delivered from a collagen sponge (INFUSE® Bone Graft, Medtronic) is an FDA-approved therapy for posterior-lateral spine fusion, tibial fractures, and specific craniofacial applications. The collagen sponge delivery system results in a bolus release of growth factor in the first 24-48 hours, but a number of studies have suggested that sustained release of rhBMP2 is more effective for promoting new bone formation. To modulate the release kinetics, rhBMP2 (60 μg/ml) was incorporated in PUR scaffolds by either direct addition as a labile powder or by encapsulation in large (L) or small (S) PLGA microspheres prior to incorporation in the scaffold. The labile powder (PUR/BMP2) formulation resulted in a burst followed by a sustained release of rhBMP2 up to day 21 (FIG. 2A). Encapsulation of rhBMP2 in ~1 μm PLGA (50/50 L/G, $M_n$~50,000 g/mol) microspheres prior to incorporation in the PUR scaffolds essentially eliminated the burst release.

The in vitro bioactivity of rhBMP2 released from PUR scaffolds was comparable to that of fresh rhBMP2, thereby demonstrating that this approach produced sustained release of active rhBMP2 over a 20-day period. To investigate the effects of release kinetics on healing in a critical size defect, PUR scaffolds incorporating rhBMP2 were implanted in 6-mm segmental femoral defects in Sprague-Dawley rats. After both 4 and 8 weeks implantation time, PUR/rhBMP2 scaffolds exhibited significantly more new bone formation compared to the collagen+rhBMP2 control (FIG. 2B). However, PUR scaffolds with no rhBMP2 and PUR/PLGA-S-BMP2 scaffolds (slow release) showed only minimal new bone formation. Histological sections of the PUR/BMP2 scaffolds show cellular infiltration, new bone formation, and blood vessel formation (FIGS. 2C and 2D). These results suggest that both a burst and sustained release of rhBMP2 are desirable for new bone formation, which is consistent with our study in a rat femoral plug model.

Figure 3:
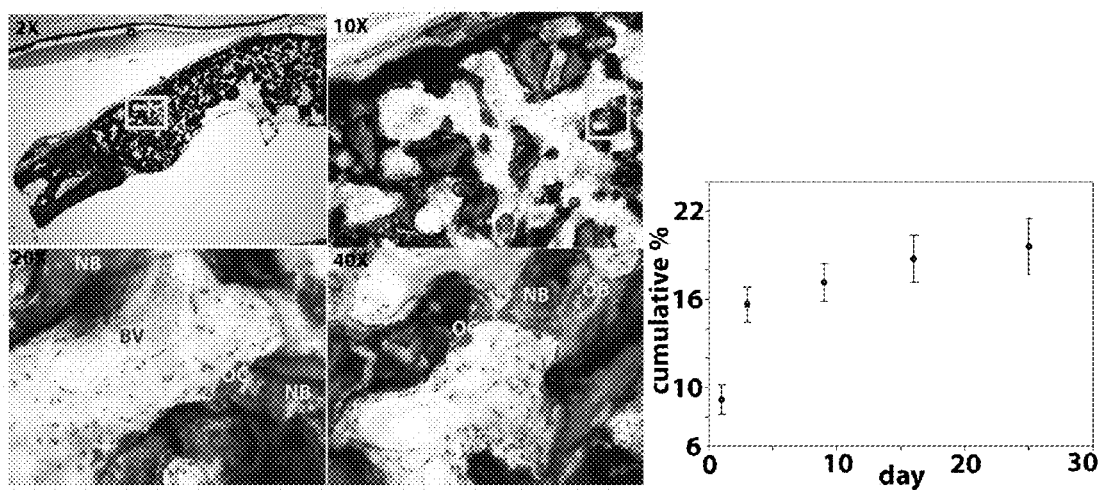
FIG. 3 shows images of allograft/PUR+420 μg/ml rhBMP2 injected into 15-mm calvarial defects in rabbits supports new bone formation. NB: new bone, OB: osteoblasts, OC: osteoclasts, BV: blood vessels. In vitro release kinetics shows ~20% release of BMP2 at 25 days.

Two-component polyurethanes enable customization using added biologics (e.g., growth factors and/or antibiotics) at the point of care. Allograft/PUR composites incorporating 420 μg/ml rhBMP2 into 15-mm were injected rabbit calvarial defects. The in vitro release kinetics show lower cumulative release (~20%, FIG. 3) at 25 days compared to the high (~90%) porosity PUR scaffolds (~70%, FIG. 2). However, the in vivo release kinetics are conjectured to be considerably faster due to the resorption of allograft particles, which creates new pores into which rhBMP2 can diffuse from the polymer. Histological sections at 6 weeks show extensive new bone formation along the upper surface of the composites and near the host bone interface (FIG. 3). In many animals, new bone had completely bridged the upper surface of the defect. Higher magnification images (20× and 40×) show active bone remodeling by osteoblasts (OB) and osteoclasts (OC), as well as formation of new blood vessels. Interestingly, the rate of polymer degradation was higher compared to the samples without rhBMP2, as evidenced by the absence of a significant amount of polymer at 6 weeks. In contrast, the collagen+rhBMP2 samples exhibited no significant new bone formation (comparable to the negative control).

Example 3

Synthesis of Allograft/PUR Composites Incorporating rhBMP2.

Briefly, rhBMP2 is mixed with a solution incorporating 20:1 heparin:rhBMP2 and 100:1 trehalose and lyophilized to yield a dry powder, which is subsequently added to the hardener component of the PUR prior to mixing with the prepolymer and allograft particles. Three replicate scaffold samples (~50 mg) containing 2.5 µg rhBMP-2 are immersed in 1 ml release medium (µ-MEM incorporating 1% BSA). The medium is refreshed every 24 h to minimize degradation of the growth factor. The rhBMP-2 concentration in the releasates is determined using a Human BMP-2 Quantikine ELISA kit (R&D systems).

rhBMP2 Release Kinetics from Allograft/PUR+rhBMP2 Composites.

Considering that the resorption of allograft particles has been shown to create new pores for cellular infiltration, the release kinetics from allograft/PUR+rhBMP2 composites is higher in vivo compared to in vitro. rhBMP2 is labeled with radioactive iodine ($^{125}I$) using IODO-BEADS Iodination Reagent (Pierce Biotechnology, Rockford, Ill.) in accordance with previously published techniques. IODO-beads containing approximately 1 mCi Na$^{125}$I is incubated in 1 ml of reaction buffer for 5 min under room temperature, followed by addition of 50 µg rhBMP2 to the reaction solution and incubation for another 25 min. The solution is then removed from the IODO-BEADS reaction tube and the Iodine-labeled rhBMP2 ($^{125}$I-rhBMP2) is separated in a Sephadex disposable PD-10 desalting column (Sigma-Aldrich). Eluted fractions are collected and a Cobra II Auto-gamma counter (Packard Instrument Co, Meridien, Conn.) adapted to determine the fractions containing the $^{125}$I-rhBMP2. The $^{125}$I-labeled growth factor is combined with non-labeled rhBMP-2 (1:5 hot-cold ratio) and trehalose (100:1 trehalose:rhBMP2 ratio), lyophilized, and mixed with the hardener component prior to mixing with the allograft bone particles and LTI-PEG prepolymer. To measure the in vivo release kinetics, the radioactive composites are injected into femoral defects and the release measured using a Cobra II Autogamma counter as previously described. Activity is measured over four 1-min periods and is repeated weekly while the rabbits are under sedation.

The Medtronic-recommended dose is 420 µg/ml for use with the collagen sponge. The data (FIG. 3) show that the sustained release achieved with the PUR delivery system results in more bone formation relative to the collagen sponge, which justifies investigation of a lower dose. Therefore, the two doses selected are 100 and 420 µg/ml.

Example 4

Composites were prepared by reactive liquid molding of defatted allograft bone particles (100-500 µm), LTI-PEG prepolymer, polyester triol, and catalyst mix using previously described techniques. The concentration of allograft particles are varied from 47-57 vol %. Composites with ≤45 vol % allograft do not support extensive cellular infiltration, and composites with >57 vol % allograft are not cohesive, have weak compressive strength, and cannot be injected through a 2.3 mm trocar. Composites are injected into 6-mm bilateral plug defects in the femurs of NZW rabbits, and calcium phosphate bone cement are investigated as a clinical control.

Rates of allograft resorption, cellular infiltration, new bone formation, polymer degradation, and biomechanical properties are measured as described herein. Biomechanical properties are measured for specimens cored from the femoral condyle. Preferred embodiments have rhBMP2 incorporated in the composites to accelerate re-mineralization.

Figure 4:
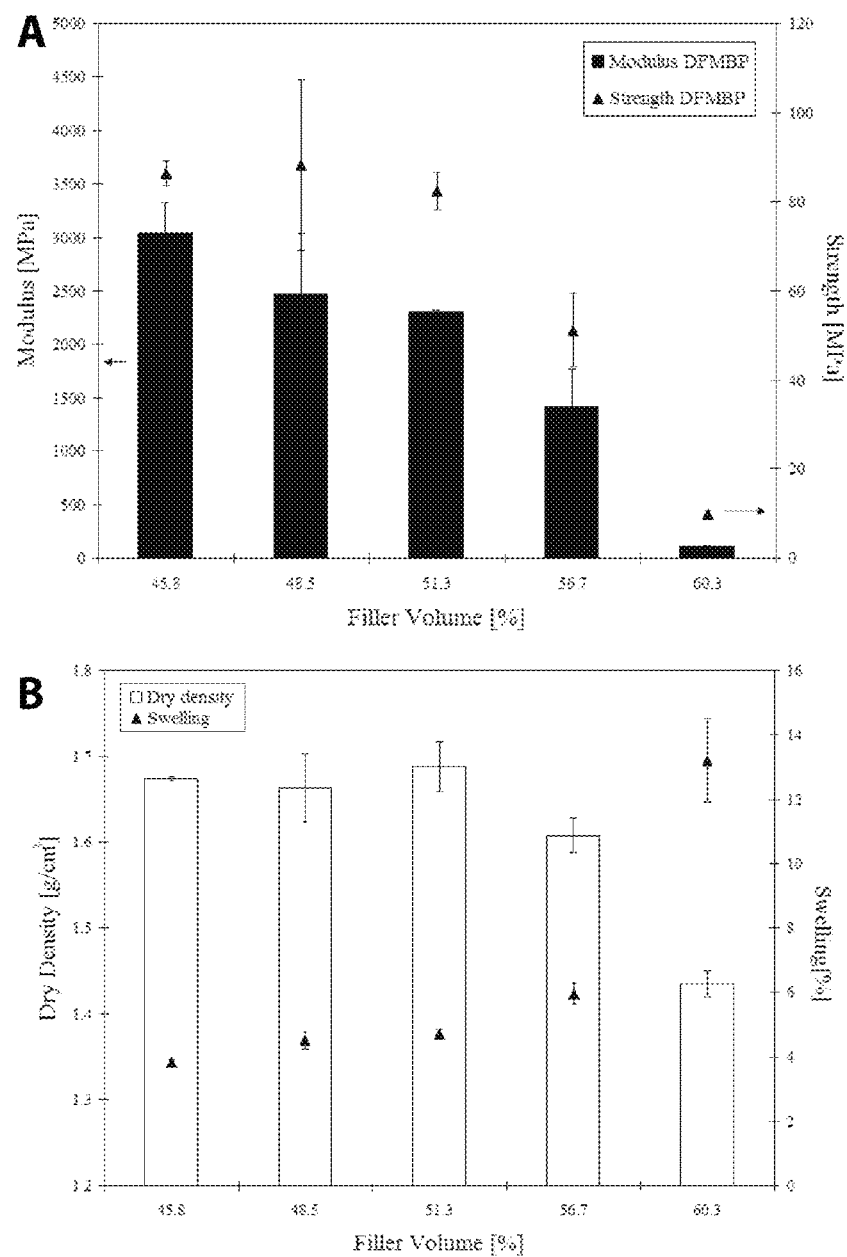
FIG. 4 shows (A) compressive properties and (B) density and swelling of allograft/PUR composites.
Figure 5:
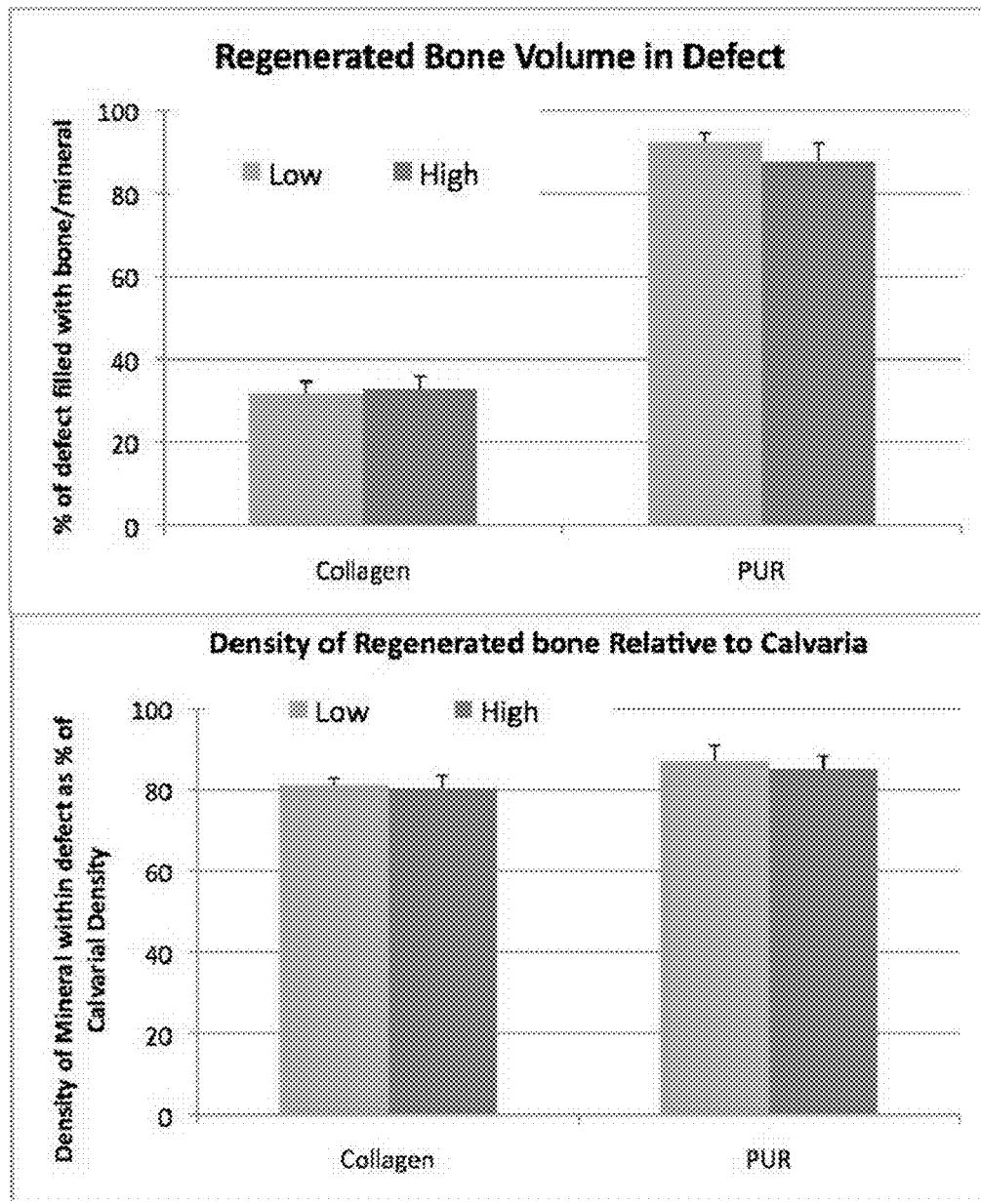
FIG. 5 shows data of the CATn analysis from a rabbit CSD calvaria study of PUR composite embodiments of the present invention.

Data show that high allograft content (>45 vol %) composites exhibit compressive mechanical properties comparable to those of trabecular bone in the femoral head. The compressive strength and modulus of allograft/PUR composites as a function of vol % allograft are plotted in FIG. 4A. For the 56.7 vol % allograft composite, the bending strength was 13.8±1.7 MPa. It is important to note that the composites in FIG. 4 were synthesized from a 100 g eq$^{-1}$ polyester triol. At allograft loading ≤57 vol %, the initial compressive properties exceed those of trabecular bone in the femoral head (17.5 MPa), and the yield strain is >5%. Preliminary experiments have shown that the defatted allograft bone particles react with the isocyanate-functional prepolymer, and that increasing the reactivity of the allograft through surface-demineralization does not increase the mechanical properties. At allograft loadings >57 vol %, there are significant defects in the composite since the loading is approaching the RCP limit. As a result, the density decreases and the swelling increases with increasing allograft content >57 vol %, resulting in reduced strength.

Data show that low-porosity allograft/PUR composites support cellular infiltration and remodeling in a rabbit femoral plug model. This Example shows substantial changes in opposite directions over a narrow range of allograft concentrations near the RCP limit. Therefore, embodiments of the present invention identify and include the optimum allograft content that effectively balances the mechanical and biological requirements.

Example 5

This Example demonstrates that in vivo resorption of allograft particles accelerates the formation of pores, which may then be infiltrated by rhBMP-2.

rhBMP2 is mixed with a solution incorporating 20:1 heparin:rhBMP2 and 100:1 trehalose:rhBMP2 and lyophilized to yield a dry powder, which are subsequently added to the hardener component of the PUR prior to mixing with the prepolymer and allograft particles.

In vitro release kinetics are measured by ELISA as described previously. In vivo release kinetics of rhBMP2 are higher compared to in vitro kinetics due to osteoclast-mediated resorption of allograft particles which creates pores in the composite over time.

Example 6

The following Example shows data in connection with embodiments of the present invention.

Figure 6:
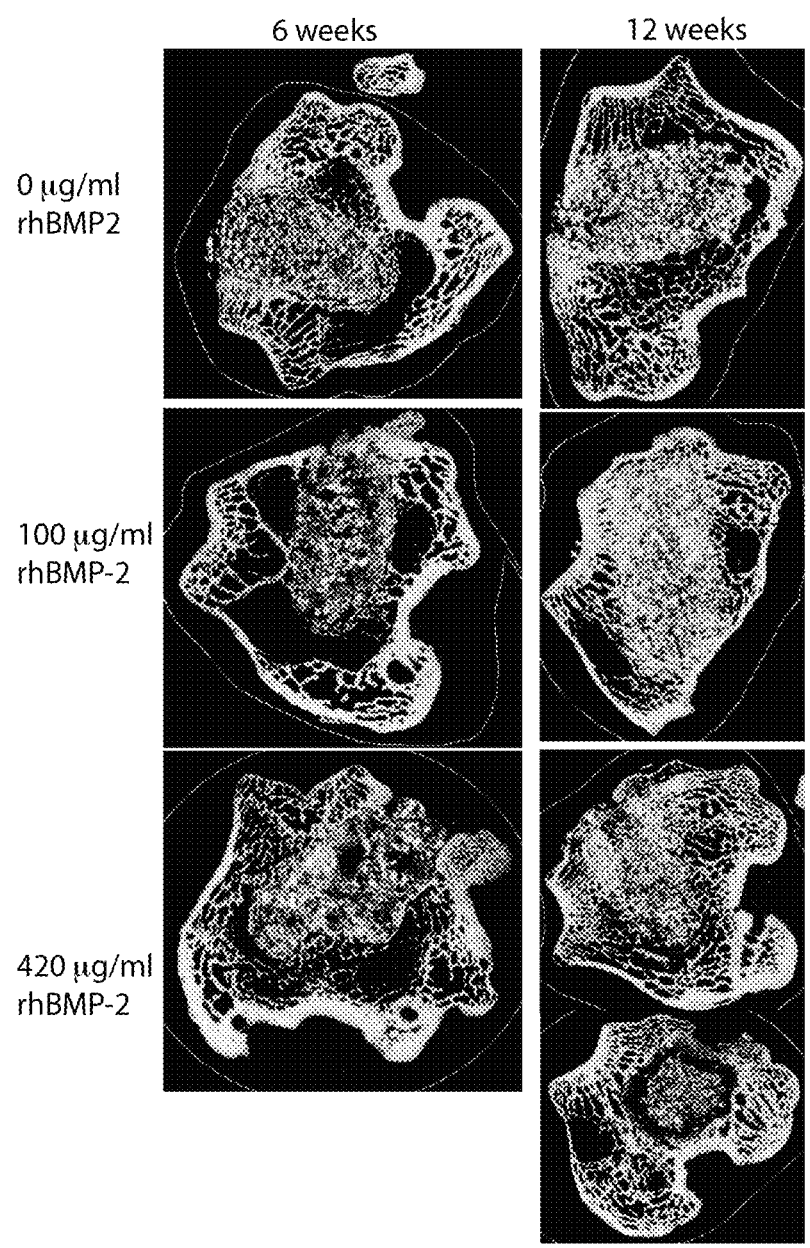
FIG. 6 shows μCT images of allograft/PUR putty carrying rhBMP-2 injected into a 6×11 mm plug defect in the femoral condyle of NZW rabbits. Residual allograft particles are distinguished by their irregular shape and sharp corners.

The present inventors have investigated the effects of the rhBMP-2 dose on remodeling of allograft/PUR composites injected into 6×11 mm plug defects in the femoral condyle of NZW rabbits. Three doses were evaluated: 0, 100, and 420 (the recommended dose for rabbits) mg/ml. The settable putty was prepared from a lysine triisocyanate (LTI)-polyethylene glycol (PEG) prepolymer, polyester polyol, allograft bone particles (AMBP), triethylene diamine (TEDA) catalyst in a dipropylene glycol (DPG) carrier, and rhBMP-2. The rhBMP-2 was mixed with trehalose and heparin, and freeze-dried to produce a powder. The polyester polyol backbone was composed of 60% caprolactone, 30% glycolide, and 10% lactide and had a molecular weight of 900 g mol$^{-1}$ (6C3G1L900). Polyol, AMBP, catalyst solution, and LTI-PEG prepolymer were added to a mixing cup and mixed for 90 seconds. The filler content (AMBP and rhBMP-2 powder) was maintained constant at 70 wt % for each treatment group. The resulting paste was then added to the rhBMP-2 vial and mixed for 60 seconds. Bilateral plug defects approximately 6 mm in diameter by 11 mm in depth were drilled in the metaphysis of the distal femurs of each rabbit. AMBP/PUR putty from each treatment group was injected into the defects. The setting time was approximately 10 minutes. After 6 or 12 weeks, the rabbits were sacrificed and the femurs removed. Faxitron LX-60 X-ray and mCT40 systems were used to acquire images of the femurs. The wet (i.e., after 24 h incubation in saline) compressive strength of the composites cured in vitro ranged from 27.2 to 33.2 MPa and was not dependent on the concentration of rhBMP-2. FIG. 6, immediately below, shows 2D mCT scans of the composites at each time point and dose of rhBMP-2. The images reveal evidence of allograft resorption and new bone formation in all treatment groups due to creeping substitution of the allograft component. Composites carrying rhBMP-2 reveal less allograft (appearing as large, dense, irregularly shaped white particles in the images) in the center of the putty. New bone formation also appears to be enhanced by rhBMP-2. Interestingly, the high (420 mg/ml) rhBMP-2 dose treatment group showed an unpredictable response, with some composites almost completely remodeled at 12 weeks (top) and others showing extensive resorption (bottom).

These data suggest that the low-porosity allograft/PUR composite putty is an efficient carrier for rhBMP-2, and that an optimum rhBMP-2 dose exists at which predictable healing can be achieved. Significantly, the data show that the optimum dose is likely less than the recommended dose for the absorbable collagen sponge carrier that yields a bolus release of drug.

Example 7

In this Example a composite was synthesized using the procedure described in the other Examples, keeping AMBP content was maintained constant at 45 wt % for each treatment group. Bilateral plug defects approximately 6 mm in diameter by 11 mm in depth were drilled in the metaphysis of the distal femurs of each rabbit. AMBP/PUR putty from each treatment group was injected into the defects. The setting time was approximately 10 minutes, and the porosity of the composites ranged from 27-30%. After 8 weeks, the rabbits were sacrificed and the femurs removed. Faxitron LX-60 X-ray and mCT40 systems were used to acquire images of the femurs. The images reveal evidence of allograft resorption and new bone formation due to cellular migration and creeping substitution of the allograft component. These data show that the injectable porous allograft/PUR composites remodel in the rabbit femoral condyle model.

Figure 7:
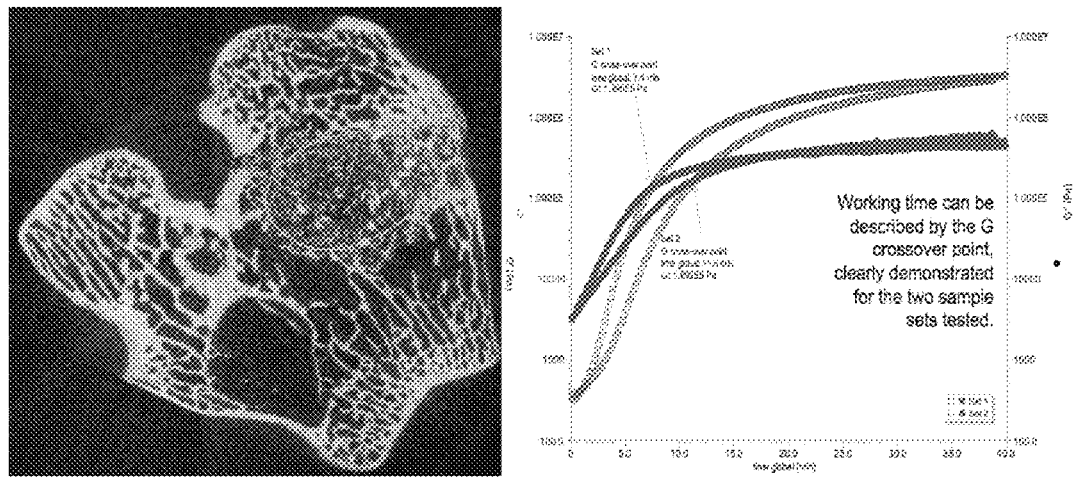
FIG. 7 shows (A) μCT images of allograft/PUR composites injected into 6×11 mm plug defects in the femoral condyle of NZW rabbits. Residual allograft particles are distinguished by their irregular shape and sharp corners. (B) Storage (G', left axis, open circles) and loss (G", right axis, filled circles) shear moduli measured as a function of time for the injectable porous allograft/PUR composite. (working time=G' and G" intersection).
Figure 8:
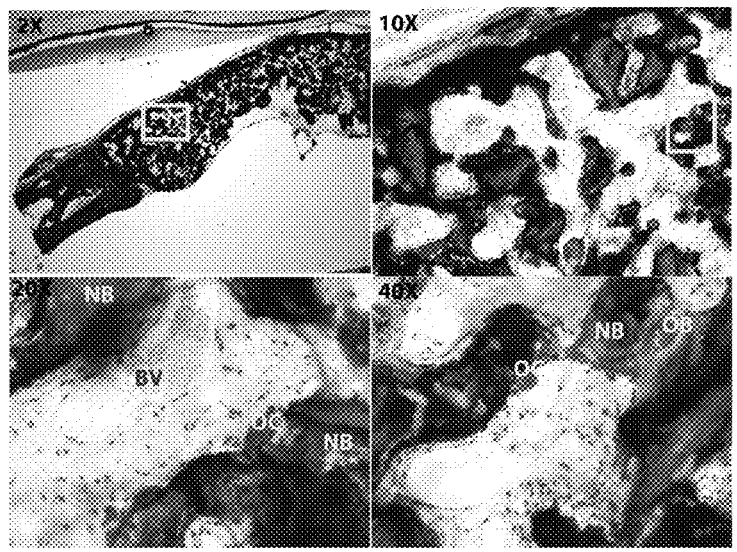
FIG. 8 shows allograft/PUR+80 μg/ml rhBMP2 injected into 15-mm calvarial defects in rabbits supports new bone formation. NB: new bone, OB: osteoblasts, OC: osteoclasts, BV: blood vessels.

The rheological profiles are shown in FIG. 7. Storage (G', left axis, open circles) and loss (G", right axis, filled circles) moduli were measured under shear conditions as a function of time for the injectable porous allograft/PUR composite. The working time is determined by the intersection between G' and G". Sample 1 (blue) showed a working time of 7.4 minutes, while Sample 2 (red) showed a working time of 11.6 min. These precise rheological measurements of the working time are consistent with the gel point previously measured as the time at which the composite no longer flows out of a syringe. We have also investigated the composition of the components that leach out of the composites after injection. Allograft/PUR composites were mixed and injected into a solution of buffer at 2 and 20 minutes post-mixing, and allowed to incubate in buffer for 24 h. The composition of the leachate (i.e., the buffer solution) was determined using NMR and gel permeation chromatography (GPC). The leachates were found to contain both unreacted polyester triol and dipropylene glycol (DPG), which is the carrier for the tertiary amine catalyst (triethylene diamine, TEDA). Both of these components have very low toxicity and do not accumulate in the body. Furthermore, no evidence of LTI, prepolymer, or TEDA was found in the leachates, suggesting that essentially all the NCO equivalents reacted in the composite. Additionally, these observations suggest that the TEDA is not released in a burst, but rather is released slowly over time as the composite degrades. It is important to note that TEDA is cleared from the body in urine and the total concentration in the composite is still at least an order of magnitude below the LD50. Thus it is anticipated that the slow release of TEDA from the composites will be cleared from the body and will not reach toxic levels. These results are consistent with the ISO10993 systemic and cytotoxicity tests, which showed no toxic effects of leachates obtained from the composites.

Example 8

This example shows low porosity injectable (reactive-allograft-bone/polyurethane) composites incorporating rhBMP-2. These embodiments enhance bone remodeling in a in a rabbit femoral plug model.

Embodiments of comprise allograft bone/polyurethane (PUR) non-porous composite putties which provides a release mechanism of recombinant human bone morphogenetic protein-2 (rhBMP-2) responsive to the surrounding cellular environment. The interactions between the filler surface and the polymeric matrix are investigated as a tool to reinforce the composites. rhBMP-2 was included in the formulation to enhance the osteogenic properties of low porosity injectable composites. The effects of rhBMP-2 dose on new bone formation at 6 and 12 weeks were investigated in a rabbit model.

The settable putty comprised a lysine isocyanate-polyethylene glycol prepolymer, polyester polyol, allograft bone (AMBP), amine catalyst, and rhBMP-2. The filler content of the composite putty was maintained at 70 wt %. To study the filler-matrix interactions, the surface of the allograft bone was a) demineralized (SD), or b) protected with 4-methoxyphenyl isothiocyanate (PROT); the compressive mechanical properties of the corresponding composites were compared. Two doses of rhBMP-2 were used: 110 and 440 µg/ml. The cure time was approximately 10 minutes. Bilateral defects (6 mm diameter by 11 mm in depth) were drilled in the metaphysis of the distal femurs of NZW rabbits. AMBP/PUR composite from each treatment group was injected into the defects. A µCT40 system was used to acquire images of the femurs. Histological ground sections were stained with Sanderson's rapid bone stain counterstained with Van Gieson.

AMBP/PUR composites exhibited compressive strengths (27.2-33.2 MPa) comparable to trabecular bone. No significant differences between the mechanical properties of AMBP and SD were identified; the PROT samples had mechanical properties three times lower than the AMBP composites. This observation suggested that AMBP reinforced the material by creating chemical bonds between the filler and the matrix. Histological sections of the composite without rhBMP-2 after 6 and 12 weeks of implantation revealed extensive cellular infiltration and new bone deposition, while µCT images were characterized by extensive remodeling with negligible resorption gaps. Incorporation of rhBMP-2 enhanced new bone formation relative to the composite without rhBMP-2, as evidenced by the presence of less AMBP. However, approximately 30% of the samples incorporating a high dose of rhBMP-2 displayed extensive areas of osteoclast-mediated resorption at 6 or 12 weeks. In this Example the high dose was the recommended dose for rabbits, suggesting that the release mechanism of rhBMP-2 from the composite may reduce the minimum effective dose required to enhance bone healing.

A conclusion was that AMBP had a sufficient density of reactive groups in the surface which promoted extensive interfacial binding with the matrix and reinforcement of the composite. Release of rhBMP-2 corresponding to 25% of the recommended dose enhanced remodeling of the material, while some of the composites showed resorption gaps at the high dose of rhBMP-2 corresponding to the recommended dose. Thus the allograft/polymer composites of the present invention is a promising approach for developing injectable biomaterials that maintain their initial mechanical properties during remodeling.

Example 9

This Example is directed to an exemplary injectable allograft bone/polymer composite bone void filler of the present invention. Among other things, this embodiment may be used for repairing calvarial defects.

Injectable MBP/PUR composite void fillers are composed of lysine triisocyanate (LTI), poly(ε-caprolactone-co-glycolide-co-lactide) triol, rabbit mineralized bone particles (RMBP, 100-500 μm), and Infuse rhBMP-2. The appropriate amounts of the triol, RMBP, and LTI-PEG prepolymer were added to a 10 mL cup and hand-mixed for 90 seconds. A 0.25 mL scoop was used to transfer approximately 0.38 g of the mixture into the vial of rhBMP-2, and the appropriate amount of catalyst solution (5% triethylene diamine in dipropylene glycol) was added to the vial. The components were mixed for 1 minute followed by loading and injection from a 1 mL syringe. The target bone content was 47 wt %, and the target porosity was 30%. A critical-sized rabbit calvarial defect study was designed to study the enhanced remodeling capability of the composites with the incorporation of rhBMP-2. A 15-mm circular defect was cut in the calvaria of New Zealand white rabbits. The volume of the defects was measured to be ~0.5 mL. Thus, a volume of 0.25 mL of MBP/PUR/rhBMP-2 composites was injected into the defect to allow for expansion.

The MBP/PUR/rhBMP-2 composites expanded to fill the entire defect volume. After 10 min, the foams had cured and become tack-free, completely dampening the pulsation of the dura. Compressive modulus and strength values range from 173-444 MPa and 4.4-9.5 MPa, respectively, which are in the range required to withstand pulsatile forces from the dura.[2] The wounds were subsequently closed and the rabbits were closely monitored until all vital signs were normal. Radiographs and histological sections of MBP/PUR composites without rhBMP2 showed ~2-4 mm of new bone ingrowth after 6 weeks implantation time in vivo. MBP/PUR composites incorporating rhBMP-2 showed bridging of the defect and extensive new bone formation. MBP/PUR composites exhibit suitable mechanical properties and remodeling for repair of calvarial defects, and are an effective delivery system for rhBMP-2.

Example 10

Injectable BVF for Rabbit Calvarial

Materials. The materials were obtained as discussed in Example 6.

Preparation of rhBMP-2

A solution of rhBMP-2 (1.5 μg/mL) was prepared by reconstituting rhBMP-2 powder per mixing instructions provided with the Infuse kit. The solution was aliquoted into vials to achieve 80 μg/mL of active rhBMP-2 dose in each sample. The vials were frozen at −80 C and lyophilized to achieve a powder.

Synthesis of the Injectable Composite

An index of 125 was targeted to produce a composite with a porosity of 47% upon injection. The TEDA catalyst was blended with DPG to yield a 10% solution of TEDA. Hydroxyl equivalents from the polyester triol, the DPG carrier, and water were included in the index calculation:

$$\text{INDEX} = 100 \times \frac{\text{NCO Eq}}{\text{OH Eq (Triol)} + \text{OH Eq (Water)} + \text{OH Eq } (DPG)}$$

The appropriate amounts of polyester triol, allograft (45 wt %), and LTI-PEG prepolymer were added to a mixing cup and mixed for 90 seconds. The resulting paste was then added to the rhBMP-2 vial followed by the addition of TEDA. After mixing for 60 seconds, the composite (BC) was poured in between parallel plates for rheological characterization, or injected into either molds for mechanical testing or into rabbit calvarial defects.

Rheological Properties

The rheological properties of non-setting samples were determined using a TA Instruments AR-2000ex rheometer. Samples were prepared without catalyst, poured between two 25 mm diameter parallel plates, and compressed to a gap of 1000 μm. The material was allowed to flow between the plates to cover the whole area and excess material was removed. The samples were then subjected to a dynamic frequency sweep (0.1 to 100 rad sec$^{-1}$) at 25° C. with controlled strain amplitude of 0.02%. A Cox Merz transformation was applied to the dynamic data to obtain the steady state viscosity (Pa*s) and shear stress (Pa) as a function of shear rate (s$^{-1}$). The shear stress versus shear strain data were fit to the Casson model.

Mechanical Properties

Cylindrical specimens with a 6 mm diameter were prepared by injecting the materials into a plastic mold. Samples with approximate height of 12 mm (n=4) were hydrated for 24 hours in PBS and then tested for compression using an MTS 898 equipped with a 13 kN load cell. The samples were preloaded to 12N, followed by compression at a constant strain rate of 25% min$^{-1}$ until failure. Load and displacement were recorded and transformed to stress and strain using the initial sample cross-sectional area and height respectively. The stress-strain curve was used to determine the Young's modulus, compressive strength (maximum stress), yield stress and strain, and energy-to-failure (area under the curve calculated at the yield point) of the samples.

Rabbit Study

Figure 9:
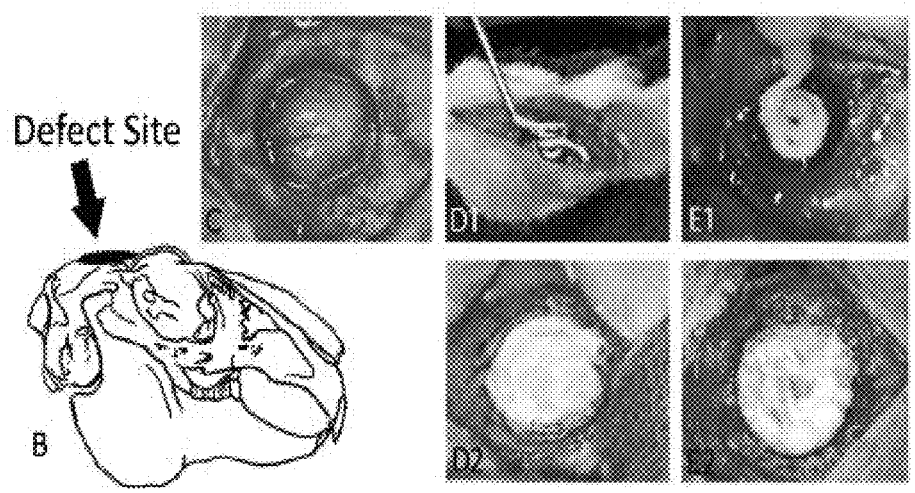
FIG. 9 shows the design of a NZW rabbit calvarial CSD study. (A) Table listing the study design. (B) Illustration of the rabbit calvarium showing the location of the defect. (C) Photograph of the empty defect. (D) Photographs of the CPC during injection (D1) and cure (D2). (E) Photographs of the composite during injection (E1) and cure (E2).

As shown in FIG. 9, four treatment groups were evaluated in this animal study using skeletally mature New Zealand white rabbits at two time points, 6 and 12 weeks. An empty defect was included as the negative control, and the injectable calcium phosphate cement (CPC) was used as the clinical control. The effects of rhBMP-2 delivered from the composite were also investigated at 6 weeks. Following standard practices for aseptic surgery, a full-thickness calvarial defect was prepared in the parietal bones using a 15-mm surgical trephine for rabbits (FIG. 9B). Briefly, upon the surgical exposure of the cranium, MicroAire surgical hand piece with a brass trephine was used to create the critical size defect (CSD) of 15 mm during copious saline irrigation (FIG. 9C). The cranial cap was carefully removed to separate the attached dura from the underside of the cap. Pressure with sterile gauze was applied to stop bleeding. The defects were treated by injection of the CPC (FIG. 9D) or composite (FIG. 9E) according to the pre-determined randomization scheme. Soft tissues were closed in layers using resorbable 3-0 Dexon sutures to create 2 sets of continuous sutures. The animals were euthanized at the given endpoints.

Radiographic Analysis

Radiographs were acquired using a Faxitron MX20 X-ray Digital System (Faxitron X-ray Corporation, Wheeling, Ill.) for each calvarium after extraction. The images were captured at 25 kV at a 15 second exposure time and imported into the Faxitron DR Software (Version 3.2.2). For quantification, the images were exported as a BITMAP file using window levels 1396/184. CTAn software v1.11, (Skyscan, Kontich, Belgium) was used to analyze the % defect area coverage and relative X-ray attenuation through the defect thickness for each treatment group. A region identical to the size of the defect created during the original study was outlined on each x-ray and automated thresholding was performed within this region using the Otsu method across all samples to determine the mineralized tissue within the defect. The percent of the defect area filled by the mineralized tissue was measured as a ratio of the pixels of gray above the threshold to the total number of pixels in the defect area. The relative x-ray attenuation through the defect was determined as the ratio of the mean grayscale level of the mineralized tissue within the defect to the mean grayscale value of the mineralized tissue of the surrounding host bone.

Histology and Histomorphometry.

The calvaria were placed in a solution of 10% neutral buffered formalin followed by a series of ethanol dehydrations. The specimens were then embedded in methyl/butyl methacrylate. The resulting blocks were then sectioned using an Exakt system, producing 75-micron sections. The sections were stained with Sanderson's rapid bone stain counterstained with van Gieson. Bone was stained red with osteocytes, osteoblasts and osteoclasts stained dark blue, residual polymer stained black, red blood cells stained turquoise and other cells stained a lighter blue. Quantifying the residual material (CPC or polymer), allograft bone, and new bone formation required the use of high magnification. Therefore, three zones progressing from the edge of the defect to the center region were examined at 40× magnification with and without polarizing the light. The edge of the defect was determined by visualizing (at 40× magnification) and then marking the disruption of the linear pattern of the calvarial bone and cells resulting from the surgical creation of the defect. To differentiate between the new bone and the residual allograft the allograft bone was quantified in these zones by meeting the following three criteria: (1) acellular, (2) angular in shape, and (3) illuminated under polarized light. In addition, the total amount of bone in the defect area was quantified using a stitched image taken with an Olympus camera (DP71) at 10× magnification (Microscope Olympus SZX16). Adobe Photoshop (CS3) was utilized to stitch the images together and to complete the histomorphometry (Version 7.0.1). Histomorphometry data was obtained by using a color thresholding and an image layering technique to quantify the pixels of each layer and compare it to the total pixels in the area of interest.

Injectability of Composites

Figure 10A:
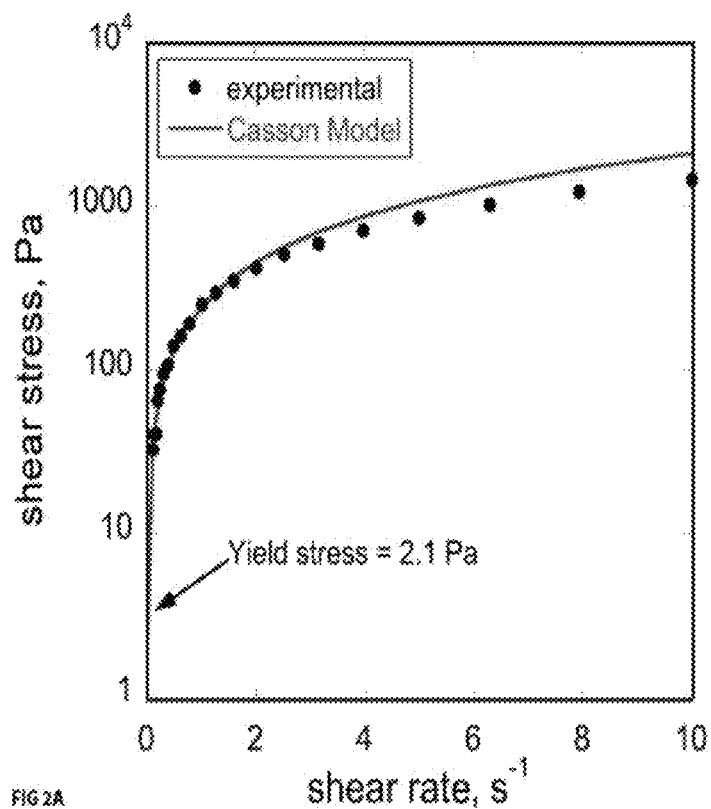
FIG. 10 shows rheological data measured for the non-setting form of embodiments of composite to characterize the injectability. (A) Shear stress versus shear rate. Data were fitted to the Casson model (solid line) used to predict the rheological properties of solid-filled suspensions and to calculate the yield stress (arrow). (B) Viscosity versus shear rate.
Figure 10B:
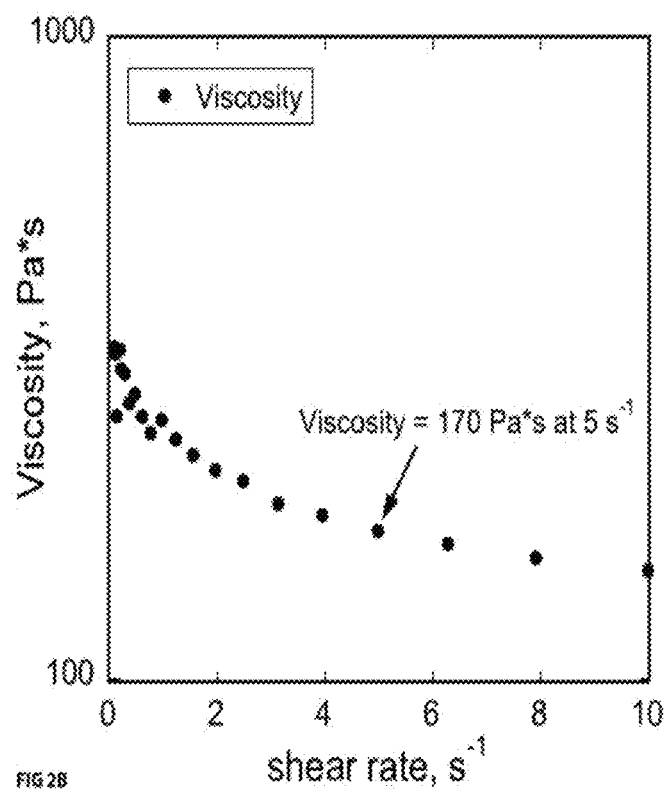

The working time of the composite, as measured as the time after which the material could not be injected from the syringe, was 4.5 min. The tack-free time, corresponding to the time when the material did not stick to a metal spatula, was 12 min. Solid-filled suspensions typically exhibit a yield stress, which is the pressure that is applied to initiate flow of the material. The viscosity data (FIG. 10B) show that the composite is shear-thinning, and the viscosity at 5 s$^{-1}$ is 170 Pa*s.

Compression Properties of the CPC and Composite

Figure 11:
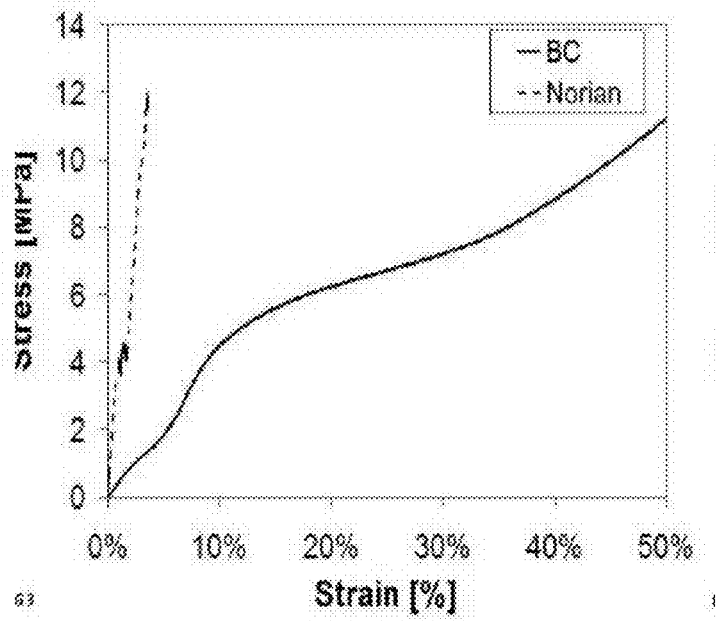
FIG. 11 shows stress-strain curves for an embodied composite and CPC measured under compressive loads. The area under the curve represents the energy-to-failure of the material.

The porosity was 47 vol % and the pore size was 177±90 µm, resulting in an allograft fraction of 17.5 vol %. Representative stress-strain curves for the composite and CPC measured under compression are shown in FIG. 11. The CPC failed due to brittle fracture at 1.070.2% strain and exhibited compressive strength of 15.9±3.4 MPa. In contrast, the composite exhibited plastic behavior and did not fracture at strains up to 50%. The yield strength of the composite was 4.06±0.03 MPa, above which the material continued to undergo plastic deformation up to 11.4±2.3% strain. The energy-to-failure, which is approximated by the area under the stress-strain curve, was 297±121 kJ m$^{-3}$ for the CPC and 3122±404 kJ m$^{-3}$ for the composite.

Injection of the CPC and Composites in Calvarial Defects

During the surgical procedure, no treatment, the CPC or one of the composite groups was injected in the defect, which had a volume of approximately 0.5 mL. A total of 0.25 mL of the composite was used to fill the defect as it expanded in volume during cure. After cure, the both the CPC and composite showed good contact with host bone. Some of the defects treated with the CPC developed cracks immediately after cure, which were observed before closure of the wound, while no cracks were observed for the composites.

Radiographic Analysis

Figure 12:
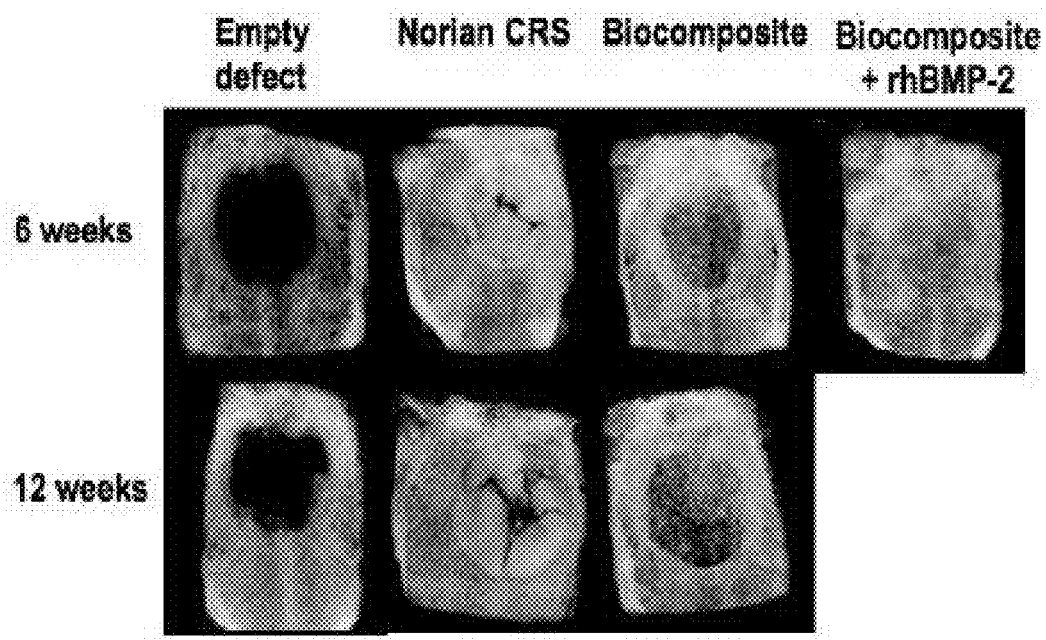
FIG. 12 shows radiographs of the empty defect, CPC, composite, and composite+rhBMP-2 at 6 and 12 weeks.
Figure 13:
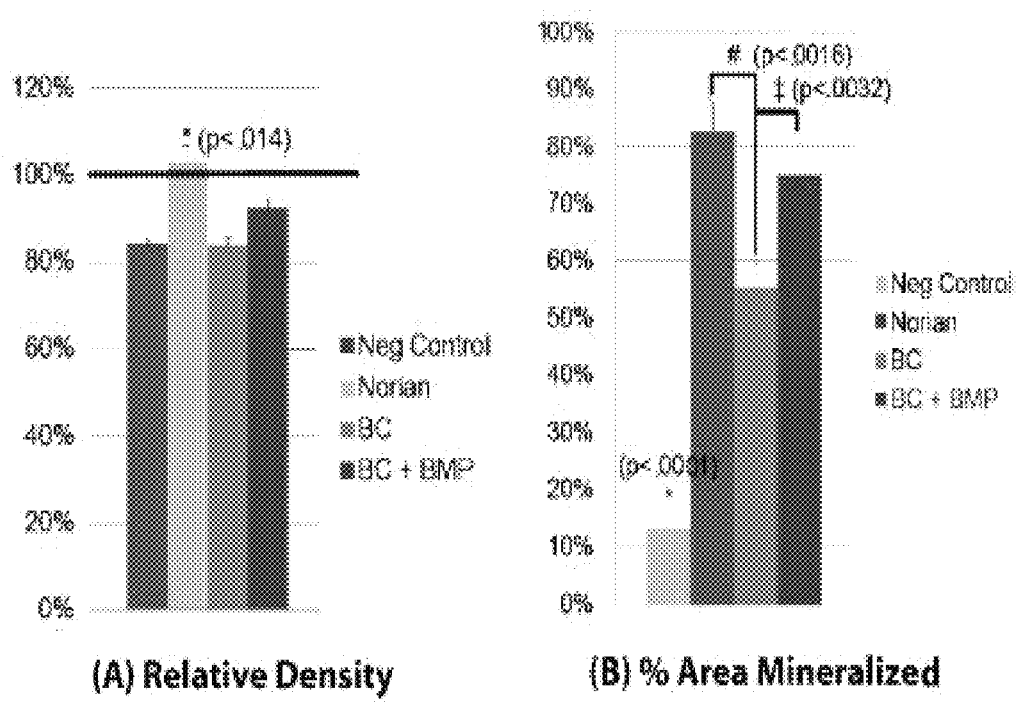
FIG. 13 shows the quantitative analysis new bone formation by analysis of radiographs for each treatment group at 6 weeks. (A) Relative density of the defect compared to the host bone. (B) Percentage area mineralized material in the defect.

Radiographs (FIG. 13) of the negative control defects showed minimal bone formation near the edges of the defect at both 6 and 12 weeks, as anticipated for a CSD. Consistent with observations during surgery, x-rays of the CPC treatment group showed cracking of the material. Bone ingrowth was observed around the perimeter of the composite treatment groups with traces of bone in the center. X-ray images (FIG. 12) of the BC+rhBMP-2 group suggested a substantial increase in new bone formation within the defect relative to the other treatment groups.

In FIG. 13A, the relative density (as approximated by the radio-opacity of the defect relative to the host bone) calculated using the CTAn software is plotted for each treatment group. While the CPC showed significantly higher relative density (p<0.02) compared to the other treatment groups at 6 weeks, the majority of the mineral content measured derived from residual hydroxyapatite and not new bone formation. There were no significant differences in relative density between the composite treatment groups (p=0.08). FIG. 13B shows the area % mineralization (as approximated by the percentage of the defect filled with tissue having density comparable to that of the host bone) for each treatment group. As expected, there was significantly less mineralized tissue in the negative control compared to the other treatment groups (p<0.0001). In addition, the percent defect area covered was significantly greater in the CPC and BC+rhBMP-2 groups compared to the BC only group (p<0.05). However, since CTAn analysis cannot differentiate between calcium phosphate, allograft, or new bone within the mineralized tissue, differences between the CPC and BC+rhBMP-2 groups were not significant.

Histology and Histomorphometry

Figure 14:
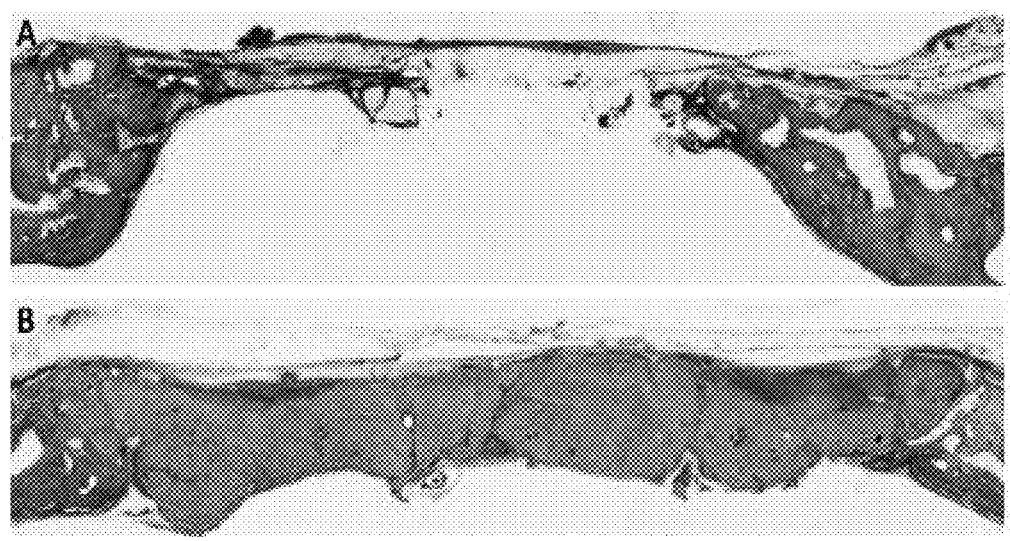
FIG. 14 shows histological sections of (A) an empty defect and (B) a CPC-treated defect.
Figure 15:
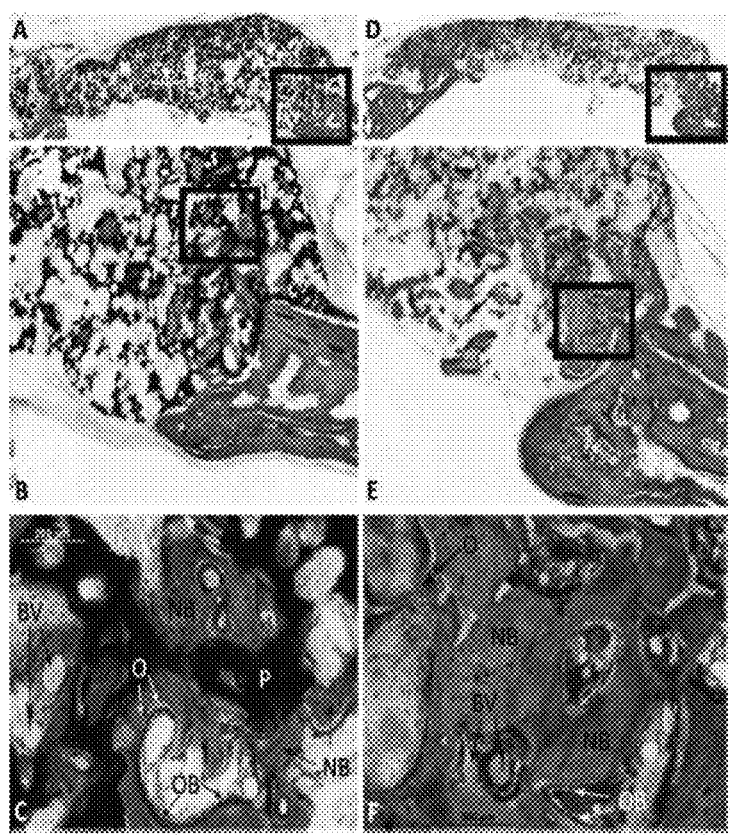
FIG. 15 shows histological sections of the composites at (A-C) 6 and (D-F) 12 weeks. (A&D) Low magnification (1.6×) image of the complete defect and host bone. (C&F) High magnification (18.4×) image showing blood vessels (BV), osteoblasts (OB) and osteoid (O), new bone (NB), and residual polymer (P).

Histological sections indicate that there were no adverse responses to any of the treatment groups used in this study. As expected, a fibrous scar filled the untreated defect at both time points (FIG. 14A). The CPC treatment groups (FIG. 14B) showed appositional bone growth around the surface and between the cracks of the material as evident by the mineralization stained in pink. This pattern was the same for both the 6 and 12 week CPC groups. However, there was no cellular infiltration into the cement. FIG. 15A-C shows a representative histological section of a composite sample at the 6 week time point. Cells, stained light blue, migrated into pores initially present in the material due to the foaming reaction as well as those resulting from resorption of the allograft bone particles. Near the host bone/composite interface, new bone lined with osteoid (stained light green) formed within the pores of the material. There was a moderate amount of residual polymer (stained black) remaining within the composite. Representative histological sections at 12 weeks for the composite treatment group (FIG. 15D-F) showed extensive polymer degradation as well as new bone formation.

Figure 16:
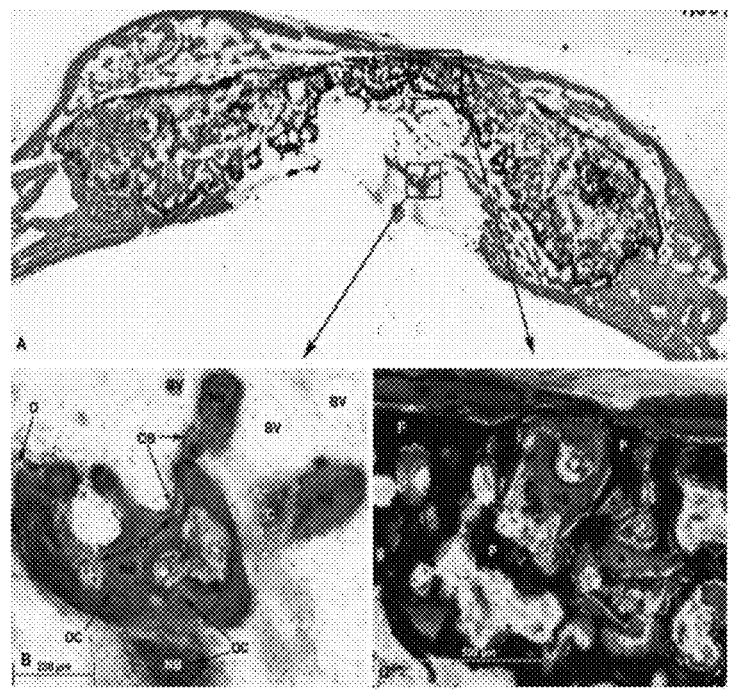
FIG. 16 shows histological sections of the composites incorporating rhBMP-2. (A) Low magnification (1.6×) image of the complete defect and host bone. (B) High magnification (18.4×) image showing blood vessels (BV), osteoblasts (OB) and osteoid (O), osteocytes (OC), new bone (NB), and cartilage (C). (C) High magnification (10×) image of a region near the upper surface of the composite showing residual polymer (P), residual allograft particles (A), and new bone (NB).

Representative histological sections of the BC+rhBMP-2 treatment group (FIG. 16) revealed extensive bone growth around the composite as well as throughout the pores of the material. A higher magnification view of a region near the lower surface of the defect (FIG. 16B) shows both intramembranous and endochondral new bone formation, as evidenced by the presence of cartilage (C). Areas of active remodeling characterized by osteoid (O) and osteoblasts (OB) lining the surface of the bone are evident, as well as formation of new blood vessels (BV). A higher magnification view of a region near the upper surface of the defect (FIG. 16C) shows residual allograft particles (A), residual polymer (black), and new bone formation (NB). Bridging of bone across the defect can also been seen in this histological section. While all rhBMP-2-treated defects showed new bone spanning the upper surface of the defect, calvarial defects in 5/10 animals in the BC+rhBMP-2 group had completely bridged with new bone at 6 weeks, which was significantly greater compared to the other treatment groups (p <0.0009), in which complete bridging was not observed in any of the defects.

Figure 17A:
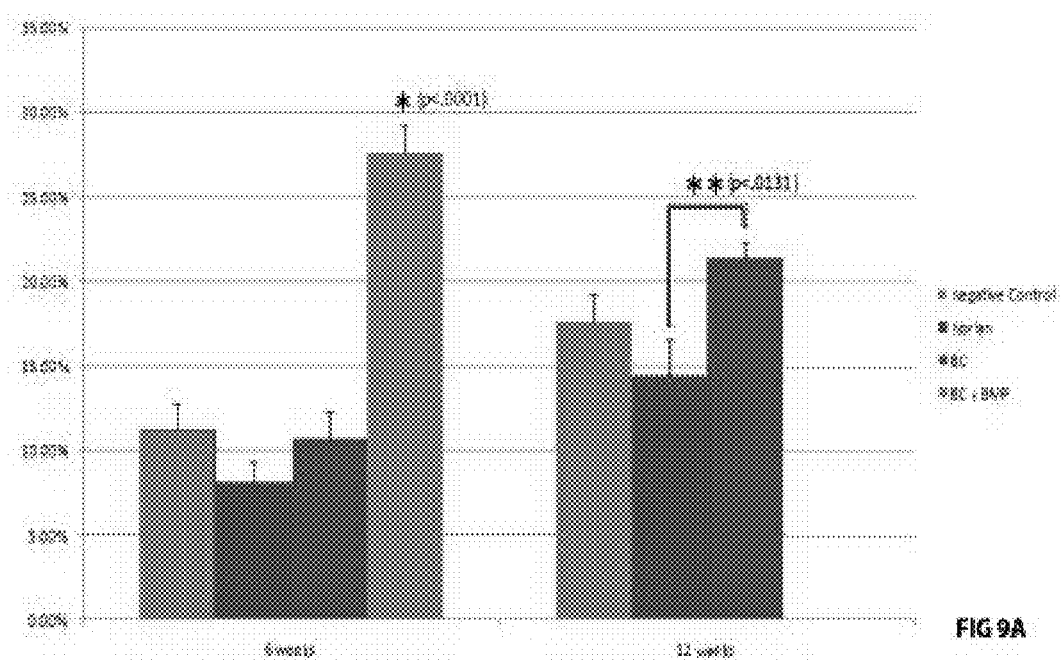
FIG. 17 shows histomorphometric analysis of calvarial defects. (A) Total bone (allograft and new bone) measured in the entire defect volume. (B) Image and schematic showing area of interest for high-magnification histomorphometric analysis required to distinguish allograft from new bone. (C) New bone, allograft, and polymer measured in the three representative areas progressing from the edge to the interior of the defect. New bone is significantly different (#) in Areas 2 ($p<0.03$) and 3 ($p<0.02$) for all treatment groups. Remaining polymer is significantly less (*) for the composite at 12 weeks than at 6 weeks in Area 1 ($p<0.03$).
Figure 17B:
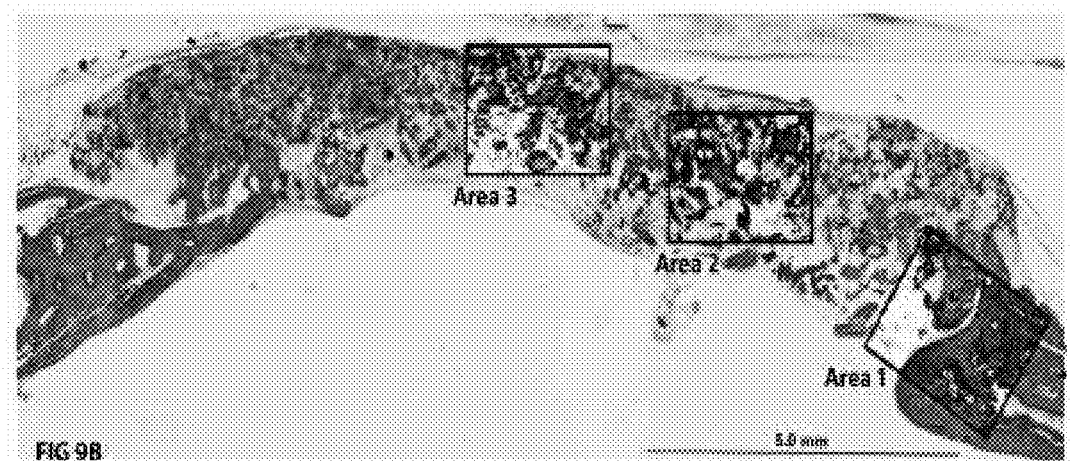
Figure 17C:
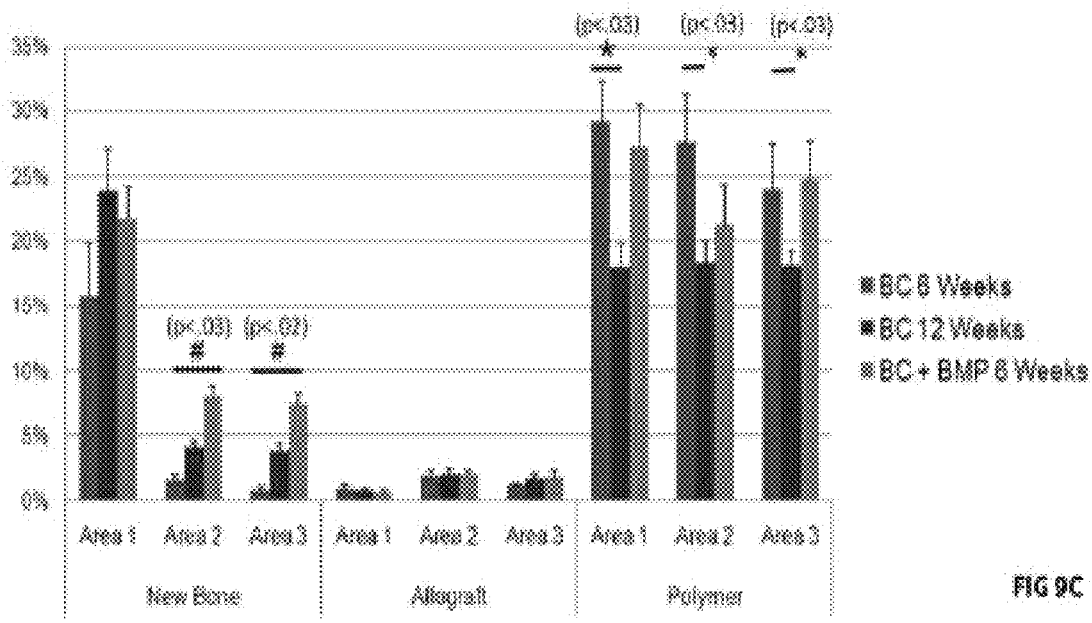

FIG. 17A shows the total area % of allograft and new bone measured over the entire defect for the composite treatment groups. Total bone (the sum of residual allograft and new bone) in the composites was greater than that in the negative control at both time points, and increased from 6 to 12 weeks. The addition of rhBMP-2 to the composites resulted in significantly more bone at 6 weeks compared to the composite at both 6 and 12 weeks without rhBMP-2. To determine how much of the total bone was newly formed versus residual allograft, three areas progressing from the edge to the interior of the defect (FIG. 17B) were analyzed at high magnification. As shown in FIG. 17C, new bone formation was highest in Area 1 (near the host bone interface) for all three treatment groups. However, the BC+rh-BMP-2 group had significantly higher new bone formation in the interior areas 2 and 3. The area % of allograft was <2% for all groups in all three areas, suggesting that most of the total bone in Area 1 of the composite was newly formed and not allograft. At 6 weeks, the area % of new bone in areas 2 and 3 was comparable to the area % of allograft. However, at 12 weeks and in the composites with rhBMP-2, the amount of new bone in the interior areas exceeded that of residual allograft. As anticipated, the polymer decreased significantly from an initial value of 24-29 area % at week 6 to 18 area % at week 12 (the difference was significant only for area 1). Interestingly, while the residual polymer was lower at 6 weeks in the presence of rhBMP-2, the difference was not significant, suggesting that delivery of this relatively low amount of rhBMP-2 does not substantially affect the degradation rate of the polymer.

The composites exhibited handling properties, including working and setting times, that are comparable to those reported for CPCs. After injection, the composites expanded to fill the defects and hardened to form a tough elastomeric solid that did not fail mechanically throughout the healing process, in contrast to the CPC that exhibited brittle fracture after cure. The mechanical integrity of the materials observed in vivo was consistent with their in vitro mechanical properties, as evidenced by the order of magnitude higher energy-to-failure of the composites compared to the CPC. As early as 6 weeks, cells had infiltrated the composites, resulting in new bone formation near the host bone/composite interface, while the CPC showed minimal cellular infiltration. rhBMP-2 added to the composites enhanced new bone formation, resulting in a bridge of bone covering the upper surface of the defect as well as new bone formation throughout the interior of the composite.

The PUR composite was shear thinning over a physiologically relevant range of shear rates (0.01-10 $s^{-1}$). The initial viscosity of the composite at 5 $s^{-1}$ was 170 Pa*s. The relatively higher viscosity of the composites is due in part to the higher viscosity of the liquid PUR components (21 Pa*s compared to $10^{-3}$ Pa*s for water). The composites showed a yield stress of only 2.1 Pa. Thus, PUR composites may present handling advantages compared to CPCs due to their higher initial viscosity, which minimizes filter pressing and extravasation, and relatively low yield stress, which requires a smaller initial force to inject the material.

The composite set to form a hard solid within 10 minutes of injection, which offers the advantage of wound closure shortly after placing the material. The composites did not reveal evidence of cracking or fragmentation either immediately after cure or at the time of explanation. The superior mechanical integrity of the composite is attributed to its tougher mechanical properties, having an energy-to-failure measured under compression of 3122±404 kJ $m^{-3}$ compared to 297±121 kJ $m^{-3}$ for the CPC. Taken together, these observations suggest that the composite may be more effective at providing early protection to the brain during the early stages of the healing process.

Rapid cellular infiltration and remodeling is another desirable attribute of injectable bone grafts. Histological sections (FIG. 15) showed extensive cellular infiltration for all of the composite groups. In the present study the volume fraction of allograft in the cured composite was 17.4 vol %. In the rabbit calvarial defect and athymic rat femoral plug studies, the combination of pore and allograft volumes were 61.4 and 59.7 vol %, respectively. Thus the rapid cellular infiltration of these composites is consistent with the notion that cellular infiltration and remodeling proceed independent of polymer degradation when the sum of the pore and osteoconductive matrix volumes approaches 64 vol %, the random close-packing (RCP) limit for spheres.

The polymer, which was initially present at 36 vol %, had degraded to 24-29 area % at week six and 18 area % at week 12. These data suggest that the polymer had degraded by 19-33% at week 6 and 50% at week 12, which is in reasonable agreement with an in vitro study reporting 10% and 45% mass loss of the polymeric scaffold having the same composition at 6 and 12 weeks, respectively. In the previous in vitro study, the tensile strength and modulus of the scaffolds decreased to <20% of their initial values after 8 weeks of degradation time in vitro. When rhBMP-2 was added to the composites, histological sections showed a bridge of new bone covering the upper surface of the implant as well as new bone formation throughout the defect. While the area % polymer was less in the composites+rhBMP-2 group compared to the composite group at 6 weeks, the differences were not significant. Thus rhBMP-2 released from the matrix at doses equal to 20% of that recommended for the ACS carrier does not significantly affect the degradation of the PUR phase.

The improvement in new bone formation at sub-optimal doses was attributed to the more sustained release of rhBMP-2 from the PUR carrier, compared to the bolus release (>30%) of rhBMP-2 from the collagen sponge. Extensive vascular formation in the defect was observed in the composites incorporating rhBMP-2. In addition to its osteoinductive and angiogenic effects, rhBMP-2 also stimulates osteoclast activity. Thus rhBMP-2 released from the composites can accelerate the resorption of allograft bone particles and the consequent infiltration of cells and growth of new bone in the newly formed pores.

Example 11

Putty Rabbit Femur

This Example shows the remodeling of injectable ABP/PUR composites in a NZW rabbit femoral condyle plug defect model. Reducing the volume fractions of allograft particles from 67 vol % to 57 vol % were used to slow the rate of cellular infiltration, resulting in more balanced remodeling. The potential for rhBMP-2 to enhance new bone formation and support balanced remodeling in the low-porosity composites is also shown.

Materials. See Previous Example.

Preparation of rhBMP-2

The rhBMP-2 was supplied as a solution comprising 35% acetonitrile and 0.1% TFA. A separate acetonitrile/TFA solution was prepared containing a ratio of 10:1 of trehalosedehydrate:heparin sodium. The rhBMP-2 and trehalose mixtures were combined such that the ratio of rhBMP-2 to trehalose was 1:125. The resulting mixture was distributed in glass vials and frozen at −80° C. in preparation for freeze-drying, which produced a powder.

Synthesis of AMBP/PUR Putty

The method of Example 12 was implemented, but the target index was 130 and the catalyst concentration was 5500 ppm. The filler content (AMBP and rhBMP-2 powder) was maintained at 70 wt % for each putty treatment group, and rhBMP-2 was utilized at low (100 µg/mL) and high (400 µg/mL) concentrations. The resulting reactive paste had a tack-free (i.e., cure) time of approximately 10 minutes.

Mechanical Properties

Cylindrical samples of each treatment group were prepared for mechanical testing. The reactive paste was transferred into cylindrical plastic cups and a 1-pound weight (20.7 psi) was placed on the material for 10 minutes. The resulting cylinders were placed in a vacuum oven at 37° C. overnight and removed from the plastic cups. After cure, the cylinders were removed from the cups and cut using a Buehler saw to produce 6 mm×12 mm cylinders. Three different formulations were synthesized. After 24 hours of hydration in phosphate buffered saline (PBS), the rods were tested using a MTS 898 using compression.

Animal Study

Forty-two New Zealand White (NZW) rabbits weighing between 3.8 and 4.1 kg were used in this study. All surgical and care procedures were carried out under aseptic conditions per the approved IACUC protocol. The AMBP/PUR putty components were gamma irradiated using a dose of approximately 25 kGY. Glycopyrrolate was administered at 0.01 mg/kg IM followed by ketamine at 40 mg/kg IM. Bilateral defects of approximately 6 mm diameter by 11 mm in depth were drilled in the metaphysis of the distal femurs of each rabbit. AMBP/PUR plugs from each treatment group were subsequently injected into each defect using a 1 mL syringe. Treatment groups for each composite were dispersed randomly among the rabbits. The rabbits were euthanized at both 6 and 12 week time points using Fatal-plus (2.2 mL/10 kg) intra-venously.

µCT Analysis

A µCT40 (SCANCO Medical, Basserdorf, Switzerland) was used to acquire images of the composites prior to implantation and of the extracted femurs post implantation at 6 and 12 weeks. Briefly, µCT scans were performed at 70 kV source voltage and 114 µA source current and at a spatial resolution of 36 µm and manufacturer provided software was used to reconstruct axial images. The reconstructed image stack was converted from a TIFF to a BMP format using ImageJ (U.S. National Institutes of Health, Bethesda, Md.) and reoriented to be perpendicular to the axis of the femoral condylar defect created using the cortical borders of the defect site for alignment. Images were calibrated using hydroxyapatite phantoms with densities of 100-800 mgHA/cc. µCT thresholding was performed to include only ossified tissues (defined as a density greater than 346 mgHA/cc) by using the Otsu algorithm applied across all the samples in the entire study. The region of interest was registered in each sample using the defect boundary to define a 6 mm circular section in the first slice at the outer cortical surface of the femur and proceeding to a depth of 11 mm to generate a cylindrical region of interest. The bone area within the 6 mm circular cross sections were calculated for each section from the femoral cortex to the interior of the defect space and grouped by treatment and time point to determine spatial trends in bone regeneration. The bone volume (BV), tissue mineral density (TMD) and multiple 3D morphometric descriptors of trabecular organization and connectivity within this region of interest were computed using CTAn software (Skyscan, Aartselaar, Belgium). The relative distribution of trabecular thickness was calculated as the relative percentage of trabeculae in each range of thickness for the composites prior to implantation and after implantation at 6 and 12 weeks to evaluate bone remodeling response within the grafts.

Histology and Histomorphometry

The femora were placed in a solution of 10% formalin for two weeks followed by a series of ethanol dehydrations. After fixation, the femurs were embedded in poly(methyl methacrylate) and 200-µm sections were cut from the resulting blocks using an Exakt band saw. The sections were then ground and polished using an Exakt grinding system to less than 100 µm and stained with Sanderson's rapid bone stain counterstained with van Gieson. Residual allograft bone particles stained light brown, residual polymer stained black, new bone stained pink with dark blue osteocytes within the matrix, red blood cells stained torquiose, and other cells stained a lighter blue. Residual allograft bone particles and new bone formation were quantified in an area of interest 1.5 cm high×6 cm wide located in the center of the defect. Images were taken at 40× magnification with an Olympus camera (DP71) using a Microscope Olympus SZX16 microscope with and without polarizing the light. To differentiate between the new bone and the residual allograft the allograft bone was quantified by meeting the following three criteria: (1) acellular, (2) angular in shape, and (3) illuminated under polarized light. Metamorph was utilized to complete the histomorphometry (Version 7.0.1). Histomorphometry data was obtained by using a color thresholding and an image layering technique to quantify the pixels of each layer and compare it to the total pixels in the area of interest.

Mechanical Properties

Figure 18A:
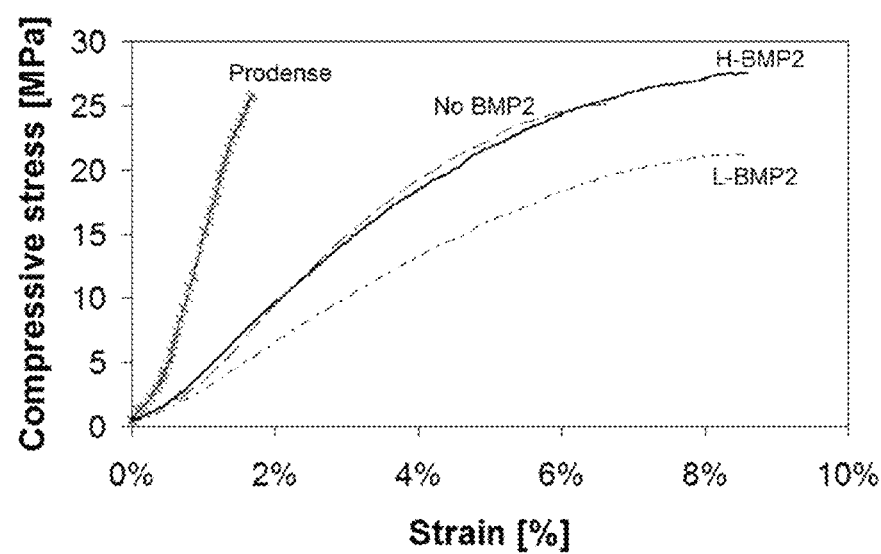
FIG. 18 shows stress-strain curves for the embodied composites (BC) and calcium phosphate cement. (A) Compression. (B) Torsion.
Figure 18B:
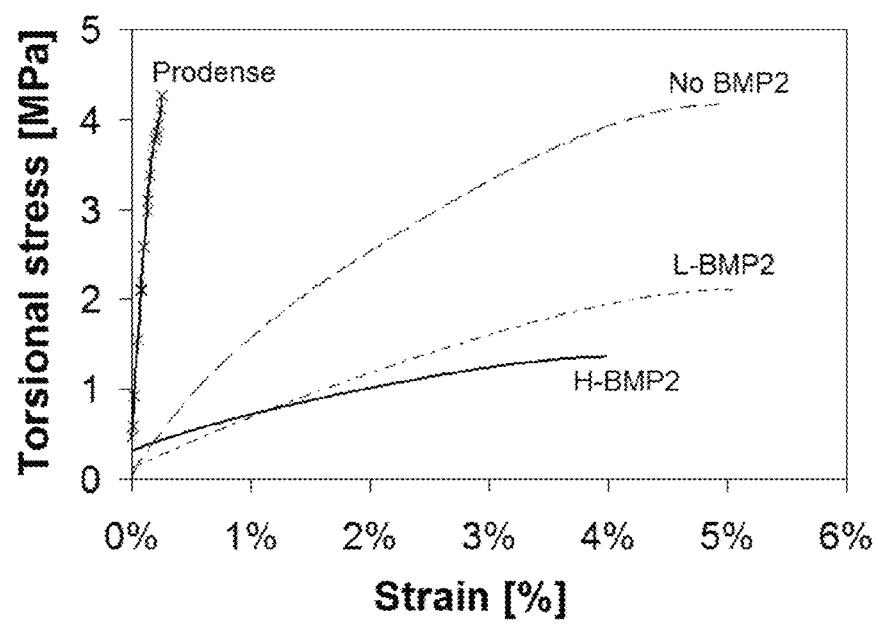

Representative compression and torsion stress-strain curves measured for the composites are shown in FIG. 18 and compared to the triphasic calcium phosphate cement Propense®. The Young's modulus, yield stress, yield strain, and energy-to-failure (area under the curve) for the biomaterials are presented in Table 1. There were no significant differences between the mechanical properties of each treatment group as the strength and modulus values ranged from 24.2-28.1 MPa and 357.3-503.0 MPa, respectively.

TABLE 1

Mechanical properties of the injectable composite with no rhBMP-2 (BC) and the calcium phosphate cement (CPC) measured under compressive and torsional loads.

| Property | CPC | BC | BMP-L | BMP-H |
|---|---|---|---|---|
| Young's modulus, MPa | 1689 ± 197 | 416 ± 86 | ± | ± |
| Stress at failure, MPa | 19.9 ± 5.1 | 22.0 ± 4.5 | ± | ± |
| Strain at failure, % | 1.67 ± 0.03 | 6.88 ± 0.24 | ± | ± |
| Energy-to-failure, kJ m$^{-3}$ | 168 ± 27 | 848 ± 138 | ± | ± |
| Young's modulus, MPa | 2051 ± 45 | 121 ± 18 | ± | ± |
| Stress at failure, MPa | 2.90 ± 1.38 | 3.60 ± 1.05 | ± | ± |
| Strain at failure, % | 0.20 ± 0.08 | 5.0 ± 1.2 | ± | ± |
| Energy-to-failure, kJ m$^{-3}$ | 4.0 ± 3.0 | 123 ± 53 | ± | ± |

Data are reported as the mean ± SEM.

μCT Data

Figure 19:
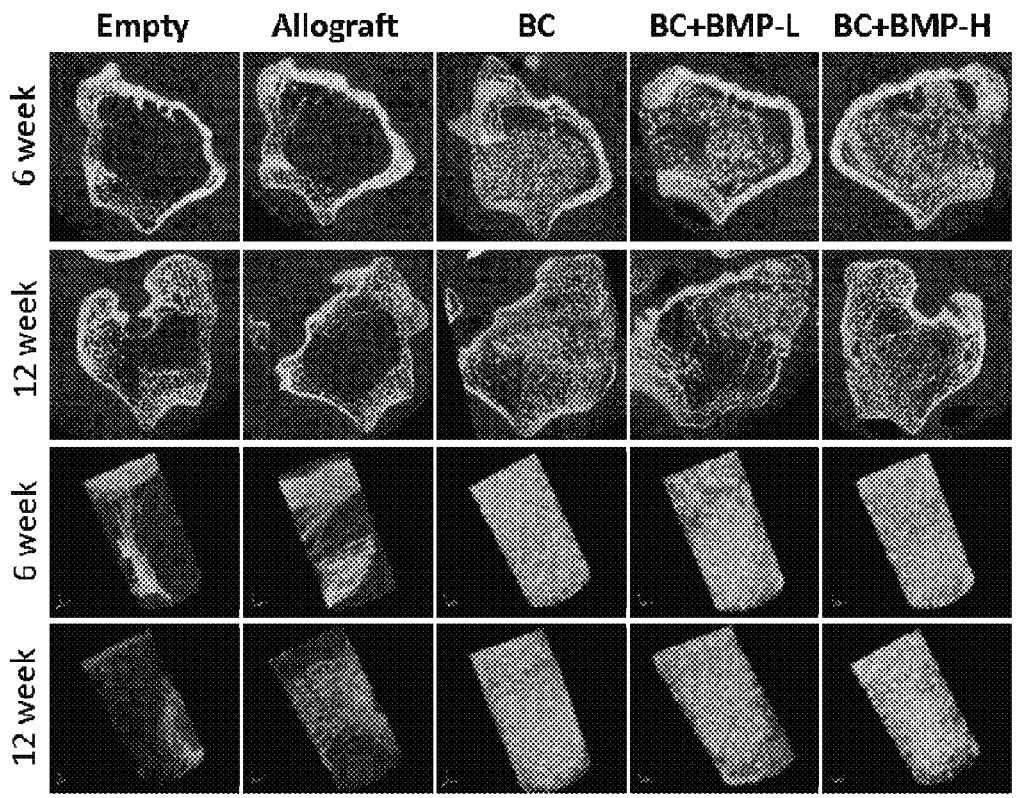
FIG. 19 shows µCT images of the empty defects and defects filled with the allograft bone particles, BC, BC+BMP-L, and BC+BMP-H at 6 and 12 weeks.

Representative μCT images of the composites and control groups after 6 and 12 weeks implantation are presented in FIG. 19. Minimal new bone formation, primarily in the region of the femoral cortex, was observed for the empty and AMBP-treated groups at 6 and 12 weeks. This data suggests that these defects did not heal and that the allograft had resorbed without the polymer binder to maintain its structure. All putty treatment groups showed evidence of resorption of allograft particles (irregularly shaped bright white particles with sharp edges) and remodeling. Incorporation of rhBMP-2 in the putty appeared to enhance remodeling of the composites.

Figure 20A:
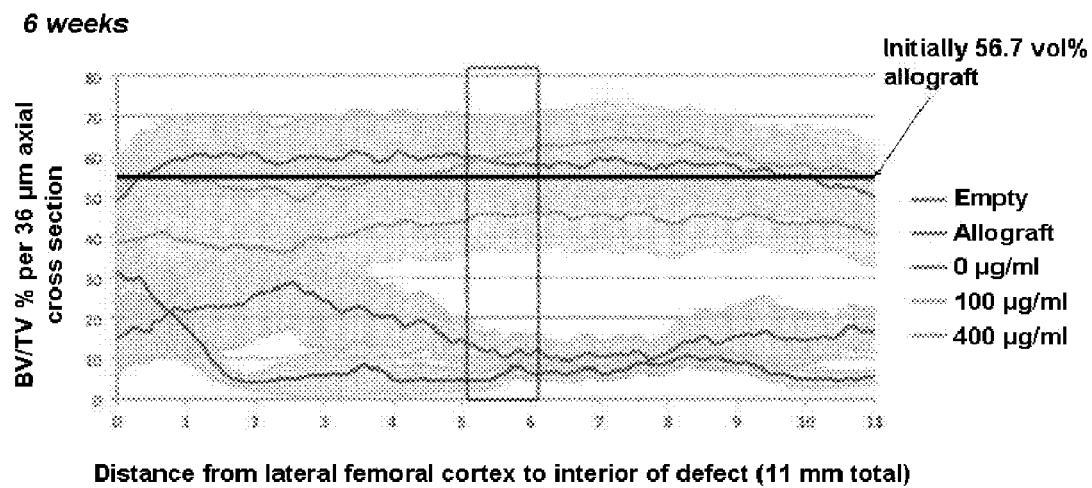
FIG. 20 shows the analysis of total bone (BV/TV) in 36-mm axial cross sections as a function of distance from the cortex measured by µCT. (A) 6 and (B) 12 weeks

The total bone content was measured by μCT for each treatment group as shown in FIG. 20. BV/TV was measured for radial cross-sections as function of distance from the cortex is shown in FIG. 20A primarily to indicate spatial regions along the defect where changes in bone volume are occurring between week 6 and week 12. In the empty treatment group at both 6 and 12 weeks, the average volume of regenerated bone in the first 2 mm from the exterior surface adjacent to the femoral cortex was greater than the average volume of regenerated bone per section within the remainder of the defect (interior 9 mm depth) adjacent to the trabecular marrow. From 6 to 12 weeks, the AMBP treatment group showed a decrease in sectional bone volume immediately adjacent to the femoral cortex indicating severe localized resorption. The AMBP/PUR composite with no rhBMP-2 showed very little variation in bone distribution from the cortex to the defect interior at both 6 and 12 weeks. At the low rhBMP2 dose, from 6 to 12 weeks an increase in bone volume was observed, whereas at the high rhBMP-2 dose bone volume in the interior adjacent to the trabecular marrow decreased with very little change in the bone volume adjacent to the femoral cortex (FIG. 20A).

Figure 20B:
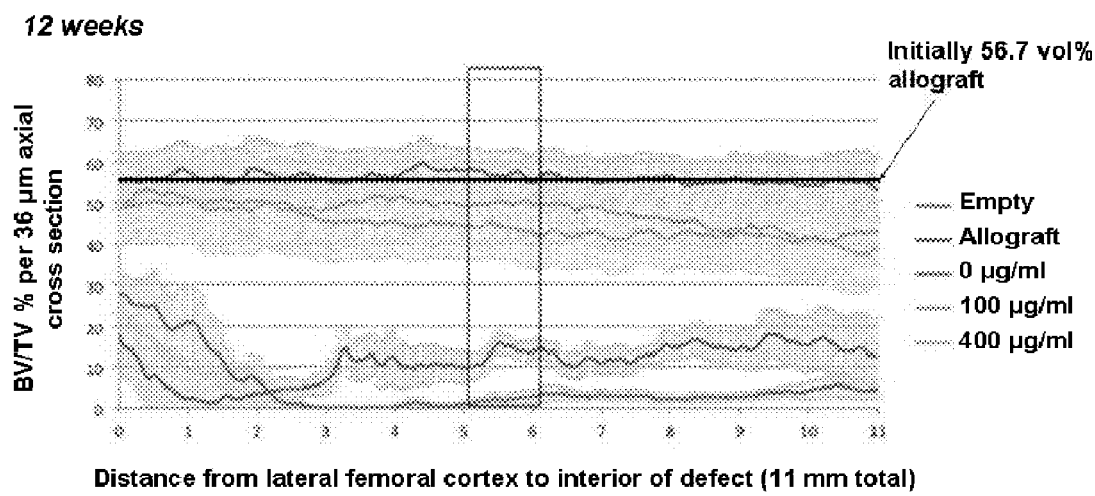

Volume-average BV/TV and TMD are shown in FIG. 20B. The BV/TV within the empty and AMBP groups was significantly lower (p<0.01) than the BV/TV in the composite groups both with and without rhBMP-2 at both time points. No significant change was observed in the BV/TV within any treatment group from 6 to 12 weeks. While there was no significant change in the TMD between all 5 treatment groups at both 6 and 12 weeks, it was observed that there was a significant increase between pre-implantation TMD and post implantation TMD at 6 and 12 weeks for the composite groups (no rhBMP2 p<0.01, 100 mg rhBMP2 p=0.05, 400 mg rhBMP2 p<0.03).

At week 0 (representing the pre-implantation architecture), a majority of the trabeculae have an average thickness of 190 mm and a very narrow distribution. All composite groups (with or without rhBMP-2) show a much broader trabecular thickness distribution with a mean thickness of 330 mm after in vivo implantation for 6 or 12 weeks. However, while the group with no rhBMP-2 shows almost no variation in thickness distribution between 6 and 12 weeks, greater changes in the percentage of trabeculae in each thickness range are observed between 6 and 12 weeks for the composites loaded with rhBMP2. In the lower dose (100 μg rhBMP-2) group, the distribution becomes uniformly broader from 6 to 12 weeks, indicating an increase in thickness of some trabeculae as well as a percentage of trabeculae with lower thickness which could be attributed to either resorption or the initialization of new ossification. In the higher dose (400 μgrhBMP-2) group, an increase in the larger trabeculae is observed with little change in the smaller trabeculae indicating a stronger appositional growth trend from 6 to 12 weeks. A rhBMP-2 dose dependent increase in bone remodeling was seen between 6 and 12 weeks with the higher dose exhibiting greater remodeling.

Histology and Histomorphometry

Figure 21:
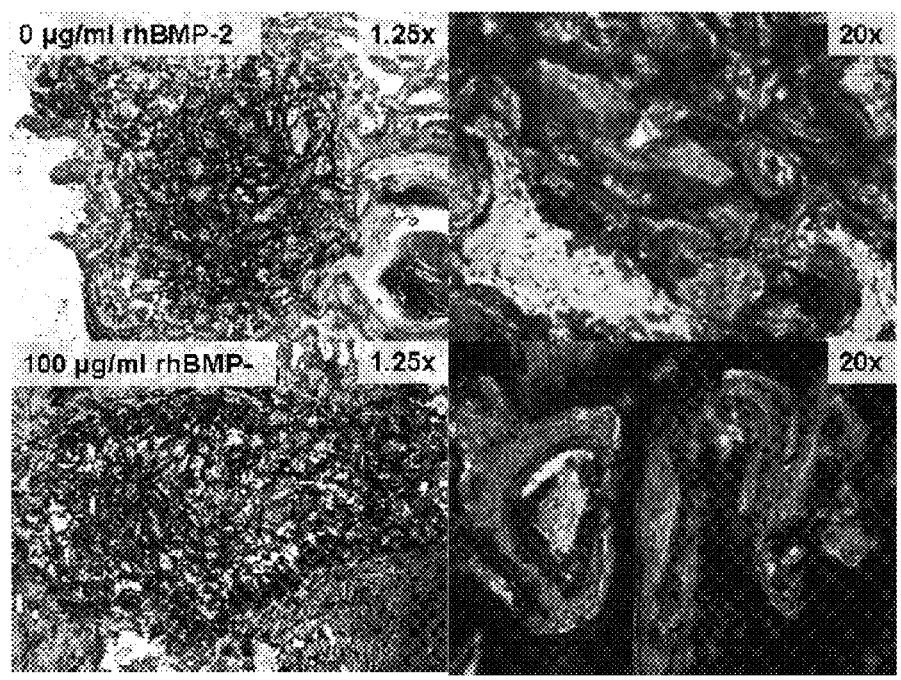
FIG. 21 shows low-(1.25×) and high-(20×) magnification images of histological sections of the BC, BC+BMP-L, and BC+BMP-H-treated defects at (A) 6 weeks and (B) 12 weeks.

Histological sections of the empty and allograft-treated defects show minimal new bone formation, which is consistent with the μCT data. In contrast, histological sections of the composite treatment groups (FIG. 21) reveal evidence of cellular infiltration (C), allograft (A) resorption, and new bone formation (NB). High magnification views show regions of active remodeling, osteoid formation, and appositional growth of new bone on residual allograft particles, suggesting that the composites remodel by creeping substitution.

Figure 22:
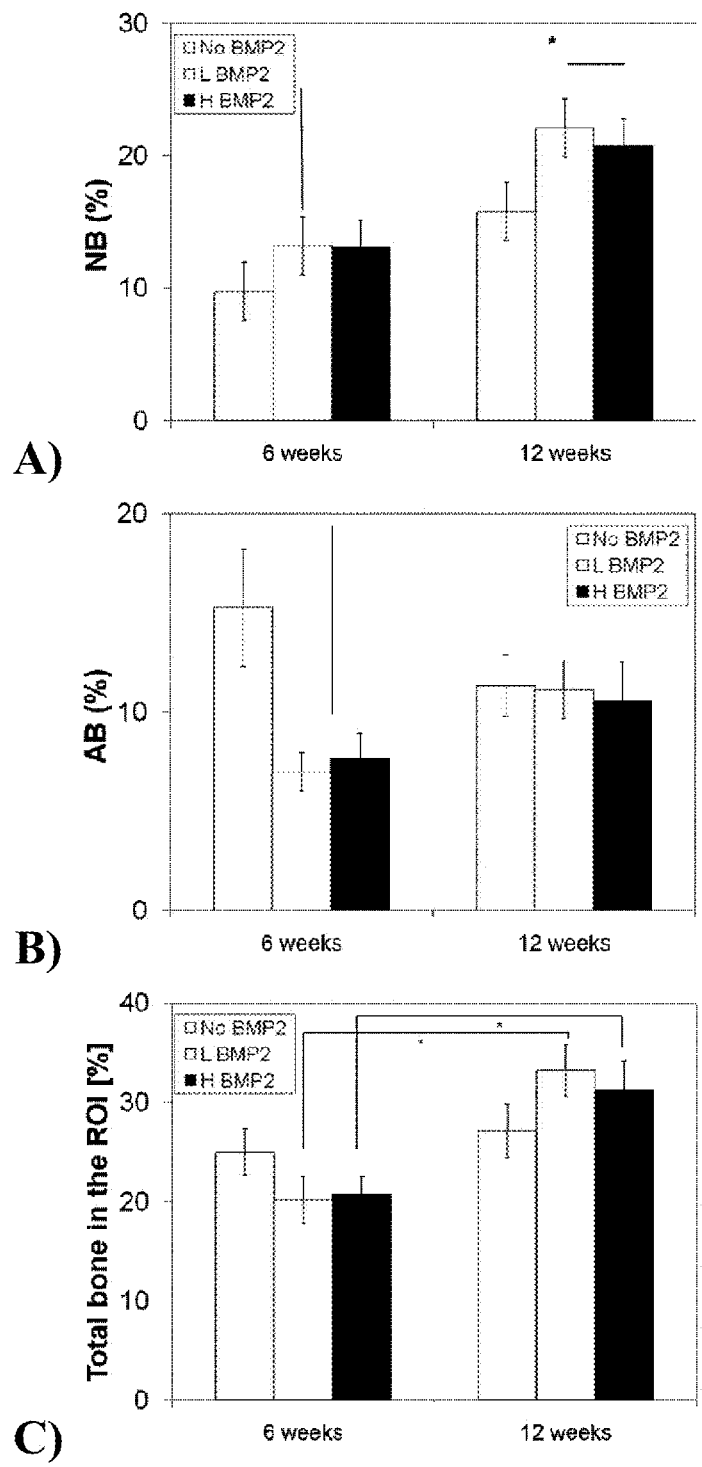
FIG. 22 shows data of a histomorphometric evaluation of composite-treated defects. (A) Area % new bone, (B) area % residual allograft, and (C) area % total bone as functions of rhBMP-2 dose at 6 and 12 weeks.

Histomorphometric analysis of the area of interest (AOI) is shown in FIG. 22 and also shows that rhBMP-2 is accelerating remodeling.

Discussion

Incorporation of rhBMP-2 enhanced new bone formation at 12 weeks relative to the composite without rhBMP-2, as evidenced by the presence of fewer allograft bone particles (irregularly shaped white particles). Similar results were observed at 6 weeks. The initial release of rhBMP-2 from the AMBP/PUR composites stimulates the differentiation of osteoprogenitor cells to osteoblasts, which subsequently regulate osteoclast differentiation through production of Receptor Activator for Nuclear Factor κB ligand (RANKL). In addition to its role of indirect regulation of osteoclasts through RANKL, rhBMP-2 can also directly stimulate osteoclast differentiation, and the concentration of rhBMP-2 must be maintained below a threshold to prevent excessive resorption.

Example 12

This Example shows the effects of stoichiometry and catalyst concentration on the reactivity, injectability, and biocompatibility of injectable PUR/allograft bone composites. The biocompatibility of the composites as well as the inflammatory response was evaluated in a rabbit femoral condyle plug defect model at 8 and 16 weeks.

Materials

See previous Examples. Bovine mineralized bone particles (B-MBP) were obtained from Medtronic, Inc (Minneapolis, Minn.). All other reagents were purchased from Aldrich. DPG was dried over 4 Å sieves before use. TEDA was dissolved in a 10% (w/v) solution with dry DPG. Excess organic material (e.g. fat) was removed from B-MBPs with a chloroform/acetone solution before use. The B-MBPs were then sieved to include only 105-500 μm particles.

Component Synthesis

The hydroxyl (OH) number of the polyester triol was measured by titration according to ASTM D4274-99 Method C, and the molecular weight was determined by gel permeation chromatography (GPC, Water Breeze). The polyester triol was composed of 60% ε-caprolactone, 30% glycolide, and 10% D,L-lactide monomers. Before use the polyol was washed with hexane dried under vacuum at 80° C. for 24 h. The % NCO of the prepolymer was measured by titration according to ASTM D2572-97. The prepolymer was maintained at 4° C. under argon prior to use. Water content for all components was determined by Karl Fischer (KF) titration with a 798 MPT Titrino with a 10 mL burette (Metrohm). Briefly, 0.5-5.0 g of material was dissolved in dry methanol. Hydranal-Composite 2 (Sigma-Aldrich), a stock KF reagent, was used to titrate the samples.

Synthesis of Composites

Composites (BCs) were prepared by adding the polyester triol, catalyst solution, and B-MBP (45 wt %) to a mixing cup, in which they were hand mixed for 30 seconds before adding the prepolymer and hand mixing for an additional 45 seconds. The composite was then loaded into a syringe. The study design in summarized in Table 2.

TABLE 2

Composite formulations.

| | I0-C0 | I0-C1 | I1-C0 | I1-C1 |
|---|---|---|---|---|
| Index | 108 | 108 | 195 | 195 |
| B-MBP (wt %) | 45.0 | 45.0 | 45.0 | 45.0 |
| Catalyst (wt %) | 0.25 | 0.50 | 0.25 | 0.50 |
| Water (wt %, measured) | 0.06 | 0.06 | 0.05 | 0.05 |
| Water (wt %, fitted) | 0.42 | 0.39 | 0.33 | 0.14 |
| LTI-PEG (wt %) | 22.4 | 21.3 | 30.2 | 28.8 |
| T6C3G1L900 (wt %) | 30.1 | 28.8 | 22.3 | 21.3 |
| DPG (wt %) | 2.3 | 4.4 | 2.3 | 4.4 |

Two catalyst weight percentages (0.50 and 0.25 wt %) and two index values (108 and 195) were utilized. The index characterizes the stoichiometry and is the ratio of isocyanate (NCO) equivalents in the prepolymer to the sum of the hydroxyl (OH) equivalents in the polyester triol and water.

ATR-FTIR Analysis of the Reacting System

Attenuated total reflectance-Fourier transform infrared spectroscopy (ATR-FTIR) measurements were conducted with a Seagull Variable Angle Reflection Accessory (Harrick Scientific) applied to a Tensor 27 FTIR instrument (Bruker). A ZnSe hemispherical crystal (Harrick Scientific) was utilized to obtain time-resolved ATR spectras. For each reaction characterized, spectra were taken every 20 to 60 seconds at a resolution of 4 $cm^{-1}$ and 56 scans per spectra. Briefly, to obtain the spectral profiles for the reactions of the composites, a given composite was synthesized and placed on a sample holder in direct contact with the bottom of the ZnSe crystal. To derive the spectral profiles for the individual component reactions of the composites, the components were mixed with the prepolymer and catalyst only. The isocyanate peak (2270 $cm^{-1}$) was deconvoluted and integrated using a MATLAB program and a calibration curve was used to correlate integrated peak values with known concentrations of isocyanate (described fully in the Supplemental Data). The analysis was completed in triplicates for each reaction analyzed.

Porosity as a Function of Water Concentration

To determine porosity as a function of water content, composites were prepared with 0-1.0 wt % added water and porosity was measured gravimetrically. Briefly, each 0.5 g batch of composites was injected via a large diameter syringe into cylindrical molds where they were allowed to react overnight at room temperature. Triplicate slices of the cylinders were cut from the fully reacted composites and measured with calipers to determine the volume. Scanning electron microscopy (SEM, Hitachi S-4200) micrographs were obtained and analyzed for pore size using MetaMorph 7.1 Image Analysis software (MDS Analytical Technologies). The mass of each slice was used to obtain the density, and the measured density was compared to the theoretical density to calculate the porosity.

In Vitro Porosity

Porosity measurements were completed for composites with index values of 108 and 195 with either 0.50 or 0.25 wt % catalyst. Composites were injected, immediately after mixing, into 2 mL of deionized water and allowed to react overnight in an incubator at 37° C. At least three cylindrical cores were taken from each sample and analyzed gravimetrically to obtain porosity as described above.

Rheology of Curing Composites

The rheological profiles during cure were measured for each composites in situ with an AR 2000ex rheometer with a Rheology Advantage AR Controller (TA Instruments). Continuous oscillation measurements were conducted at 1 Hz and 1% strain with 25 mm disposable parallel plates and a 1 mm gap. Measurements for each configuration of composites were taken with either dry conditions or submerged in water via a submersion assembly kit (TA Instruments). Initial viscosities ($\eta'_i$) and working times (gel points, $\tau_w$) were tabulated.

Characterization of Intermediates Leached from the Reactive Composites

In order to determine whether cytotoxic reactive intermediates leach from the composites during cure, in vitro leaching experiments were performed. Briefly, 2.5 g of each composites were injected into an empty vial, and after 2 min (after mixing was started) 5 ml PBS was added to the vial. For the second time point, 2.5 g of each composites were injected into a sample cup and transferred to a vial filled with 5 mL of PBS after 45 min post-mixing. For the leachate cytotoxicity experiments (Section 2.9), leachates were collected in α-minimum essential medium (α-MEM) with 10% (v/v) fetal bovine serum (FBS) and 1% (v/v) penicillin/streptomycin using the procedure described above. The samples were maintained at 37° C. for 72 hours, at which time the PBS was removed, the pH measured, and the samples subsequently lyophilized and weighed. After reconstitution in solvent, the composition of the residue was characterized by NMR. The spectra were compared to those of the pure components in the composites to determine the presence of individual components in the leachates.

The cytotoxicity of the leachates from the composites was measured using MC3T3-E1 embryonic mouse osteoblast precursor cells in vitro. Cells were seeded in a 96-well plate with a density of $5\times10^3$ cells per well and cultured in α-MEM with 10% (v/v) fetal bovine serum (FBS) and 1% (v/v) penicillin/streptomycin in a $CO_2$ incubator with 5% $CO_2$ at 37° C. The concentration of the leachates varied from 6.15% (16× dilution with serum medium) to 100% (1×). The culture medium was changed every 2 days. Trypsin-EDTA was used for dissociation of MC3T3-E1 cells. The cells were analyzed for viability using a Live/Dead Viability kit (Invitrogen). The assay was completed as recommended by the manufacturer's instructions. Cells were analyzed after 24 hours exposure to the leachate solution. Triplicates for each group were analyzed with control groups treated with blank PBS. All experiments were conducted in accordance with ISO-10993-5.

In Vivo Biocompatibility and New Bone Formation in a Rabbit Femoral Condyle Plug Defect Model Eighteen New Zealand White (NZW) rabbits weighing between 4.0 and 5.4 kg were used in this study. All surgical and care procedures were carried out under aseptic conditions per the approved IACUC protocol. The components of the composites were gamma-irradiated using a dose of approximately 25 kGY. Glycopyrrolate was administered at 0.01 mg/kg IM followed by ketamine at 40 mg/kg IM. Bilateral cylindrical defects of approximately 5 mm diameter by 11 mm in depth were drilled in the metaphysis of the distal femurs of each rabbit under copious sterile saline irrigation using a trephine in a MicroAire handpiece. Materials from each treatment group were subsequently injected into each defect using a syringe, made flush with the cortical surface and allowed to harden. Closure was attained using a 3-layered approach comprising muscle, fascia, and subcuraneous 3-0 Vicryl sutures. Skin glue was applied topically to maintain closure. Treatment groups for each composite were dispersed randomly among the rabbits. The rabbits were euthanized at both 8 and 16 week time points using Fatalplus (1 mL/4.5 kg) intravenously.

μCT Analysis. See Previous Examples.

Histology

Harvested femoral condyles were fixed in 10% neutral buffered formalin at room temperature for one week. The samples were then decalcified in hydrochloric acid, dehydrated and embedded in paraffin. After embedding, the samples were then sectioned onto slides at 4 microns thick and stained using hematoxylin/eosin (H & E stain). Ground sections were also prepared by immersing the femora in a solution of 10% formalin for two weeks followed by a series of ethanol dehydrations. After fixation, the femurs were embedded in poly(methyl methacrylate) and 200-□m sections were cut from the resulting blocks using an Exakt band saw. The sections were then ground and polished using an Exakt grinding system to less than 100 □m and stained with Sanderson's rapid bone stain counterstained with van Gieson. Residual allograft bone particles stained light brown, residual polymer stained black, new bone stained pink with dark blue osteocytes within the matrix, red blood cells stained turquoise, and other cells stained a lighter blue.

Thin (5 μm) histological sections stained with H&E were evaluated using a subjective scoring system. Inflammation, granulation tissue, reactive bone formation, marrow edema, and synovitis were all evaluated on a scale of 0-5 (0=normal, 1=minimal, 2=mild, 3=moderate, 4=marked, and 5=severe). The samples were also given an overall effect score in which the following criteria were evaluated: (1) no discernible defect, (2) visible circular defect surrounded by a complete to vague circle of bone filled with fat and marrow elements, and (3) a circular area of dropout, surrounded by proteinaceous fluid and a thin rim of new bone with minimal to mild inflammation.

Reactivity of PUR Composites

The individual components of the composite (polyester triol, DPG, B-MBP, and water) were analyzed for their reactivity with the NCO-terminated prepolymer. The conversion of NCO equivalents in the prepolymer was monitored in situ by ATR-FTIR, which was analyzed to obtain the second-order rate constants for each reaction at each catalyst level. The same technique was applied for the overall reaction of the composite at two different indices and catalyst levels.

Concentration of NCO equivalents versus time for the overall composite reaction, polyester triol concentration, DPG concentration, and B-MBPs concentrations, at high (0.50 wt %) and low (0.25 wt %) catalyst concentration, were monitored. Each of the reactions was found to follows a second-order mechanism as anticipate, and thus the slope of line is equivalent to the rate constant for each of the reactions. Water has the highest reactivity compared to the other reactions, regardless of catalyst concentration. The polyester triol is approximately 20 times less reactive than water for the higher catalyst level, while the DPG is approximately 3 times less reactive than the triol. The reactivity of the B-MBPs is the lowest of all the components at both catalyst levels.

Based on the rate constants of the individual components, a kinetic model was developed to predict the overall reactivity of the composites. The equivalent balance equations were then solved to calculate the concentration profiles of each component as a function of time.

Using the fitted rate constants and the initial concentration of equivalents, the overall conversion of NCO equivalents in the composite was plotted and compared to the experimental values. Due to difficulties associated with accurately measuring the concentration of water in the polyester triol, catalyst solution, and prepolymer, the initial water concentration was used as a fitting parameter. The water concentrations measured by titration varied from 15 to 36% of the fitted values. While the water conversion approaches 100% after approximately 10-20 minutes, the conversions of the other components are less than 100%, and decrease with decreasing index.

Effect of Water on Composite Porosity

Reaction of the NCO-terminated prepolymer with water yields carbon dioxide gas, which acts as a blowing agent resulting in the formation of pores. The porosity of the composites as a function of total water increases with water concentration up to a plateau value of 60 vol % independent of the catalyst level or index. Using SEM, it was observed that composites at 0.2, 0.4, and 1.0 total wt % water have pore diameter, porosity, and interconnectivity increase with water concentration. While the pores are predominantly closed at the lower water concentrations, they appear to be more interconnected at 1.0 wt % water. It was observed, pore diameter is independent of index and catalyst concentration and increases with total water concentration, but the differences are not significant.

Under in vivo conditions, water from the wound bed can diffuse into the composite, resulting in increased expansion and porosity. The effects of water diffusion were simulated in an in vitro test where the composites are reacted in an aqueous environment. At the lower catalyst concentration, both indices yield composites with porosities of 48-55%, and at the higher catalyst level the index 210 composites results in 50% porosity. Thus the porosities obtained under wet cure exceed those obtained from dry cure (9-20%). In contrast, the index 115 composite has a porosity of 22%, which is comparable to the 17% porosity measured for the composite cured under dry conditions with no added water. These observations suggest that diffusion of water from the wound bed can significantly increase expansion, particularly at the low catalyst concentration and high index.

Characterization and Cytotoxicity of Leachates In Vitro

NMR spectra for the leachates from I0-C1 composite injected into PBS at 2 and 45 minutes after mixing were compared to spectra for the individual components to determine which components were leaching from the reactive polymer at time points corresponding to the cream (2 min) and tack-free (45 min) stages of cure. The other composites had nearly identical spectral profiles to that of I0-C1. The peak at 2.3 ppm associated with the proton adjacent to the carbonyl group in the polyester appears in the spectra of the leachates collected at 2 and 45 min, suggesting that unreacted polyester triol had leached into the medium. Similarly, the peak at 1.0 ppm associated with the protons on the methylene carbon group in DPG also appear in the leachates at both time points, indicating that unreacted DPG had diffused into the medium. In contrast, the prepolymer was uniquely distinguished by a series of peaks above 6 ppm, none of which appeared in the spectra for any of the leachates, suggesting that the prepolymer did not leach into the medium. Gravimetric analysis of the leached composites revealed a 0.2-1.2% mass loss due to diffusion of individual components from the composites into the buffer. The pH of the leachates recovered at 2 and 45 minutes varied from 6.6 to 6.8 compared to the initial value of 7.35.

MC3T3-E1 murine osteoprogenitor cells were treated with leachates from the composites collected at 2 and 45 min and diluted with serum medium such that the final concentration of leachates ranged from 6.25% (16× dilution) to 100% (1× dilution). Cells were cultured for 24 h. Leachate dose-response curves measured for leachates collected at 2 and 45 min reveal the anticipated sigmoidal shape. Furthermore, three of the eight treatment groups showed cytotoxicity, which is defined as <70% viability. For the three treatment groups showing cytotoxicity, the dilution factors required to render the culture medium non-cytotoxic varied from 1.60-1.81. For a specific composite composition and dilution factor, the percentage of viable cells was generally higher for leachates collected at 45 min (except for the 1× dilution for I1-C1), which is consistent with the notion that the concentration of leachates was lower at 45 min due to the higher conversion. Using cell culture on tissue culture polystyrene stained with calcein, and a mesenchymal phenotype was observed when treated with leachates from composite I0-C1 collected at 2 and 45 min and diluted 8× with serum medium. Control cells treated with PBS show a similar morphology.

Rheological Properties of Composites.

Working times varied from 7-29 min, and decreased with increasing catalyst concentration and index. Similarly, initial viscosities ranged from 90-900 Pa*s, and increased with increasing catalyst concentration and index. Working time and initial viscosity measured under wet conditions were generally within 15% of values measured for dry conditions.

In Vivo Inflammatory Response and Remodeling in a Rabbit Femoral Plug Model

Results from the histological scoring of H&E sections at both 8 and 16 weeks show that the defects in the control (empty defect) treatment group had a central area of fat and hematopoietic elements surrounded by a variably vague circle of bone and trabeculae. There appeared to be very little inflammation within the control group. At 8 weeks, defects treated with the I0-C1 composite consisted of non-viable bone fragments surrounded by osteoclasts, osteoblasts, new trabeculae, and marrow elements. There was mild to moderate inflammation and edema surrounding and within the area of the defect. At 16 weeks, the composite group defect contained no non-viable bone fragments, fewer new trabeculae, and decreased inflammation and edema.

Discussion

The biocompatibility of the I0-C1 formulation that showed the most predictable performance under wet conditions was evaluated in a rabbit femoral condyle plug defect model at 8 and 16 weeks, which showed cellular infiltration, new bone formation, complete resorption of the polymer at 16 weeks, and a mild inflammatory response.

The water reaction is referred to as the blowing reaction due to the production of carbon dioxide, which creates pores in the composite. Thus the water reaction can be exploited to generate >50 µm pores in the composite to accelerate cellular infiltration. To balance the requirements for both mechanical strength and cellular infiltration, expansion of the composite must be controlled such that porosity <55 vol %. The porosity of the I0-C0, I1-C0, and I1-C1 with no added water increased from 8-20% under dry conditions to 50-55% under wet conditions. These observations suggest that formulations I0-C0, I1-C0, and I1-C1 undergo unpredictable expansion in vivo.

Over-expansion due to diffusion of external water may be mitigated by the choice of catalyst. Due to the cytotoxicity of heavy metal urethane catalysts (e.g., dibutyl tin dilaurate), tertiary amine catalysts have been investigated for synthesis of biodegradable polyurethanes. While tertiary amines are known to catalyze both the gelling (polyester triol) and blowing (water) reactions, TEDA is known as one of the strongest amine gelling catalysts. However, despite the relatively strong gelling activity of TEDA, the water reaction was the fastest for both catalyst levels. More potent gelling catalyst with moderate toxicity, such as ferric acetylacetonate, may limit the effects of water in composites.

While formulation I0-C1 minimized the effects of external water on expansion, the lower index resulted in a lower conversion of polyester and DPG. The rheology data suggest that after 60 min the composites have formed a crosslinked network.

At the early stages of the curing process before the gel time, the NCO conversion is low (e.g., 10-20% at 2 min), and thus leaching of reactive intermediates may occur. However, neither prepolymer nor TEDA was identified in NMR spectra leachates at any conditions, and only a small amount (e.g., <2%) of polyester and DPG were leached from the composites at both 2 and 45 min. These observations are consistent with the predictions of the kinetic model, which showed that the conversion of polyester triol and DPG were highest in the I1-C1 materials (96% and 68%, respectively) and lowest in the I1-C0 materials (35% and 47%, respectively). When diluted 8:1 with fresh buffer, the leachates had no adverse effect on cell viability. Thus injectable PUR composites minimize the risk of releasing cytotoxic catalysts, solvents, or reactive intermediates to the surrounding tissue.

Lowering the index and increasing the catalyst concentration may allow one to limit porosity can be limited to below 30% when injected into an aqueous environment, ensuring good mechanical and wound healing properties. The reacting composites have been found to leach low amounts of non-cytotoxic products during the curing process.

Example 13

Delivery of rhBMP-2 combined with allograft may result in transient resorption. β-Tricalcium phosphate (β-TCP) is a biocompatible, resorbable ceramic that has been used effectively as a substitute for allograft bone. In the present Example, the ability of an injectable PUR/β-TCP composite with rhBMP-2 to heal bone defects is shown.

The biodegradable polyurethane was synthesized from a lysine triisocyanate (LTI) prepolymer and polyethylene glycol (PEG), a polyester triol (900 g/mol), and triethylene diamine catalyst. The prepolymer, polyester, and β-TCP were mixed in a mixing cup by hand for 60 seconds. The mixture was then transferred to a vial containing the lyophilized rhBMP-2 powder, the catalyst added, and the resulting paste hand-mixed for an additional 60 seconds. Composites were injected into 8-mm critical-size calvarial defects in rats. Animals were sacrificed at 4 weeks and new bone formation evaluated by radiographs, μCT, histology, and histomorphometry. Treatment groups included the composite containing 45% TCP with and without 200 μg/mL rhBMP-2. Pores were generated by the reaction of water in the composite with the NCO-terminated prepolymer, resulting in the formation of carbon dioxide gas. The porosity of materials cured in vitro was compared to that of samples injected in vivo gravimetrically and using SEM analysis.

Figure 23:
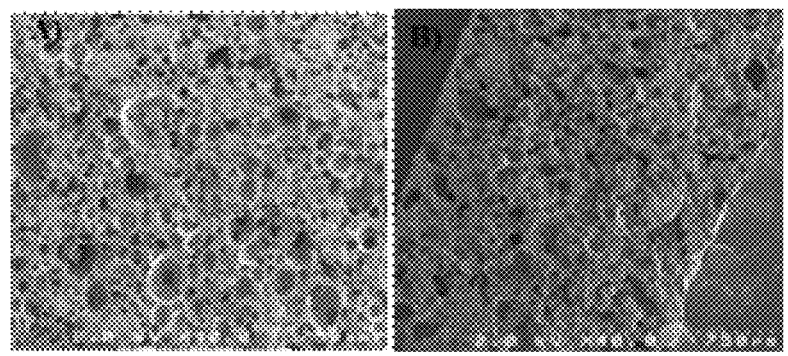
FIG. 23 shows SEM images of PUR/β-TCP composites embodiments (A) in vitro and B) in vivo.
Figure 24:
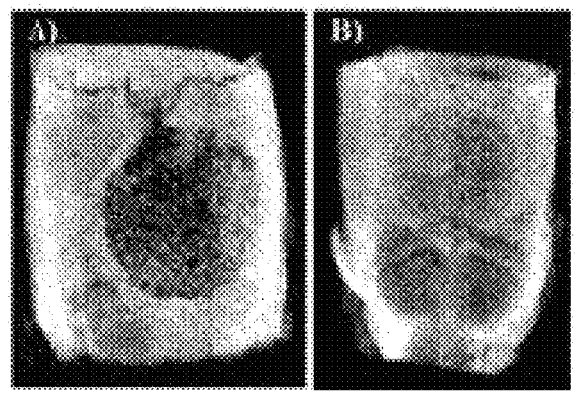
FIG. 24 shows Faxitron data at 4 weeks for embodiments of PUR/β-TCP composites A) without rhBMP-2 B) with rhBMP-2.
Figure 25:
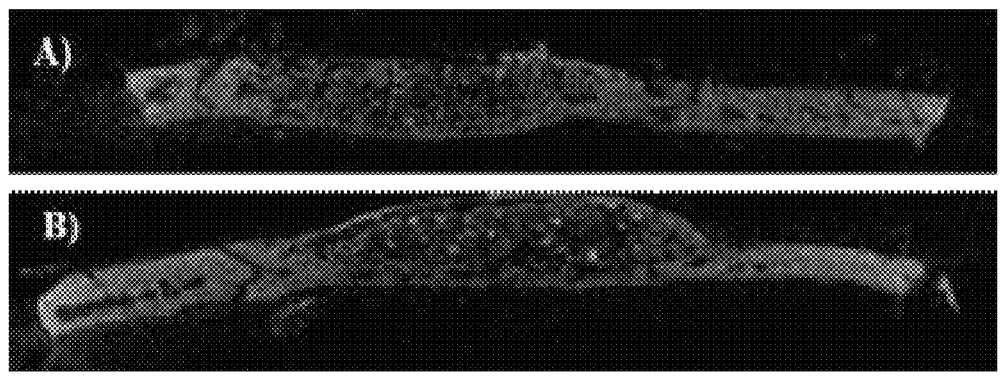
FIG. 25 shows µCT data at 4 weeks for embodiments of PUR/β-TCP composites A) without rhBMP-2 B) with rhBMP-2.

The porosity of bone grafts is important for control of rhBMP-2 release and cellular infiltration. SEM images of composites cured under in vitro (A) or in vivo (B) conditions are shown in FIG. 23. The porosity of composites injected in vivo ranged from 40-50%, which was comparable to that of materials cured in vitro. Thus, the effects of diffusion of water from the wound bed under in vivo conditions did not adversely affect cure of the composite, resulting in predictable cure. Representative μCT images taken at 4 weeks (FIG. 24) show that the injected composite completely filled the defect for samples with and without rhBMP-2 (n=13 per group). In the composites without rhBMP-2, there is evidence remodeling near the perimeter of the graft in contact with host bone, as suggested by the increased density (white color) near the host bone interface. Addition of rhBMP-2 resulted in both new bone formation as well as bridging of the defect with new bone at 4 weeks (FIG. 25B). These observations suggest that the composites supported cellular infiltration and remodeling, and that rhBMP-2 enhanced healing.

Example 14

This Example illustrates that for certain embodiments of the present invention remodeling is superior when the composite comprises allograft particles, or any other synthetic substitute particles, having a particle size of at least 100 μm.

Figure 26:
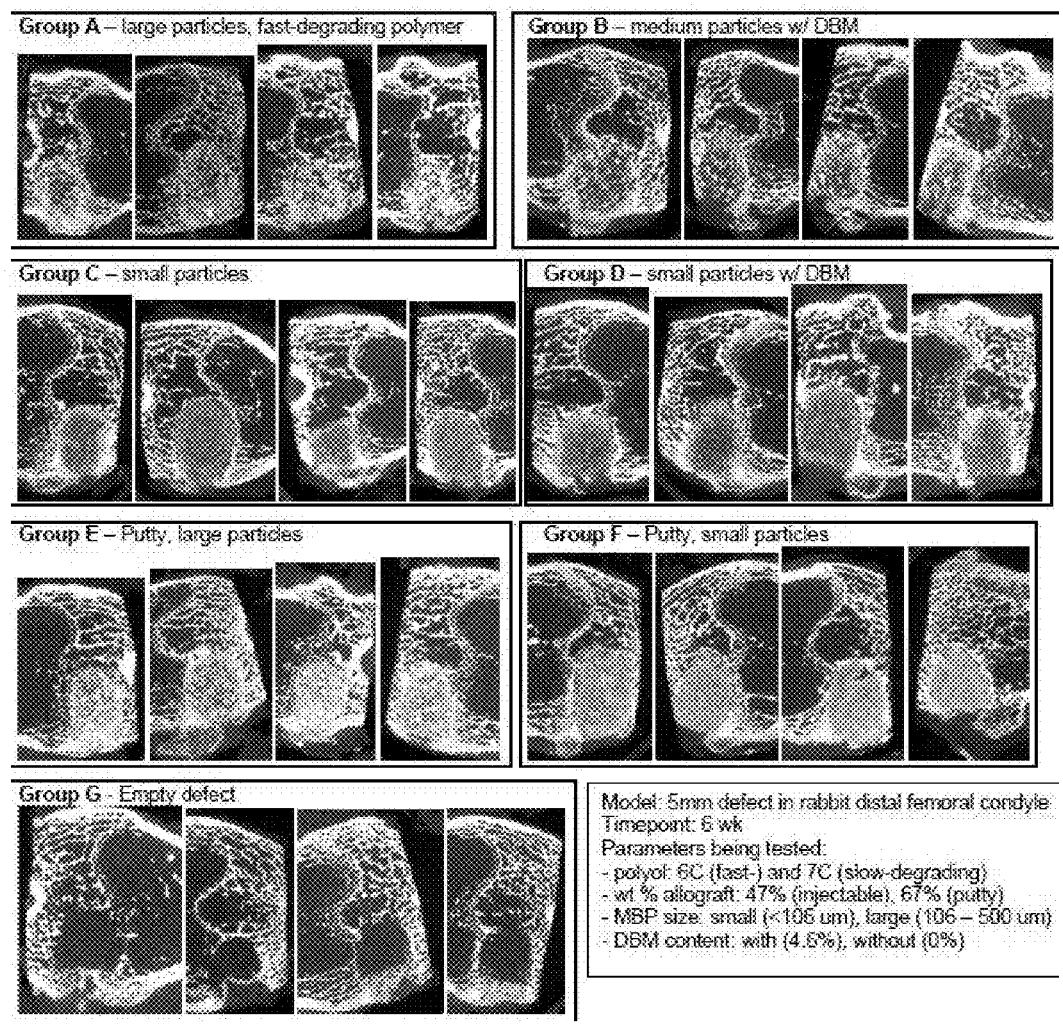
FIG. 26 shows µCT data for various embodiments of the present invention comprising small (<106 µm) and large (106-500 µm) mineralized bone particles.

Shown in FIG. 26 are μCT scans of both injectable, porous embodiments (47 wt % allograft) and moldable embodiments (67 wt % allograft) used in a 5 mm defect in a rabbit distal femoral condyle at week 6. The polymers tested are shown in Table 3, below.

TABLE 3

Tested embodiments for μCT analysis of remodeling.

| Group | Injectable or Putty | Allograft wt % | Mineralized particle ∅ range (μm) | DBM content (wt %) | Polyol | 6 wks n = | 12 wks n = |
|---|---|---|---|---|---|---|---|
| Group A | Injectable | 47 | 106-500 | 0 | 6C | 4 | 4 |
| Group B | Injectable | 47 | 106-500 | 4.6 | 7C | 4 | 4 |
| Group C | Injectable | 47 | <106 | 0 | 7C | 4 | 4 |
| Group D | Injectable | 47 | <106 | 4.6 | 7C | 4 | 4 |
| Group E | Putty | 67 | 106-500 | 0 | 7C | 4 | 4 |
| Group F | Putty | 67 | <106 | 0 | 7C | 4 | 4 |
| Group G | (Empty defect) | N/A | N/A | N/A | N/A | 4 | 4 |

The μCT images in FIG. 26 depict that remodeling for certain embodiments is superior in embodiments comprising larger particles sizes. Thus, for certain embodiments of the present invention is preferable to include a resorbable osteogenic matrix, whether it be allograft or synthetic allograft, that has relatively large particles sizes, including, for example, particles sizes of at least about 100 μm.

Example 15

In this Example, the effects of Bioglass 45S5 (BG) surface modification on the bioactivity and mechanical properties of PUR/BG composites are investigated. Prior to reaction with the PUR binder, BG particles were functionalized with the silane coupling agent 3-aminopropyl-triethoxysilane (APTES), which has been shown to increase the mechanical compressive strength of BG, as well as surface grafting of polycaprolactone (PCL) to enhance interfacial bonding.

Materials & Methods

Surface modification of BG with APTES and PCL (from ε-caprolactone monomer and $Sn(Oct)_2$ catalyst) was based on known protocols. A flat BG disk model was utilized to evaluate the effect of the surface modifications on the properties of the BG used in the PUR composite. The disks were characterized by contact angle and X-ray photoelectron spectroscopy (XPS). In order to test bioactivity, BG disks were immersed in simulated body fluid (SBF) for various amounts of time over a 14 day period. Bioactivity was assessed by measuring the formation of hydroxylcarbonate apatite using wide-angle X-ray diffraction, scanning electron microscopy, and energy-dispersive x-ray spectroscopy (EDS). Cylindrical composites were prepared from a lysine triisocyanate-poly(ethylene glycol) prepolymer, triethylene diamine catalyst, PCL triol (Mn ~300 g/mol), and BG (46.3 volume %). Mechanical testing was completed in compression mode.

Results & Discussion

The presence of APTES and PCL (via Sn(Oct)$_2$) on the surface of the BG disks was detected via XPS based on the presence of the N1s (5.02 at. %) and Sn3d (0.35 at. %) spectra, respectively. A change in advancing contact angle compared to unmodified bioglass was observed. The contact angles for unmodified, silanized, and PCL surface-modified BG disks were 19±3°, 45±3°, and 66±1.73°, respectively. EDS was used to calculate the Ca/P ratio and compared to the value of apatite (1.67), as an indicator for complete coverage of the surface with apatite. As shown in Table 4, Ca/P for unmodified BG at 7 days was smaller compared to PCL-modified BG.

TABLE 4

Ca/P of BG disk surface after immersion in SBF

| Time (days) | Unmod. BG | PCL-mod. BG |
| --- | --- | --- |
| 0 | 5.80 | 5.67 |
| 7 | 2.09 | 2.19 |
| 14 | 1.67 | 1.66 |

Ratio based on Ca and P atomic percent, obtained from EDS

From this result, it appears that the bioactivity of PCL-modified BG was slightly delayed compared to unmodified bioglass. PUR composites incorporating unmodified BG exhibited an ultimate yield strength and Young's modulus of 4.01±0.53 MPa and 46.26±2.97 MPa, compared to 58.49±5.32 MPa and 2185.71±422.75 MPa, respectively, for PCL-modified BG composites. Thus, the overall mechanical properties of PUR/BG composites are dramatically improved with the use of PCL-modified BG particles compared to unmodified BG. The increase in strength is attributed to improved adhesion between the BG and PUR phases due to the similar contact angles (66° for the PCL-modified BG compared to 66° for the PUR phase). Furthermore, the OH-terminated PCL chains are anticipated to react with the NCO groups in the LTI-PEG prepolymer, resulting in increased covalent binding. A dose-response experiment is ongoing to identify the surface coverage of grafted PCL that maintains the desired bioactivity of the BG particles while also attaining the mechanical properties required for functionally weight-bearing bone grafts.

BG particles modified by treatment with APTES and subsequent PCL grafting exhibit contact angles comparable to that of the lysine-derived PUR binder. Grafted PCL increased the compressive modulus and strength of PUR/BG composites by an order of magnitude, and only slightly delayed biomineralization in vitro by 7 days. However, by 14 days, the Ca/P ratio of the mineralized surface layer on PCL-modified BG disks was comparable to that of HA (1.67), suggesting that while surface modification delays the rate of apatite formation on the BG surface when in SBF, it does not block the bioactivity of the material.

Example 16

This Example further characterizes embodiments of modified BG and PUR/BG composites.

2.1 Materials

Melt-derived 45S5 bioactive glass particles (150-212 μm diameter) and rods (10 mm diameter by 50 mm length) were purchased from Mo-Sci Corp. (Rolla, Mo.). APTES, ε-caprolactone, tetrahydrofuran, dipropylene glycol (DPG), PCL triol ($M_n$ ~300 g mol$^{-1}$), deuterated dimethyl sulfoxide (DMSO), and iron (Fe) (III) acetylacetonate (FeAA) catalyst were purchased from Sigma-Aldrich (St. Louis, Mo.). Magnesium sulfate, stannous octoate (Sn(Oct)$_2$), and phosphate-buffered saline (PBS) were acquired from Thermo Fisher Scientific (Waltham, Mass.). Technovit 4000 (Heraeus Kulzer) was purchased from Electron Microscopy Sciences (Hatfield, Pa.). SiO$_2$ wafers were purchased from University Wafer (South Boston, Mass.). Triethylenediamine (TEDA) was purchased from Evonik (Parsipanny, N.J.). The lysine triisocyante (LTI)-polyethylene glycol (PEG) prepolymer (21% NCO) was supplied by Ricerca Biosciences (Painesville, Ohio).

2.2 Surface Modification of BG

In order to obtain a sufficiently smooth surface for the techniques used to characterize the bioactive glass surface, melt-derived 45S5 bioactive glass disks were utilized to model the surface of the bioactive glass particles within the BG/PUR composite. 3-mm thick disks were obtained by cutting bioactive glass rods with a Buehler® IsoMet® Low Speed saw. The disks were polished with silicon carbide paper under aqueous conditions until an average roughness ($R_a$) below 1 μm was obtained. The surface roughness was measured by a Veeco Dektak 150 Stylus Surface profilometer (Plainview, N.Y.). The bioactive glass particles were not subjected to any physical manipulation once received from the manufacturer, thus its geometry and structure were not altered in any manner.

The BG particles and disks were then cleaned (26). BG was sonicated for 5 min in a solution of acetone in deionized (DI) water (95 volume %) at room temperature, followed by rinsing in DI water under sonication for 5 min. A total of three washing cycles were performed. The BG was then silanized with APTES by subjection to a 2 μM solution of APTES in 9:1 (v/v) ethanol:DI water under intense mixing for 5 h (28). The material was then rinsed with ethanol and thermally treated at 100° C. for 1 h. For the surface modification of the BG disks, the same process was used only that the contact with the APTES solution was stationary. The disks were subjected to the same post-silanization treatment.

Figure 27:
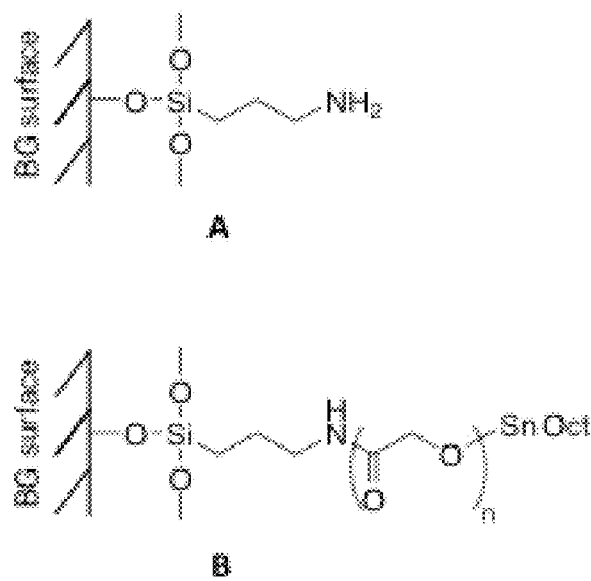
FIG. 27 shows a schematic of biolgass surface modifications showing (A) APTES silanol group, and (B) a PCL chain attached to pre-attached silanol via surface-initiated ring-opening polymerization.

For surface-initiated ROP of PCL, ε-caprolactone was dried in the presence of magnesium sulfate particles prior to use. A reaction mixture was prepared with Sn(Oct)$_2$ and ε-caprolactone at a molar ratio of 1:1000 (29, 36). A weight ratio of 0.83:1 was used for silanized-BG particles to ε-caprolactone. The mixture was allowed to react under constant mixing agitation at 110° C. for sufficient periods of time to yield the targeted number average molecular weight ($M_n$) (low=8 kDa and high=25 kDa) of the "grafting-from" PCL. For the BG disks, the same reaction mixture was utilized but under static conditions. The poly(ε-caprolactone) (PCL)-modified BG particles were extracted upon termination of the reaction via chloroform solvation of the non-grafted PCL. All material was then dried at 40° C. for 24 h. A schematic illustrating the products of the silanization and polymerization reactions are shown in FIG. 27.

2.3 Thermogravimetric Analysis (TGA)

Thermogravimetric analyses were performed with a heating at a rate of 10° C. min$^{-1}$ over the temperature range of 25-600° C., under a nitrogen flow of 40 mL min$^{-1}$. A TA Instruments Q500 instrument with the corresponding TA Instruments Universal Analysis 2000 (Version 4.5A) software was used. The sample masses were 20 mg.

2.4 X-Ray Photoelectron Spectroscopy (XPS)

XPS measurements were performed using an ULVAC-PHI 5000 VersaProbe spectrometer (Kanagawa, Japan). Dried BG disk specimens were irradiated with a 25 W monochromatic Al Kα x-ray beam (1486.6 eV) and a 100-µm spot size. An electron neutralizer of 1.1 eV and an Ar+ ion neutralizer of 10 eV were used to counteract charging effects. XPS survey scans were accumulated over a binding energy range from 0-1300 eV, with a pass energy of 187.85 eV and a take-off angle of 45°. The obtained data were processed using CasaXPS Version 2.3.15 software to calculate the atomic percentages.

2.5 Ellipsometry

Dry ellipsometric thicknesses on $SiO_2$ wafers were determined from a J. A. Wollam XLS-100 variable angle spectroscopic ellipsometer. Thicknesses were fit to data taken at 75° from the surface over wavelengths from 200 to 1000 nm. The sample surface was modeled as a Si substrate with a native oxide layer and a Cauchy layer. The thickness of the oxide layer was measured from a water and ethanol-cleaned silicon-oxide wafer each time samples were prepared. The thickness of the film was calculated using the software's 'Cauchy film' fit.

2.6 Atomic Force Microscopy (AFM)

A Jeol JSPM-5200 was used to obtain AFM images of surface-modified $SiO_2$ wafers under ambient laboratory environment. Images (5 µm squares) were obtained using a Si cantilever in AC (tapping) mode, plane-fitted and filtered to remove noise, and processed using Gwyddion software.

2.7 Gel Permeation Chromatography (GPC)

A Waters Breeze GPC (Milford, Mass.) was used to measure the number average molecular weight of the bulk polymer synthesized in the surface-initiated reactions. It was assumed that the bulk polymer approximates the molecular weight of the grafted polymer. (30) Two MesoPore 300×7.5 mm columns (Polymer Laboratories) were used in series with stabilized tetrahydrofuran as the mobile phase at a flow rate of 1 mL $min^{-1}$ at 35° C.

2.8 In Vitro Apatite Forming Bioactivity Assay

The procedure for the apatite-forming test conducted by cutting BG disks in half to create a hemi-circular shape, and submerging each sample in 10 mL SBF in a plastic tube and maintaining them in an incubator at 37° C. (31). The SBF fluid was completely replenished for each sample every 3 days, while the altered SBF was retained for further analysis. At designated time points, samples were removed from the SBF and gently rinsed with ion-exchanged and distilled water and dried in a desiccator.

2.9 Scanning Electron Microscopy (SEM)

Samples were sputter-coated with gold to provide electrical conductivity and mounted with conductive carbon tape. Images were obtained using a Hitachi S-4200 SEM (Finchampstead, UK) and processed using the Quartz PCI system software.

2.10 X-Ray Diffraction (XRD)

XRD scans were performed on a Scintag $X_1$ θ/θ automated powder X-ray diffractometer in the range of 15-50 in 2 theta using a Cu Kα radiation source and a zero-background Si(510) sample support (31). Scans were taken in step mode with a step size of 0.05 and a preset time of 30 s.

2.11 Nuclear Magnetic Resonance (NMR)

The SBF solutions recovered from the in vitro apatite-forming assay were lyophilized and the residues were reconstituted in deuterated DMSO. Nuclear magnetic resonance spectroscopy (NMR) was performed with a Bruker 300 MHz NMR (Billerica, Mass.) to determine the structure of the residues.

2.12 Synthesis of BG/PUR Composites

The components of the composite were mixed by hand in a two-step method. The PCL300 and the appropriate amount of catalyst (5 wt % FeAA or 33 wt % TEDA in DPG) were weighed in one side of a small plastic cup and mixed until homogenous. The LTI-PEG prepolymer was added to the clean half of the cup (avoiding contact with the PCL300/catalyst mixture) and the appropriate amount of BG spread over the entire surface of the cup. The relative amounts of LTI-PEG prepolymer and PCL300 were calculated assuming an isocyanate index of 140 (i.e., 40% excess isocyanate) (32, 33). The amount of BG was based on a density of 2.7 g $cm^{-3}$ and a targeted volume percent (56.7%) in the final composite. All components were mixed vigorously, loaded into a 5 mL syringe, and injected into a mold. The mixture was cured under a load of 0.96 kg for 5 min to simulate compacting the material in a confined defect space, followed by curing at unloaded conditions at 37° C. for 24 h to simulate curing in the human body.

2.13 Surface Tension and Contact Angle Measurements

The surface tension (γ) of the PUR mixture (LTI-PEG prepolymer and PCL300 polyol, without catalyst) of the BG/PUR composite was measured with a Sigma 70x model 1000 IUP tensiometer, by KSV Instruments LTD (Linthicum Heights, Md.). Measurements used a platinum plate, a small vessel, and the Wilhelmy method to estimate the surface tension as an average of five independent measurements.

Wetting experiments were conducted using the sessile drop method. Equilibrium contact angles were measured with a Rame-Hart goniometer on static ~10 µL drops of water or the PUR mixture. A syringe was used to apply the liquid to the BG disk surface specimens. With the PUR mixture, the freestanding drop was allowed to reach static equilibrium on the surface for 2 min before measurements were taken. Reported errors represent the averages and standard deviations, respectively, from three independent measurements.

2.14 Characterization of BG/PUR Composites

The porosity of the composites was computed from SEM cross-sectional images at 60× magnification. The pore area in each image was calculated using MetaMorph Offline (Version 7.7.0.0) software. The porosity was calculated as the pore area fraction.

2.15 Mechanical Testing of BG/PUR Composites

Cylindrical samples of each treatment group were prepared for mechanical testing. Compression testing was performed using an MTS 858 Bionix Servohydraulic Test System. Cylindrical specimens (6×12 mm) were conditioned in PBS at room temperature for 24 h immediately before testing. The specimens were pre-loaded to approximately 12 N followed by continuous compression until failure at a rate of 25 mm $min^{-1}$. The load and position were recorded every 0.01 s. The compressive stress was calculated by dividing the load by the cross sectional area of the samples post-hydration. Compressive modulus was calculated as the slope of the initial linear section of the stress-strain curve, compressive strength as the maximum stress achieved, and compressive ultimate yield strain (UYS) as the strain at the compressive strength. Torsion testing was performed using an Instron Dynamite 8841 fatigue tester equipped with a 1.7 Nm torque cell. Approximately 4 mm of each end of the cylindrical specimens (6×20 mm) was potted in larger cylindrical molds made from Technovit 4000. The potting material was prepared by mixing the powder:syrup I:syrup II at a ratio of 2:2:1 following the manufacturer's instructions. The gage length (i.e., the gap between the potted ends) was approximately 12 mm. Specimens were conditioned in PBS at room temperature for 24 h and secured to the Instron with one end attached to a stationary torque transducer that measured the torque (T). The crosshead speed was 0.035 rad s$^{-1}$ in order to minimize viscoelastic effects (34, 35). The shear stress ($\tau$) was determined from the torque/angle unit length ($\theta=\alpha/L$) curve using the equation:

$$\tau = \frac{1}{2\pi r^5}\left[\theta\frac{dT}{d\theta} + 3T\right]$$

where r is the radius of the cylindrical specimen, dT/d$\theta$ was determined by fitting a 5$^{th}$ order polynomial to the experimental torque curve (from zero up to the maximum T and corresponding $\theta$ values), and T is the interpolated torque (34). The shear modulus (G) was defined as the slope of the linear portion of the stress/angular deformation curve (G=$\tau$/$\gamma$), the torsion strength as the maximum shear stress achieved, and the torsion UYS as the strain at the torsion strength. For both compression and torsion testing, the energy-to-failure was defined as the area under the curve from zero to the maximum stress reached.

Results 3.1 Surface Modifications

The properties of the PCL ($M_n$, PDI, and wt % grafted) grafted to BG particles and disks are shown in Table 5. The surface composition measured by XPS and the water contact angles of the BG discs are listed in Tables 6 and 7, respectively. Prior to surface treatment, oxygen (62.0%), silicon (17.6%), carbon (10.1%), sodium (7.3%) and calcium (2.9%) were present. When the discs were treated with the amino silane-coupling agent (Sil-BG), the surface concentration of carbon increased (37.6%) and nitrogen was detected (5.0%), confirming that surface was covered with amino silane (FIG. 28A). When Sil-BG was subjected to PCL polymerization, Sn was present at 0.37% and 0.11% for low (Low PCL-BG) and high molecular weight PCL (High PCL-BG), respectively, and therefore the Sn(Oct)$_2$ catalyst may be bound to the grafted PCL. Additionally, for the PCL-grafted groups, the amount of carbon increased to 69.2% compared to BG (10.1% C) and Sil-BG (37.6% C), while calcium and nitrogen were not detected. These results suggest that PCL polymerized from the aminosilane molecule grafted to the BG surface (FIG. 27B). As shown in Table 7, the surface modifications were further confirmed by water contact angle measurements, and showed an increase in hydrophobicity of the U (unmodified, cleaned)-BG surface) (14.7° after grafting a silane layer) (45.0° (37) and surface PCL polymerization) (66.0° (38).

Figure 28:
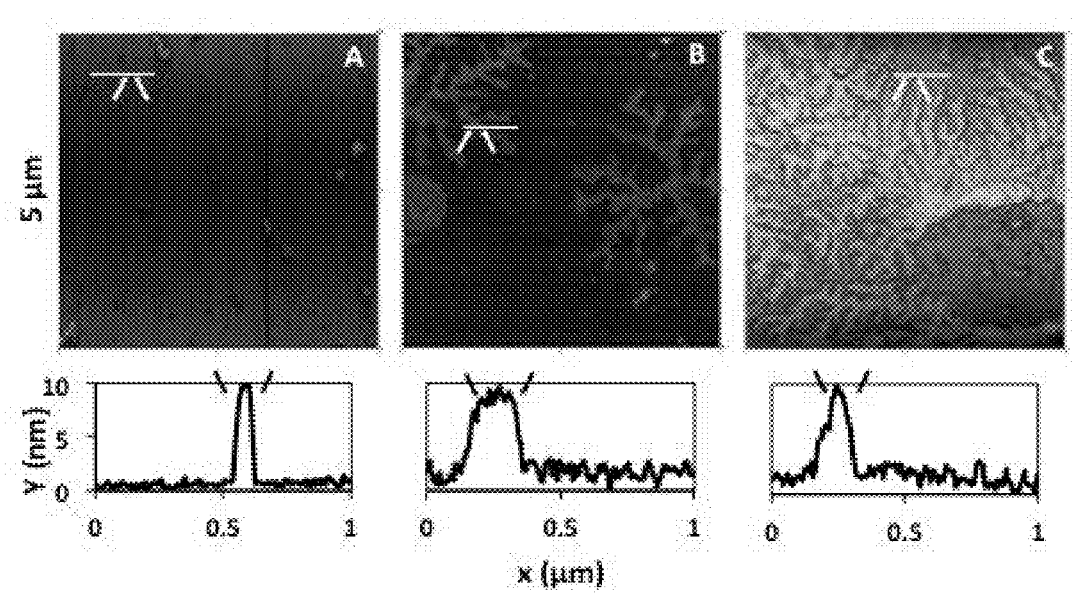
FIG. 28 shows AFM AC (tapping) mode images (5×5 µm) of a bioglass surface after surface modification, with height profile along the corresponding a 1 µm line, where surfaces are treated with (A) Silane, (B) Low PCL, and (C) High PCL.

The mean surface thicknesses on silicon oxide wafers for the silane, Low PCL, and High PCL grafted layers measured by ellipsometry were 1.9±0.3 nm, 6.9±0.4 nm, and 12.8±0.3 nm, respectively (Table 7). FIG. 28 shows representative AFM images of the same groups. Silanized surfaces featured islands approximately 10 nm in height that are conjectured to be aggregates of polymerized APTES. Low PCL modification showed partial coverage by nodular structures of the PCL brush layer that form lamellae. The difference in height between the lamellae and surrounding surface was approximately 8 nm, which is consistent with previous reports (39, 40). Similarly, High PCL modification showed increased coverage density of flat-on lamellae compared to the Low PCL group with similar height.

TABLE 5

Characterization of the surface-initiated ring opening polymerization (ROP) of ε-caprolactone.

| Group | $M_n$ (g/mol) | Polydispersity Index (PDI) | Wt % PCL |
|---|---|---|---|
| Low PCL-BG | 4,574 (7,512) | 1.2 (1.1) | 0.16 |
| High PCL-BG | 24,667 (26,654) | 1.6 (1.9) | 0.09 |

Values of $M_n$ are reported for dynamic polymerization on the BG particle surface (numbers in parentheses were measured under static polymerization conditions on the BG disk surface).

TABLE 6

Characterization of the composition surface-modified BG discs.

| Group | C 1s | O 1s | Si 2p | Ca 2p | Na 1s | N 1s | Sn 3d |
|---|---|---|---|---|---|---|---|
| U-BG | 10.1 | 62.0 | 17.7 | 2.9 | 7.3 | ND | ND |
| Sil-BG | 37.6 | 42.4 | 13.2 | 0.7 | 1.2 | 5.0 | ND |
| Low PCL-BG | 69.2 | 28.5 | 2.0 | ND | 0.1 | ND | 0.4 |
| High PCL-BG | 69.2 | 27.7 | 3.0 | ND | ND | ND | 0.1 |

ND denotes none detected.
U-BG: unmodified,
Sil-BG: silane-grafted.

TABLE 7

Properties of surface-modified BG discs.

| Group | Water contact angle, θ (deg.) | Surface layer thickness, (nm) | PUR contact angle, θ (deg.) | Work of adhesion, $W_{ad}$ (mJ m$^{-2}$) |
|---|---|---|---|---|
| U-BG | 14.7 ± 0.6 | — | 28.0 ± 0.0 | 90.0 ± 0.6 |
| Sil-BG | 45.0 ± 2.7 | 1.9 ± 0.3 | 27.3 ± 1.5 | 90.2 ± 1.8 |
| Low PCL-BG | 66.7 ± 2.5 | 6.9 ± 0.4 | 26.3 ± 1.2 | 90.6 ± 1.5 |
| High PCL-BG | 66.0 ± 3.6 | 12.8 ± 0.3 | 28.3 ± 1.2 | 89.9 ± 1.5 |

Values are reported as the mean ± standard deviation of triplicate samples.
Water contact angles from published works for silane (40-42°) (37) and PCL (73°) (38).
The work of adhesion ($W_{ad}$) was calculated from the measured surface tension of the non-reactive PUR mixture ($\gamma$ = 47.8 ± 0.29 mJ m$^{-2}$).

3.2 Work of Adhesion

Measurements of the equilibrium contact angles (θ) of the components of the PUR mixture (LTI-PEG prepolymer and PCL300 polyol, without catalyst) on the BG disk surfaces in air are listed in Table 7. The measured contact angles were used to calculate the thermodynamic work of adhesion (Wad, Table 7) from the Young-Dupré relationship (23, 41):

$$W_{ad}=\gamma(1+\cos\theta)$$

where $\gamma$ is the surface tension of the liquid PUR mixture. Because the Wad calculation is solely dependent on the equilibrium contact angle and $\gamma$ is the same for all groups, no significant differences between groups were calculated.

3.3 In Vitro Apatite Forming Assay

The kinetics of HCA formation upon immersion in SBF for unmodified BG and High PCL-BG disks were compared. Sil-BG was not evaluated (24). Similarly, Low PCL-BG modification group was not included, since it was anticipated that the High PCL-BG group would have the most effect on the kinetics of HCA formation. The presence of HCA was qualitatively identified by SEM imaging. The surfaces of U- and High PCL-BG immersed in SBF for 0

Figure 29:
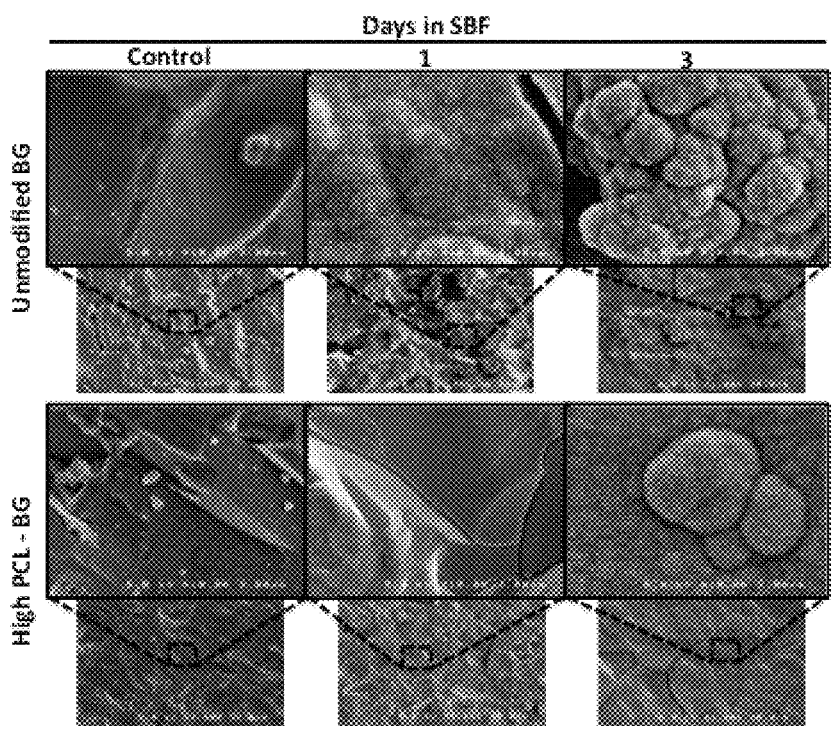
FIG. 29 shows SEM images of BG disks not submerged or submerged in SBF for 1 or 3 days are shown at low (1,000×) and high (10,000×) magnifications.

(control), 1 and 3 days are shown in FIG. 29. Low (1,000×) and high magnifications (10,000×) are shown for each group and time point (31). The control groups do not show any HCA nucleated on the surface. After 1 day in SBF, the high magnification images show the presence of nucleated apatite on the surface of U-BG, while the High PCL-BG surface does not. After 3 days in SBF, apatite appears to have nucleated on the High PCL-BG surface.

Figure 30:
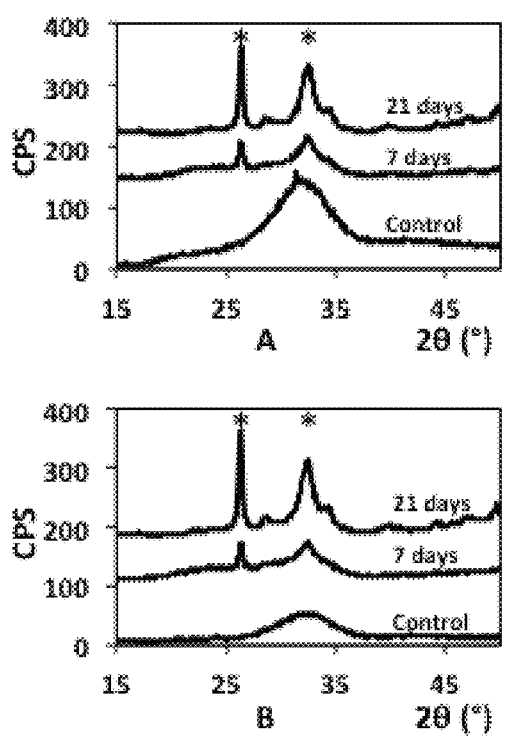
FIG. 30 shows XRD spectra of BG disks not submerged (control) or submerged in SBF for 7 or 21 days for (A) unmodified BG and (B) High PCL-BG. Peaks for HCA (26° and) 33° marked by *.

The crystallinity of the U- and High PCL-BG discs before and after immersion in SBF was evaluated by XRD. FIG. 30 shows the XRD spectra for these groups after immersion in SBF for 0 (control), 7 and 21 days. The two major peaks for HCA (diffraction angle 2θ=26° and 33°) are evident in the spectra for both U- and High PCL-BG (14, 42) but absent in the control spectra, which are amorphous. After 7 days in SBF, peaks at 2θ=26° and 33° appear for both U- and High PCL-BG, implying the formation of a polycrystalline HCA layer (14). After 21 days in SBF, these two peaks become more distinct and other peaks correlating to crystalline HCA (JCPDS pattern 9-432) began to appear (42).

3.4 Characterization of BG/PUR Composites

Figure 31:
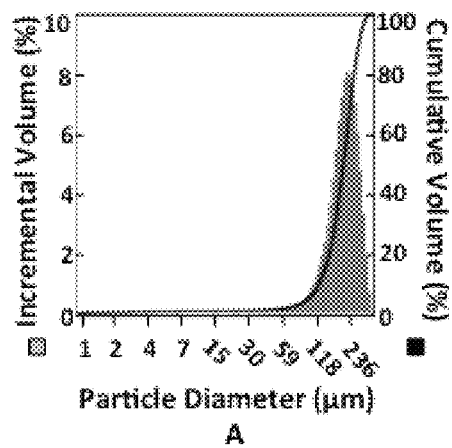
FIG. 31 shows (A) a particle size distribution of bioglass particles, and (B) a SEM image of clean bioglass particles.
Figure 31:
Figure 32:
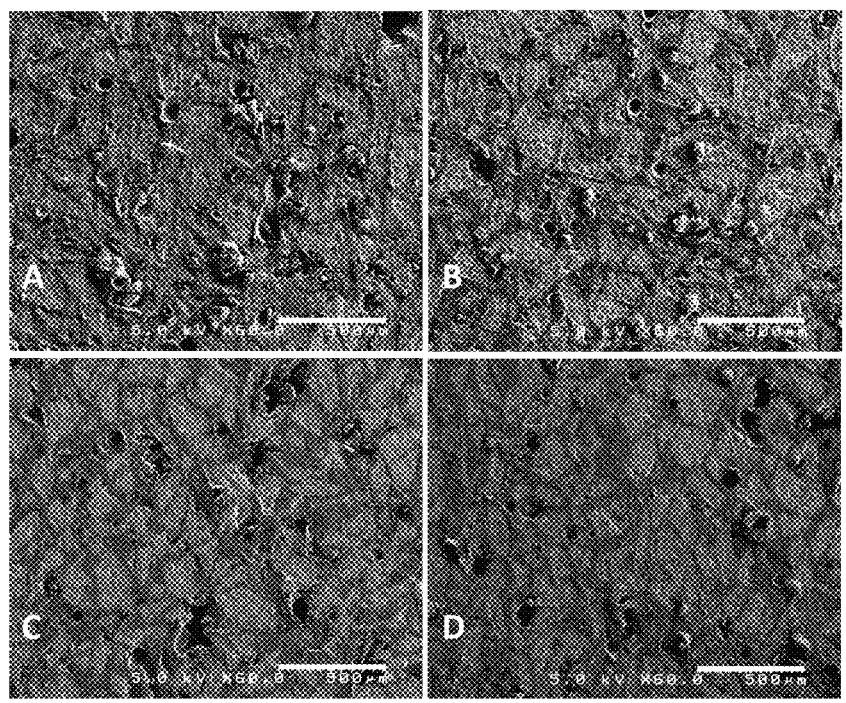
FIG. 32 shows cross-sectional SEM images of various BG/PUR composites made with: (A) TEDA, Unmodified BG, (B) TEDA, High PCL-BG, (C) FeAA, Unmodified BG, (D) FeAA, High PCL-BG.

Light scattering was used to measure the size distribution of the BG particles used within the BG/PUR composites. As shown in FIG. 31A, the mean diameter value was 211 μm. The morphology of the BG particles is shown in FIG. 31B. The shape of the particles did not change post-surface modification(s) (images not shown). Two-phase BG/PUR composites synthesized by a two-step method exhibited a range of pore morphologies and interactions between the BG and PUR phases, as evidenced by low magnification SEM imaging. BG particles can be identified in the images of the cross-sections of BG/PUR composites shown in FIG. 32A-D. TEDA BG/PUR composites (FIG. 32A-B) made with U-BG and High PCL-BG exhibited both voids approximately 50 μm in diameter as well as smaller circular pores, which are conjectured to result from the blowing reaction. In contrast, FeAA BG/PUR composites (FIG. 32C-D) made with U- and High PCL-BG BG exhibited predominantly irregularly shaped voids with fewer small circular pores.

The porosities of the BG/PUR composites are listed in Table 8. Values are reported as mean±standard deviation of triplicate samples. The porosity of each TEDA-catalyzed composite was significantly (p<0.05) less than the U-BG material, while no statistical differences were observed between FeAA-catalyzed composites. Except for the U-BG composites, differences in porosity between catalysts were not significant. The change in mass of the composites after conditioning in PBS was also measured. As listed in Table 8 U-BG had the largest change in mass (weight %) for both the TEDA (6.0%) and FeAA (2.4%) catalysts, while High PCL-BG absorbed the least amount (1.4% and 0.7%, respectively). All groups were significantly (p<0.05) lower than the TEDA-catalyzed U-BG.

TABLE 8

Porosity and water absorption of TEDA and FeAA BG/PUR composites.

| Group | TEDA Porosity (%) | TEDA Water Absorption (wt %) | FeAA Porosity (%) | FeAA Water Absorption (wt %) |
| --- | --- | --- | --- | --- |
| U-BG | 10.6 ± 2.1 | 6.0 ± 1.4 | 6.9 ± 0.3 | 2.4 ± 0.1 |
| Sil-BG | 7.2 ± 0.4 | 2.3 ± 0.4 | 6.9 ± 2.6 | 1.2 ± 0.2 |
| Low PCL-BG | 7.8 ± 0.9 | 1.7 ± 0.2 | 4.5 ± 0.6 | 1.0 ± 0.1 |
| High PCL-BG | 4.9 ± 1.0 | 1.4 ± 0.1 | 7.8 ± 1.5 | 0.7 ± 0.2 |

3.7 Mechanical Properties of BG/PUR Composites

Figure 33:
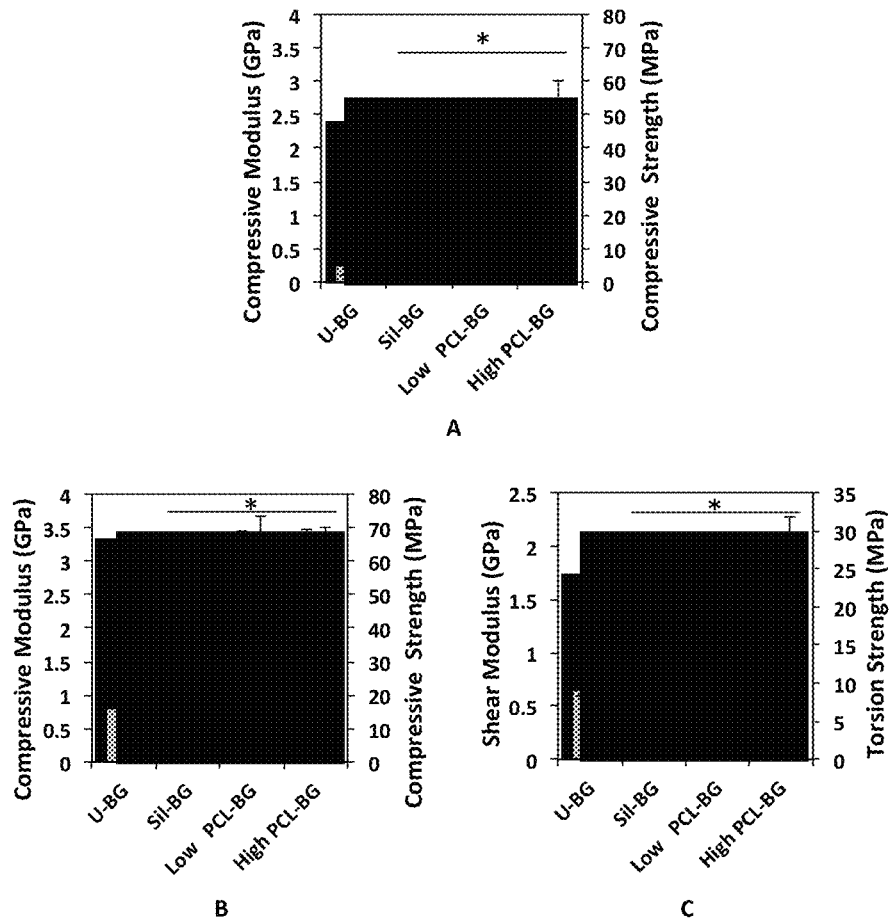
FIG. 33 shows mechanical properties of BG/PUR composites, where (A) shows compressive properties of composites synthesized using TEDA catalyst, (B) shows compressive properties of composites synthesized using FeAA catalyst, (C) shows torsional properties of composites synthesized using FeAA catalyst. * indicates $p<0.05$ compared to U-BG within respective catalyst, testing condition, and property.

The mechanical properties of the BG/PUR bioco composites mposites can be dependent on the surface properties of the BG. Additionally, these properties can depend on the catalyst composition. FIG. 33A shows the compressive modulus and strength of the TEDA and BG/PUR composite groups. U-BG exhibited a compressive modulus and strength of 0.255 GPa and 7.9 MPa, respectively. Grafting molecules to the surface increased the mechanical strength of the composites compared to U-BG. High PCL-BG exhibited a compressive modulus and strength of 2.31 GPa and 53.8 MPa. No statistical significances were observed between the composite groups made with any of the surface-modified BG particles.

The compressive mechanical properties of the FeAA BG/PUR composites followed the trends observed for the TEDA group, but with an increase in values for each respective BG group. FIG. 33B shows the compressive modulus and strength of the FeAA BG/PUR composite groups. U-BG exhibited a compressive modulus and strength of 0.808 GPa and 31.3 MPa, respectively. Similarly, grafting surface molecules to the BG particles increased the compression modulus and strength of the composites compared to U-BG. High PCL-BG exhibited a compressive modulus and strength of 3.23 GPa and 67.4 MPa. As for the composite made with TEDA, no statistical significances were observed between the composite groups made with any of the surface-modified BG particles.

Additional compressive mechanical properties were calculated for the FeAA BG/PUR composite groups. The compression ultimate yield strain (UYS) and energy-to-failure values are listed in Table 9. No significant difference between U-BG and the composites containing surface-modified BG were observed. The presence of grafted surface molecules significantly decreased the compression UYS of the corresponding composites, as U-BG exhibited an UYS of 7.1% while Sil- and High PCL-BG reached a value of 4.8% and 3.6%, respectively (p<0.05). This reduction in yield strain did not translate to a decrease in toughness, as U- and High-PCL BG composites showed an energy-to-failure of 1398 kJ m$^{-3}$ and 1323 kJ m$^{-3}$ and Sil-BG exhibited the highest energy-to-failure value, 1944 kJ m$^{-3}$.

TABLE 9

Mechanical Properties of FeAA BG/PUR composites.

| | Compression | | Torsion | |
| --- | --- | --- | --- | --- |
| Group | Energy-to-Failure (kJ m$^{-3}$) | Ultimate Yield Strain (%) | Energy-to-Failure (kJ m$^{-3}$) | Ultimate Yield Strain (%) |
| U-BG | 1,398.0 ± 111.8 | 7.1 ± 2.5 | 279.3 ± 18.9 | 5.9 ± 4.5 |
| Sil-BG | 1,766.0 ± 184.4 | 4.8 ± 0.3 | 661.0 ± 125.1 | 3.8 ± 0.4 |
| Low PCL-BG | 1,943.5 ± 265.2 | 4.9 ± 0.7 | 383.1 ± 143.2 | 2.3 ± 0.3 |
| High PCL-BG | 1,322.6 ± 143.4 | 3.6 ± 0.4 | 512.3 ± 79.6 | 3.0 ± 0.6 |

Values reported as mean ± standard deviation of triplicate samples.

The mechanical properties of the FeAA BG/PUR composites under torsion followed the trends seen under compression (FIG. 33C). U-BG showed the weakest mechanical properties, with a shear modulus and torsional strength of 0.642 GPa and 13.9 MPa, respectively. As observed under compression, surface modifications significantly (p<0.05) increased the torsional strength of the composite compared to U-BG. High PCL-BG exhibited a shear modulus and torsional strength of 1.67 GPa and 29.1 MPa. No statistical significance was determined between the groups made with surface-modified BG particles. The torsional UYS and energy-to-failure of the composites are listed in Table 9. As observed under compression, grafted surface molecules decreased the UYS of the composites under torsion. The Sil-BG group exhibited the highest energy-to-failure (661 kJ m$^{-3}$), which was more than twice that of U-BG (279 kJ m$^{-3}$).

Physical chain entanglements between surface-grafted molecules and the PUR network also can contribute to the interfacial adhesion strength. The mesh size of the PUR network was measured by swelling experiments to be 1.3 nm (55). Thus, the network mesh size is significantly smaller than the thickness of the grafted PCL (6.9 and 12.8 nm for Low and High PCL-BG, respectively), which, without being bound by theory or mechanism, may result in chain entanglements and physical crosslinks. For linear polymers, physical crosslinks due to chain entanglements result as the molecular weight of the polymer approaches the critical molecular weight for entanglements $M_e$ (56), which for PCL is 15,000 g mol$^{-1}$ (57).

Also without being bound by theory or mechanism, physical entanglements between grafted and bulk cross-linked polymer chains may increase mechanical properties for the PCL-grafted BG, the comparatively shorter grafted silane layer (2.2 nm) may reduce the relative contribution of chain entanglements to interfacial bonding for the Sil-BG group, and the higher reactivity of the amines in APTES compared to the hydroxyl groups in PCL (58) may compensate for reduced physical entanglements through a greater number of interfacial covalent bonds.

Example 17

This Example utilizes embodiments of bioglass polyurethane composites, such as those described in Example 16, to treat bone injuries in vivo. To avoid undue repetition, some of the materials and methods described in the previous Examples are not repeated in this Example.

A non-weight bearing femoral condyle plug defect model was used in rats. The defect was a unilateral cylindrical defect (3 mm diameter, 5 mm depth) that was drilled into the medial side of the femurs. Then, high-PCL bioglass polyurethane composites (e.g., see Example 16) were fabricated, implanted into the defect, and allowed to cure. After 4 and 8 weeks the rats were euthanized and the femurs were harvested.

Harvested defects were analyzed in a radial fashion through histomorphometry and x-ray microtomography to quantify the rate of bone formation from the defect/composite interface inward. Specifically, the femurs were fixed and scanned with μCT and 3D analysis was conducted with tubes separated by a change in radius of 0.5 mm and a region of interest depth, which essentially equated to the entire defect. Similarly, after embedding in poly(methyl-methacrylate), longitudinal cross sections of the defects, at the midway point, were made and histologically evaluated with Sanderson's Rapid bone stain and Von Gieson solution comprising 100 mL of saturated aqueous solution of picric acid and 5 mL of 1% aqueous solution of acid fuchsin. Histology showed that at 4 weeks there was substantial cellular infiltration. At 8 weeks bone growth was seen throughout the defect, including the center of the defect, and appositional bone growth was seen along the polyurethane and bioglass components.

Figure 34:
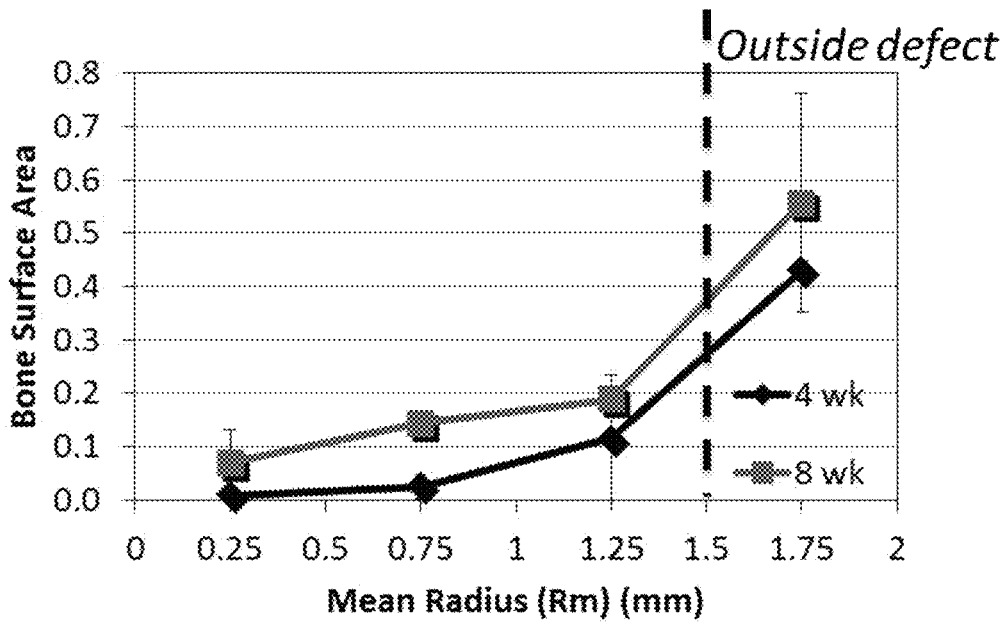
FIG. 34 shows the bone surface area versus the mean radius of a PLC-modified bioglass/PUR composite graft (3 mm diameter) calculated using histomorphometry.
Figure 35:
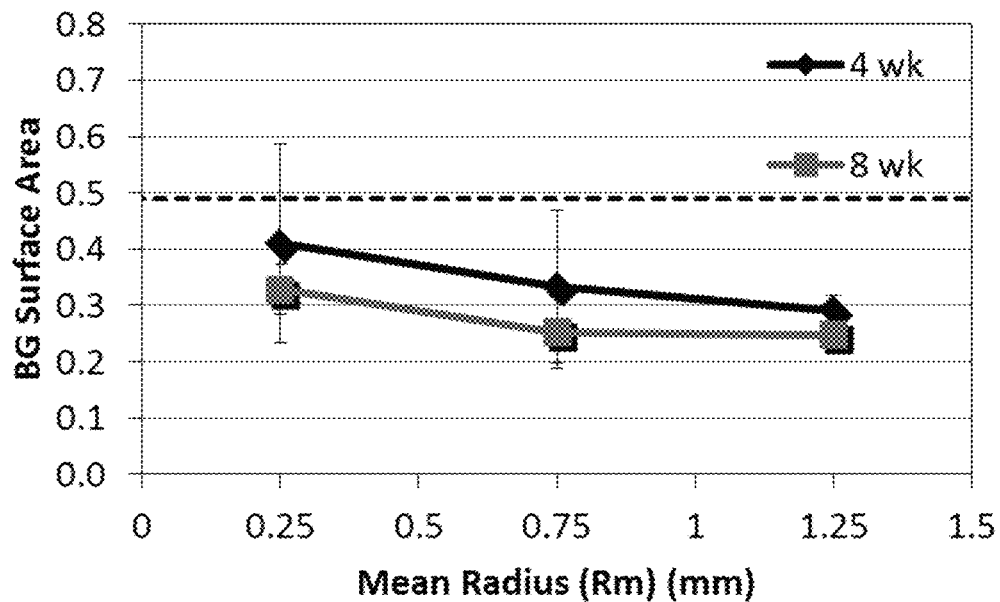
FIG. 35 shows the bioglass surface area versus the mean radius of a PLC-modified bioglass/PUR composite graft (3 mm diameter) calculated using histomorphometry.
Figure 36:
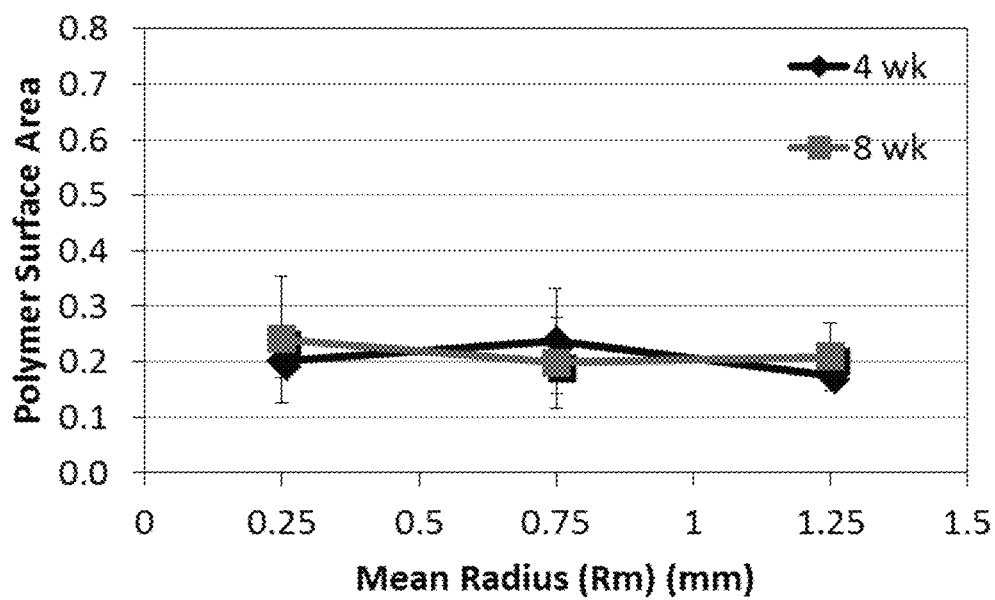
FIG. 36 shows the polymer surface area versus the mean radius of a PLC-modified bioglass/PUR composite graft (3 mm diameter) calculated using histomorphometry.
Figure 37:
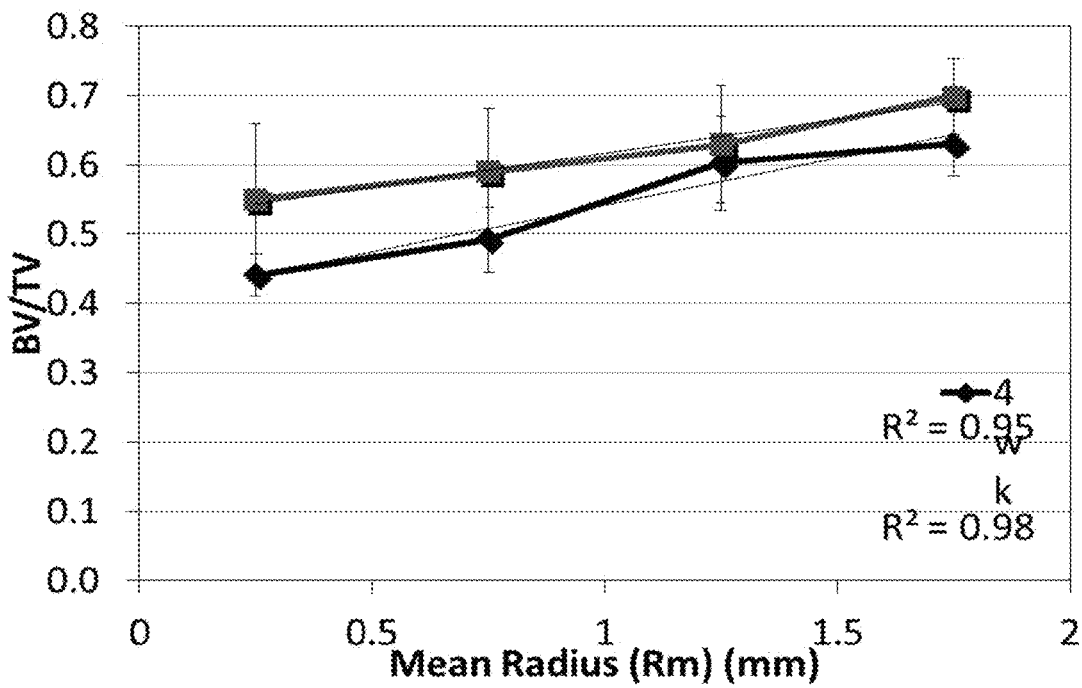
FIG. 37 shows the fractional bone volume (BV/TV) versus the mean radius of a PLC-modified bioglass/PUR composite graft (3 mm diameter) calculated using microCT.

Histomorphometry was used to quantify the 2D surface area of bone, bioglass, polymer in the defect at the two time points. As shown in FIG. 34, bone surface area increased as mean radius increased, showing that cells infiltrated from the outer surface of the composite. FIG. 35 shows that the surface area of bioglass decreased in an approximately linear fashion as the radius increased, and continued to decrease over time. The relatively slow decrease in bioglass surface area can be advantageous for weight bearing applications. Lastly, FIG. 36 shows that polyurethane surface area experienced minimal degradation between weeks 4 and 8. While degradation rates can be tuned in some embodiments, relatively slow degradation can be helpful for preventing resorption gaps between composites and healing bone tissue. Note that in these figures a mean radius (Rm) of 0 equates to the cortex of the composite, whereas the edge of the defect/composite interface equates to a Rm of 1.5 mm.

μCT was then used to calculate the bone volume fraction (BV/TV) of total mineral content relative to the Rm of the composites. As shown in FIG. 37, bone volume fraction increased as mean radius increased, indicating that as cell infiltrated the composite they formed new bone within the composite. Specifically, the BV/TV, at mean radial distances of 0.75 mm and 1.25 mm, increased from 0.04±0.02 to 0.09±0.02 and from 0.13±0.01 to 0.18±0.03, respectively, from week 4 to week 8. Furthermore, the results at week 8 show a relatively larger amount of new bone formation relative to the results at week 4. This relatively steady increase in bone volume fraction over time can be advantageous for composites that are weight-bearing, at least initially.

Thus, the embodied bioglass/PUR composite having low porosity allowed for cellular infiltration via creeping substitution in vivo. The balanced remodeling did not create resorption gaps, and can be advantageous for applications in which the composite is weight-bearing, at least initially.

Example 18

This Example discusses the relationship between polymer degradation rate and new bone formation rate in composites. This particular Example utilizes allograft PUR composites comprising BMP-2. To avoid undue repetition, some of the materials and methods described in the previous Examples are not repeated in this Example.

PUR/allograft composites comprising low-BMP (105 μg/ml rhBMP-2) and high-BMP (420 μg/ml rhBMP-2) were prepared as previously described. The ratio of the rate of new bone formation to that of polymer degradation was calculated from the histomorphometry data. The increase in new bone formation (NB) with time was approximately linear. The data were fit to a second-order polynomial (NB=at$^2$+bt, R$^2$>0.99 for all groups), and the rate of new bone formation calculated as $r_{NB}$=d(NB)/dt. The data were fit to an exponential function (PD=aexp(bt), R$^2$>0.99 for all groups), and the rate of polymer degradation calculated as $r_{PD}$=d(PD)/dt. In contrast to blank composite and low-BMP composites, the rate of polymer degradation for the high-BMP composites was approximately linear, and thus the data were fit to a second-order polynomial similar to new bone formation.

Figure 38:
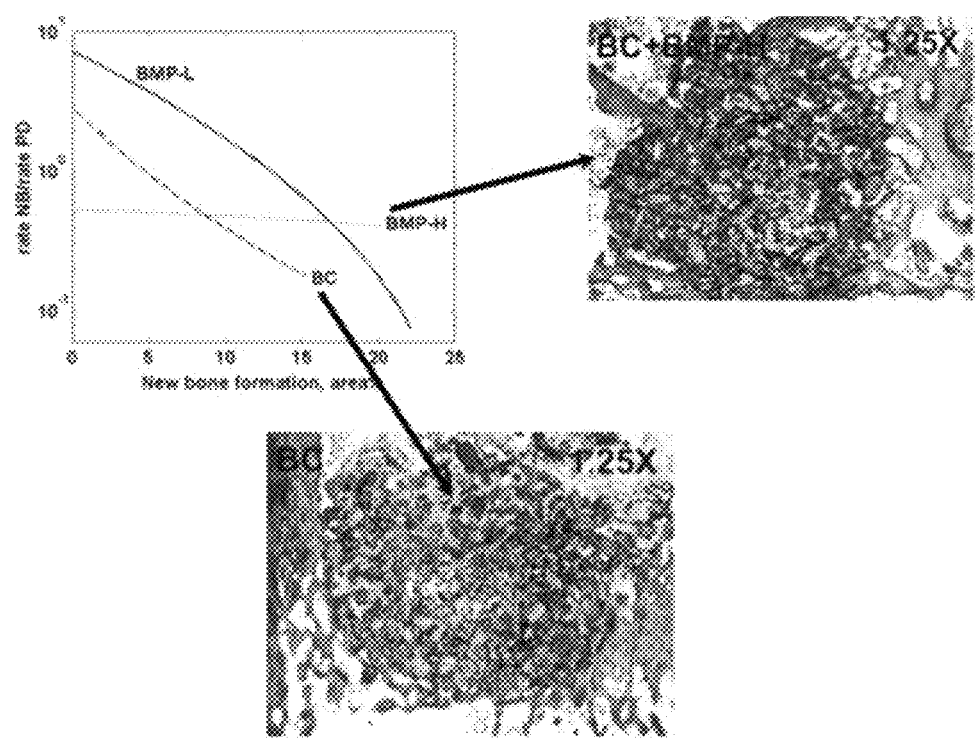
FIG. 38 shows a plot of $r_{NB}/r_{PD}$ vs new bone formation (area %) for the allograft composite alone (BC), the allograft composite augmented with 105 micrograms/ml rhBMP-2 (BMP-L), and the allograft composite augmented with 420 micrograms/ml rhBMP-2 (BMP-H). Histological sections of the BC at 12 weeks ($r_{NB}/r_{PD}$ <0.2) show resorption gaps, while BC+BMP-H shows more balanced remodeling at 12 weeks.

The rate of new bone formation relative to that of polymer degradation ($r_{NB}/r_{PD}$) is plotted versus new bone formation in FIG. 38 to assess the effects of augmentation with rhBMP-2 on the relative rates as healing progresses. For both BC and BMP-L groups, initially $r_{NB}/r_{PD}$>1, indicating that new bone formation outpaced polymer degradation at the early stages of healing. However, without being bound by theory or mechanism, autocatalytic bulk degradation of the polymer at later stages caused polymer degradation to outpace new bone formation ($r_{NB}/r_{PD} \ll 1$), although low dose of rhBMP-2 appears to delay the point at which the $r_{NB}/r_{PD}$ drops below unity (5% NB for BC compared to 14% for BMP-L). In contrast, $r_{NB}/r_{PD}$ remained relatively constant at ~0.5 for the BMP-H group during the duration of healing. Without being bound by theory or mechanism, this was due to cell-mediated degradation of the polymer at the high rhBMP-2 dose. The histological sections at 12 weeks (FIG. 38) suggest that the balanced rates of new bone formation and polymer degradation promote more balanced remodeling, characterized by increased bridging of osteoconductive particles (e.g., allograft) with new bone as well as reduced areas of resorption in the inner core of the material.

The invention thus being described, it will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification, including the Example, be considered as exemplary only, and not intended to limit the scope and spirit of the invention.

While the following terms are believed to be well understood by one of ordinary skill in the art, definitions are set forth herein to facilitate explanation of the presently-disclosed subject matter. Unless defined otherwise, all technical and scientific terms used herein have the same meaning as commonly understood by one of ordinary skill in the art to which the presently-disclosed subject matter belongs. Although many methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a composite" includes a plurality of such composites, and so forth.

Unless otherwise indicated, all numbers expressing quantities of ingredients, properties such as reaction conditions, and so forth used herein are to be understood as being modified in all instances by the term "about." Accordingly, unless indicated to the contrary, the numerical parameters set forth in the herein are approximations that may vary depending upon the desired properties sought to be determined by the present invention.

As used herein, the term "about," when referring to a value or to an amount of mass, weight, time, volume, concentration or percentage is meant to encompass variations in some embodiments of ±20%, in some embodiments of ±10%, in some embodiments of ±5%, in some embodiments of ±1%, in some embodiments of ±0.5%, and in some embodiments of ±0.1% from the specified amount, as such variations are appropriate to perform the disclosed method. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

REFERENCES

Throughout this application, various publications are referenced. All such references, specifically including those in the lists below, are incorporated herein by reference.

1. Haidar, Z. S., R. C. Hamdy, and M. Tabrizian, *Delivery of recombinant bone morphogenetic proteins for bone regeneration and repair. Part A: Current challenges in BMP delivery*. Biotechnol Lett, 2009. 31(12): p. 1817-24.
2. Gautschi, O. P., S. P. Frey, and R. Zellweger, Bone morphogenetic proteins in clinical applications. ANZ J Surg, 2007. 77(8): p. 626-31.
3. McKay, W. F., S. M. Peckham, and J. M. Badura, *A comprehensive clinical review of recombinant human bone morphogenetic protein-2 (INFUSE Bone Graft)*. Int Orthop, 2007. 31(6): p. 729-34.
4. Han, D., et al., *Optimal delivery systems for bone morphogenetic proteins in orthopedic applications should model initial tissue repair structures by using a heparin-incorporated fibrin-fibronectin matrix*. Med Hypotheses, 2008. 71(3): p. 374-8.
5. Smith, D. M., et al., *Bone morphogenetic protein 2 therapy for craniofacial surgery*. J Craniofac Surg, 2008. 19(5): p. 1244-59.
6. Miyazaki, M., et al., *A porcine collagen-derived matrix as a carrier for recombinant human bone morphogenetic protein-2 enhances spinal fusion in rats*. Spine J, 2009. 9(1): p. 22-30.
7. Garrison, K. R., et al., *Clinical effectiveness and cost-effectiveness of bone morphogenetic proteins in the non-healing of fractures and spinal fusion: a systematic review*. Health Technol Assess, 2007. 11(30): p. 1-150, iii-iv.
8. Dumas, J. E., et al., *Synthesis, characterization, and remodeling of weight-bearing allograft bone/polyurethane composites in the rabbit*. Acta Biomater. 6(7): p. 2394-406.
9. Dumas, J. E., et al., *Synthesis and characterization of an injectable allograft bone/polymer composite bone void filler with tunable mechanical properties*. Tissue Eng Part A. 16(8): p. 2505-18.
10. Bonzani, I. C., et al., *Synthesis of two-component injectable polyurethanes for bone tissue engineering*. Biomaterials, 2007. 28(3): p. 423-433.
11. Shah, M. M., M. D. Smyth, and A. S. Woo, *Adverse facial edema associated with off-label use of recombinant human bone morphogenetic protein-2 in cranial reconstruction for craniosynostosis. Case report*. J Neurosurg Pediatr, 2008. 1(3): p. 255-7.
1. Ueeck B A. Penetrating injuries to the face: delayed versus primary treatment—considerations for delayed treatment. J oral Maxillofac Surg. 2007 June; 65(6):1209-14.
2. Shermak M A, Wong L, Inoue N, Nicol T. Reconstruction of complex cranial wounds with demineralized bone matrix and bilayer artificial skin. J Craniofac Surg. 2000 May; 11(3):224-31.
3. Lemperle S M, Calhoun C J, Curran R W, Holmes R E. Bony healing of large cranial and mandibular defects protected from soft-tissue interposition: A comparative study of spontaneous bone regeneration, osteoconduction, and cancellous autografting in dogs. Plast Reconstr Surg. 1998 March; 101(3):660-72.
4. Khan Y, Yaszemski M J, Mikos A G, Laurencin C T. Tissue engineering of bone: material and matrix considerations. J Bone Joint Surg Am. 2008 February; 90 Suppl 1:36-42.

5. Chim H, Gosain A K. Biomaterials in craniofacial surgery experimental studies and clinical application J Craniofac Surg. 2009; 20:29-33.
6. Tessier P. Autogenous bone grafts taken from the calvarium for facial and cranial applications. Clin Plast Surg. 1982 October; 9(4):531-8.
7. Wan D C, Aalami O O, Wang Z, Nacamuli R P, Lorget F, Derynck R, et al. Differential gene expression between juvenile and adult dura mater: a window into what genes play a role in the regeneration of membranous bone. Plast Reconstr Surg. 2006 Sep. 15; 118(4):851-61.
8. Smith D M, Cooper G M, Mooney M P, Marra K G, Losee J E. Bone morphogenetic protein 2 therapy for craniofacial surgery. J Craniofac Surg. 2008 September; 19(5):1244-59.
9. Lew T A, Walker J A, Wenke J C, Blackbourne L H, Hale R G. Characterization of craniomaxillofacial battle injuries sustained by United States service members in the current conflicts of Iraq and Afghanistan. J oral Maxillofac Surg. 2009 January; 68(1):3-7.
10. Kauvar D S, Wolf S E, Wade C E, Cancio L C, Renz E M, Holcomb J B. Burns sustained in combat explosions in Operations Iraqi and Enduring Freedom (OIF/OEF explosion burns). Burns. 2006 November; 32(7):853-7.
11. Schmitz J P, Hollinger J O, Milam S B. Reconstruction of bone using calcium phosphate bone cements: A critical review. J Oral Maxillofac Surg. 1999; 57:1122-6.
12. Elshahat A, Shermak M A, Inoue N, Chao E Y, Manson P. The use of Novabone and Norian in cranioplasty: a comparative study. J Craniofac Surg. 2004 May; 15(3): 483-9.
13. Moghadam H G, Sandor G K, Holmes H H, Clokie C M. Histomorphometric evaluation of bone regeneration using allogeneic and alloplastic bone substitutes. J oral Maxillofac Surg. 2004 February; 62(2):202-13.
14. Clokie C M, Moghadam H, Jackson M T, Sandor G K. Closure of critical sized defects with allogenic and alloplastic bone substitutes. J Craniofac Surg. 2002 January; 13(1):111-21; discussion 22-3.
15. Goldberg C S, Antonyshyn O, Midha R, Fialkov J A. Measuring Pulsatile Forces on the Human Cranium. J Craniofacial Surgery. 2005; 16(1):134-9.
16. Bohner M. Designing ceramics for injectable bone graft substitutes. In: Vernon B L, editor. Injectable Biomaterials: Science and Applications. Philadelphia: Woodhead Publishing; 2011.
17. Spector J, Luchs J, Mehera B, Greenwald J, Smith L, Longaker M. Expression of bone morphogenetic proteins during membranous bone healing. Plastic Reconstr Surg. 2001; 107:124-34.
18. Boerckel J D, Kolambkar Y M, Dupont K M, Uhrig B A, Phelps E A, Stevens H Y, et al. Effects of protein dose and delivery system on BMP-mediated bone regeneration. Biomaterials. 2011 August; 32(22):5241-51.
19. Brown K V, Li B, Guda T, Perrien D S, Guelcher S A, Wenke J C. Improving Bone Formation in a Rat Femur Segmental Defect by Controlling Bone Morphogenetic Protein-2 Release. Tissue Eng Part A. 2011 Apr. 3.
20. Smith D M, Afifi A M, Cooper G M, Mooney M P, Marra K G, Losee J E. BMP-2-based repair of large-scale calvarial defects in an experimental model: regenerative surgery in cranioplasty. J Craniofac Surg. 2008 September; 19(5):1315-22.
21. Haidar Z S, Hamdy R C, Tabrizian M. Delivery of recombinant bone morphogenetic proteins for bone regeneration and repair. Part A: Current challenges in BMP delivery. Biotechnol Lett. 2009 December; 31(12):1817-24.
22. McKay W F, Peckham S M, Badura J M. A comprehensive clinical review of recombinant human bone morphogenetic protein-2 (INFUSE Bone Graft). Int Orthop. 2007 December; 31(6):729-34.
23. Carter T G, Brar P S, Tolas A, Beirne O R. Off-Label Use of Recombinant Human Bone Morphogenetic Protein-2 (rhBMP-2) for Reconstruction of Mandibular Bone Defects in Humans. J oral Maxillofac Surg. 2008; 66:1417-25.
24. Herford A S, Boyne P J. Reconstruction of Mandibular Continuity Defects With Bone Morphogenetic Protein-2 (rhBMP-2). J oral Maxillofac Surg. 2008; 66:616-24.
25. Panetta N J, Gupta D M, Longaker M T. Bone tissue engineering scaffolds of today and tomorrow. J Craniofac Surg. 2009 September; 20(5):1531-2.
26. Hollister S J, Lin C Y, Saito E, Schek R D, Taboas J M, Williams J M, et al. Engineering craniofacial scaffolds. Orthod Craniofac Res. 2005 August; 8(3):162-73.
27. Dumas J E, Zienkiewicz K, Tanner S A, Prieto E M, Bhattacharyya S, Guelcher S. Synthesis and Characterization of an Injectable Allograft Bone/polymer Composite Bone Void Filler with Tunable Mechanical Properties. Tissue Eng Part A. 2010 Mar. 10; 16(8):2505-18.
28. Dumas J E, Davis T E, Yoshii T, Nyman J, Holt G E, Perrien D S, et al. Synthesis of Allograft Bone/Polymer Composites and Evaluation of Remodeling in a Rabbit Femoral Condyle Model. Acta Biomaterialia. 2010; 6:2394-406.
29. Li J Q, Salovey R. Model Filled Polymers: The Effect of Particle Size on the Rheology of Filled Poly(methyl methacrylate) Composites. Polym Eng Sci. 2004; 44:452-62.
30. Baroud G, Cayer E, Bohner M. Rheological characterization of concentrated aqueous beta-tricalcium phosphate suspensions: the effect of liquid-to-powder ratio, milling time, and additives. Acta Biomater. 2005 May; 1(3):357-63.
31. An Y H, Friedman R J. Animal models of bone defect repair. In: An Y H, Friedman R J, editors. Animals Models in Orthopaedic Research. Boca Raton: CRC Press; 1999.
32. Otsu N. A threshold selection method for gray level histogram. IEEE Trans Syst Man Cybern. 1978; SMC-9 (1)(62-66).
33. Bohner M. Calcium orthophosphates in medicine: from ceramics to calcium phosphate cements. Injury. 2000; 31(Supplement 4):S-D37-47.
34. Lewis G. Percutaneous Vertebroplasty and Kyphoplasty for the Stand-Alone Augmentation of Osteoporosis-Induced Vertebral Compression Fractures: Present Status and Future Directions. J Biomed Mater Res Part B: Appl Biomater. 2007; 81B:371-86.
35. Clarkin O M, Boyd D, Madigan S, Towler M R. Comparison of an experimental bone cement with a commercial control, Hydroset™. J Mater Sci: Mater Med. 2009; 20:1563-70.
36. Bohner M, Baroud G. Injectability of calcium phosphate pastes. Biomaterials. 2005; 26(13):1553-63.
37. Chemg A, Takagi S, Chow L C. Effects of hydroxypropyl methylcellulose and other gelling agents on the handling properties of calcium phosphate cement. J Biomed Mater Res. June 5; 35(3):273-7.
38. Gilardino M S, Cabiling D S, Bartlett S P. Long-term follow-up experience with carbonated calcium phosphate cement (Norian) for cranioplasty in children and adults. Plastic and reconstructive surgery. 2009 March; 123(3): 983-94.
39. Torquato S, Truskett T M, Debenedetti P G. Is Random Close Packing of Spheres Well Defined? Phys Rev Let. 2000; 84(10):2064-7.
40. Adhikari R, Gunatillake P A, Griffiths I, Tatai L, Wickramaratna M, Houshyar S, et al. Biodegradable injectable polyurethanes: synthesis and evaluation for orthopaedic applications. Biomaterials. 2008 October; 29(28):3762-70.
41. Malinin T I, Carpenter E M, Temple H T. Particulate bone allograft incorporation in regeneration of osseous defects; importance of particle sizes. Open Orthop J. 2007; 1:19-24.
42. Hasegawa S, Ishii S, Tamura J, Furukawa T, Neo M, Matsusue M, et al. A 5-7 year in vivo study of high-strength hydroxyapatite/poly(L-lactide) composite rods for the internal fixation of bone fractures. Biomaterials. 2006; 27:1327-32.
43. Hafeman A E, Zienkiewicz K J, Zachman A L, Sung H J, Nanney L B, Davidson J M, et al. Characterization of the degradation mechanisms of lysine-derived aliphatic poly(ester urethane) scaffolds. Biomaterials. 2011 Sep. 21; 32(2):419-29.
44. Li B, Yoshii T, Hafeman A E, Nyman J S, Wenke J C, Guelcher S A. The effects of rhBMP-2 released from biodegradable polyurethane/microsphere composite scaffolds on new bone formation in rat femora. Biomaterials. 2009 December; 30(35):6768-79.
45. Donath K, Laass M, Gunzl H J. The histopathology of different foreign-body reactions in oral soft tissue and bone tissue. Virchows Arch A Pathol Anat Histopathol. 1992; 420(2):131-7.
46. Takaoka K, Koezuka M, Nakahara H. Telopeptide-depleted bovine skin collagen as a carrier for bone morphogenetic protein. J Orthop Res. 1991 November; 9(6): 902-7.
47. Haidar Z S, Hamdy R C, Tabrizian M. Delivery of recombinant bone morphogenetic proteins for bone regeneration and repair. Part B: Delivery systems for BMPs in orthopaedic and craniofacial tissue engineering. Biotechnol Lett. 2009 December; 31(12):1825-35.
48. Miyazaki M, Morishita Y, He W, Hu M, Sintuu C, Hymanson H J, et al. A porcine collagen-derived matrix as a carrier for recombinant human bone morphogenetic protein-2 enhances spinal fusion in rats. Spine J. 2009 January-February; 9(1):22-30.
49. Sheehan J P, Sheehan J M, Seeherman H, Quigg M, Helm G A. The safety and utility of recombinant human bone morphogenetic protein-2 for cranial procedures in a nonhuman primate model. J. Neurosurg. 2003 January; 98(1):125-30.
50. Kolambkar Y M, Dupont K M, Boerckel J D, Huebsch N, Mooney D J, Hutmacher D W, et al. An alginate-based hybrid system for growth factor delivery in the functional repair of large bone defects. Biomaterials. 2011 January; 32(1):65-74.
51. Geiger M, Li R H, Friess W. Collagen sponges for bone regeneration with rhBMP-2. Adv Drug Deliv Rev. 2003 Nov. 28; 55(12):1613-29.
52. Santos M I, Unger R E, Sousa R A, Reis R L, Kirkpatrick C J. Crosstalk between osteoblasts and endothelial cells co-cultured on a polycaprolactone-starch scaffold and the in vitro development of vascularization. Biomaterials. 2009 September; 30(26):4407-15.
53. Unger R E, Sartoris A, Peters K, Motta A, Migliaresi C, Kunkel M, et al. Tissue-like self-assembly in cocultures of endothelial cells and osteoblasts and the formation of microcapillary-like structures on three-dimensional porous biomaterials. Biomaterials. 2007 September; 28(27):3965-76.
54. Szpalski M, Gunzburg R. Recombinant human bone morphogenetic protein-2: a novel osteoinductive alternative to autogenous bone graft? Acta Orthop Belg. 2005 April; 71(2):133-48.
55. Jensen E D, Pham L, Billington C J, Jr., Espe K, Carlson A E, Westendorf J J, et al. Bone morphogenic protein 2 directly enhances differentiation of murine osteoclast precursors. J Cell Biochem. 2010 Mar. 1; 109(4):672-82.
56. Okamoto M, Murai J, Yoshikawa H, Tsumaki N. Bone morphogenetic proteins in bone stimulate osteoclasts and osteoblasts during bone development. J Bone Miner Res. 2006 July; 21(7):1022-33.
57. Belfrage O, Flivik G, Sundberg M, Kesteris U, Tagil M. Local treatment of cancellous bone grafts with BMP-7 and zoledronate increases both the bone formation rate and bone density. Acta Orthop. 2011 April; 82(2):228-33.
58. Schwartz Z, Somers A, Mellonig J T, Carnes D L, Jr., Wozney J M, Dean D D, et al. Addition of human recombinant bone morphogenetic protein-2 to inactive commercial human demineralized freeze-dried bone allograft makes an effective composite bone inductive implant material. J. Periodontol. 1998 December; 69(12): 1337-45.
59. McGee M A, Findlay D M, Howie D W, Carbone A, Ward P, Stamenkov R, et al. The use of OP-1 in femoral impaction grafting in a sheep model. J Orthop Res. 2004 September; 22(5):1008-15.
1. Anderson D D, Van Hofwegen C, Marsh J L, Brown T D. Is elevated contact stress predictive of post-traumatic osteoarthritis for imprecisely reduced tibial plafond fractures? J Orthop Res. 2011 January; 29(1):33-9.
2. Russell T A, Leighton R K. Comparison of autogenous bone graft and endothermic calcium phosphate cement for defect augmentation in tibial plateau fractures. A multicenter, prospective, randomized study. J Bone Joint Surg Am. 2008 October; 90(10):2057-61.
3. Simpson D, Keating J F. Outcome of tibial plateau fractures managed with calcium phosphate cement. Injury. 2004 September; 35(9):913-8.
4. Hall J A, Beuerlein M J, McKee M D. Open reduction and internal fixation compared with circular fixator application for bicondylar tibial plateau fractures. Surgical technique. J Bone Joint Surg Am. 2009 Mar. 1; 91 Suppl 2 Pt 1:74-88.
5. Schwartz Z, Goldstein M, Raviv E, Hirsch A, Ranly D M, Boyan B D. Clinical evaluation of demineralized bone allograft in a hyaluronic acid carrier for sinus lift augmentation in humans: a computed tomography and histomorphometric study. Clin Oral Implants Res. 2007 April; 18(2):204-11.
6. Bohner M. Designing ceramics for injectable bone graft substitutes. In: Vernon B L, editor. Injectable Biomaterials: Science and Applications. Philadelphia: Woodhead Publishing; 2011.
7. Friedman C D, Constantino P D, Takagi S, Chow L C. BoneSource™ hydroxyapatite cement: a novel biomaterial for craniofacial skeletal yissue engineering and reconstruction. J Biomed Mater Res. 1998; 43(4):428-32.
8. Chim H, Gosain A K. Biomaterials in craniofacial surgery experimental studies and clinical application J Craniofac Surg. 2009; 20:29-33.

9. Gasparini G, Boniello R, Moro A, Tamburrini G, Di Rocco C, Pelo S. Cranial reshaping using methyl methacrylate:technical note. J Craniofac Surg. 2009; 20:184-90.
10. Moreira-Gonzalez A, Jackson I T, Miyawaki T, Barakat K, DiNick V. Clinical outcome in cranioplasty: critical review in long-term follow-up. J Craniofac Surg. 2003; 14:144-53.
11. Cammisa F P, Jr., Lowery G, Garfin S R, Geisler F H, Klara P M, McGuire R A, et al. Two-year fusion rate equivalency between Grafton DBM gel and autograft in posterolateral spine fusion: a prospective controlled trial employing a side-by-side comparison in the same patient. Spine (Phila Pa. 1976). 2004 Mar. 15; 29(6):660-6.
12. Chan C, Thompson I, Robinson P, Wilson J, Hench L. Evaluation of Bioglass/dextran composite as a bone graft substitute. Int J Oral Maxillofac Surg. 2002 February; 31(1):73-7.
13. Chazono M, Tanaka T, Komaki H, Fujii K. Bone formation and bioresorption after implantation of injectable beta-tricalcium phosphate granules-hyaluronate complex in rabbit bone defects. J Biomed Mater Res A. 2004 Sep. 15; 70(4):542-9.
14. Urban R M, Turner T M, Hall D J, Inoue N, Gitelis S. Increased bone formation using calcium sulfate-calcium phosphate composite graft. Clin Orthop Relat Res. 2007 June; 459:110-7.
15. Gitelis S, Urban R M, Turner T M, Heck R, Parameswaran A D, editors. Outcomes in the Treatment of Benign Bone Lesions Using an Engineering Ceramic: Preclinical and Clinical Results. Materials and Processes for Medical Devices Conference; 2009 Aug. 10-12, 2009; Minneapolis, Minn.
16. Ikenaga M, Hardouin P, Lemaitre J, Andrianjatovo H, Flautre B. Biomechanical characterization of a biodegradable calcium phosphate hydraulic cement: a comparison with porous biphasic calcium phosphate ceramics. J Biomed Mater Res. 1998 April; 40(1):139-44.
17. Urban R M, Turner T M, Hall D J, Infanger S, Cheema N, Lim T H. Healing of large defects treated with calcium sulfate pellets containing demineralized bone matrix particles. Orthopedics. 2003 May; 26(5 Suppl):s581-5.
18. Greish Y E, Brown P W. Phase evolution during the formation of stoichiometric hydroxyapatite at 37.4 degrees C. J Biomed Mater Res B Appl Biomater. 2003 Oct. 15; 67(1):632-7.
19. Wagoner Johnson A J, Herschler B A. A review of the mechanical behavior of CaP and CaP/polymer composites for applications in bone replacement and repair. Acta Biomater. 2011 January; 7(1):16-30.
20. Dumas J E, Davis T E, Yoshii T, Nyman J, Holt G E, Perrien D S, et al. Synthesis of Allograft Bone/Polymer Composites and Evaluation of Remodeling in a Rabbit Femoral Condyle Model. Acta Biomaterialia. 2010; 6:2394-406.
21. Otsu N. A threshold selection method for gray level histogram. IEEE Trans Syst Man Cybern. 1978; SMC-9 (1)(62-66).
1. Khan, Y., et al., *Tissue engineering of bone: Material and matrix considerations*. Journal of Bone and Joint Surgery-American Volume, 2008. 90A: p. 36-42.
2. Legeros, R. Z., A. Chohayeb, and A. Schulman, *APATITIC CALCIUM PHOSPHATES POSSIBLE DENTAL RESTORATIVE MATERIALS*. Journal of Dental Research, 1982. 61(SPEC. ISSUE): p. 343.
3. Chim, H. and A. K. Gosain, *Biomaterials in Craniofacial Surgery Experimental Studies and Clinical Application*. Journal of Craniofacial Surgery, 2009. 20(1): p. 29-33.
4. Moreira-Gonzalez, A., et al., *Clinical outcome in cranioplasty: Critical review in long-term follow-up*. Journal of Craniofacial Surgery, 2003. 14(2): p. 144-153.
5. Friedman, C. D., et al., *BoneSource™ hydroxyapatite cement: A novel biomaterial for craniofacial skeletal tissue engineering and reconstruction*. Journal of Biomedical Materials Research, 1998. 43(4): p. 428-432.
6. Gasparini, G., et al., *Cranial Reshaping Using Methyl Methacrylate: Technical Note*. Journal of Craniofacial Surgery, 2009. 20(1): p. 184-190.
7. Bohner, M., *Designing ceramics for injectable bone graft substitutes*, in *Injectable Biomaterials: Science and Applications*, B. L. Vernon, Editor. 2011, Woodhead Publishing: Philadelphia.
8. Wagoner Johnson, A. J. and B. A. Herschler, *A review of the mechanical behavior of CaP and CaP/polymer composites for applications in bone replacement and repair*. Acta Biomaterialia, 2011. 7(1): p. 16-30.
9. Chan, C., et al., *Evaluation of Bioglass/dextran composite as a bone graft substitute*. International Journal of Oral and Maxillofacial Surgery, 2002. 31(1): p. 73-77.
10. Chazono, M., et al., *Bone formation and bioresorption after implantation of injectable beta-tricalcium phosphate granules-hyaluronate complex in rabbit bone defect*. Journal of Biomedical Materials Research Part A, 2004. 70A(4): p. 542-549.
11. Schwartz, Z., et al., *Clinical evaluation of demineralized bone allograft in a hyaluronic acid carrier for sinus lift augmentation in humans: a computed tomography and histomorphometric study*. Clinical Oral Implants Research, 2007. 18(2): p. 204-211.
12. Cammisa, F. P., et al., *Two-year fusion rate equivalency between Grafton (R) DBM gel and autograft in posterolateral spine fusion*. Spine, 2004. 29(6): p. 660-666.
13. Dumas, J. E., et al., *Synthesis, characterization, and remodeling of weight-bearing allograft bone/polyurethane composites in the rabbit*. Acta Biomaterialia, 2010. 6(7): p. 2394-2406.
14. Bennett, S., et al., *Initial biocompatibility studies of a novel degradable polymeric bone substitute that hardens in situ*. Bone, 1996. 19(1): p. S101-S107.
15. Bonzani, I. C., et al., *Synthesis of two-component injectable polyurethanes for bone tissue engineering*. Biomaterials, 2007. 28(3): p. 423-433.
16. Ertel, S. I., et al., *IN-VITRO STUDY OF THE INTRINSIC TOXICITY OF SYNTHETIC SURFACES TO CELLS*. Journal of Biomedical Materials Research, 1994. 28(6): p. 667-675.
17. Pons, F., et al., *Effect of toluene diisocyanate and its corresponding amines on viability and growth of human lung fibroblasts in culture*. Cell Biology and Toxicology, 1999. 15(5): p. 333-340.
18. Mishra, P. K., et al., *Isocyanates induces DNA damage, apoptosis, oxidative stress, and inflammation in cultured human lymphocytes*. Journal of Biochemical and Molecular Toxicology, 2008. 22(6): p. 429-440.
19. Dumas, J. E., et al., *Synthesis and Characterization of an Injectable Allograft Bone/Polymer Composite Bone Void Filler with Tunable Mechanical Properties*. Tissue Engineering Part A, 2010. 16(8): p. 2505-2518.

20. Hinrichsen, G., *Polyurethane handbook (2nd ed.)*. Edited by G. Oertel, Hanser Publishers, Munich 1993, 770 pp., DM 358, ISBN 3-446-17198-3. Acta Polymerica, 1994. 45(5): p. 398-398.

21. Hafeman, A., et al., *Injectable biodegradable polyurethane scaffolds with release of platelet-derived growth factor for tissue repair and regeneration*. Pharm Res, 2008. 25(10): p. 2387-99.

22. Hoven, V. P., et al., *Surface-charged chitosan: Preparation and protein adsorption*. Carbohydrate Polymers, 2007. 68(1): p. 44-53.

23. GluckHirsch, J. B. and J. L. Kokini, *Determination of the molecular weight between crosslinks of waxy maize starches using the theory of rubber elasticity*. Journal of Rheology, 1997. 41(1): p. 129-139.

24. Bagley, E. B., *The seperation of elastic and visous effects in polymer flow*. Transactions of the Society of Rheology, 1961: p. 355-368.

25. Guan, J. J., et al., *Biodegradable poly(ether ester urethane)urea elastomers based on poly(ether ester) triblock copolymers and putrescine: synthesis, characterization and cytocompatibility*. Biomaterials, 2004. 25(1): p. 85-96.

26. Ortel, G., *Polyurethane Handbook*. 1994: Hanser Gardner Publications.

27. Guelcher, S. A., et al., *Synthesis and in vitro biocompatibility of injectable polyurethane foam scaffolds*. Tissue Engineering, 2006. 12(5): p. 1247-1259.

28. Adolph, E. J., et al., *Injectable biodegradable polyurethane scaffolds for wound healing*. Submitted, 2011.

29. Adhikari, R., et al., *Biodegradable injectable polyurethanes: synthesis and evaluation for orthopaedic applications*. Biomaterials, 2008. 29(28): p. 3762-70.

30. Dumas, J. E., et al., *Synthesis and Characterization of an Injectable Allograft Bone/polymer Composite Bone Void Filler with Tunable Mechanical Properties*. Tissue Eng Part A, 2010. 16(8): p. 2505-18.

31. Bennett, S., et al., *Initial biocompatibility studies of a novel degradable polymeric bone substitute that hardens in situ*. Bone, 1996. 19(1, Supplement): p. 101S-107S.

32. Buckley, M. J. and E. J. Beckman, *Adhesive Use in Oral and Maxillofacial Surgery*. Oral and Maxillofacial Surgery Clinics of North America, 2010. 22(1): p. 195-199.

33. Zhang, J.-Y., et al., *A new peptide-based urethane polymer: synthesis, biodegradation, and potential to support cell growth in vitro*. Biomaterials, 2000. 21: p. 1247-1258.

34. Hafeman, A. E., et al., *Characterization of the degradation mechanisms of lysine-derived aliphatic poly(ester urethane) scaffolds*. Biomaterials, 2011. 32(2): p. 419-29.

35. Elliott, S. L., et al., *Identification of biodegradation products formed by L-phenylalanine based segmented polyurethaneureas*. Journal of Biomaterials Science Polymer Edition, 2002. 13(6): p. 691-711.

36. Bonzani, I. C., et al., *Synthesis of two-component injectable polyurethanes for bone tissue engineering*. Biomaterials, 2007. 28: p. 423-433.

37. Adhikari, R., et al., *Biodegradable injectable polyurethanes: Synthesis and evaluation for orthopaedic applications*. Biomaterials, 2008. 29(28): p. 3762-3770.

38. Steven, F. S. J., D. S., *Purification and amino acid composition of monomeric and polymeric collagens*. Biochem. J., 1967. 104: p. 534-536.

39. Lu, Q.-W., T. R. Hoye, and C. W. Macosko, *Reactivity of common functional groups with urethanes: Models for reactive compatibilization of thermoplastic polyurethane blends*. Journal of Polymer Science Part A: Polymer Chemistry, 2002. 40(14): p. 2310-2328.

40. Szycher, M., *Szycher's Handbook of Polyurethanes*. 1999, Boca Raton: CRC Press LLC.

41. Kar, A., *Pharmaceutical Drug Analysis*. 2nd ed. 2005, Daryaganj, New Delhi: New Age International Limited.

42. Zhang, J. Y., et al., *A new peptide-based urethane polymer: synthesis, biodegradation, and potential to support cell growth in vitro*. Biomaterials, 2000. 21(12): p. 1247-1258.

43. Fogler, H. S., *Elements of Chemical Reaction Engineering*. 4th Ed. ed. 1999, Upper Saddle River, N.J.: Pearson Education.

44. Sivak, W. N., et al., *Catalyst-dependent drug loading of LDI-glycerol polyurethane foams leads to differing controlled release profiles*. Acta Biomaterialia, 2008. 4(5): p. 1263-1274.

45. Silva, A. L. and J. C. Bordado, *Recent developments in polyurethane catalysis: Catalytic mechanisms review*. Catalysis Reviews-Science and Engineering, 2004. 46(1): p. 31-51.

46. Semsarzadeh, M. A. and A. H. Navarchian, *Effects of NCO/OH ratio and catalyst concentration on structure, thermal stability, and crosslink density of poly(urethane-isocyanurate)*. Journal of Applied Polymer Science, 2003. 90(4): p. 963-972.

47. Gorna, K. and S. Gogolewski, *Preparation, degradation, and calcification of biodegradable polyurethane foams for bone graft substitutes*. Journal of Biomedical Materials Research Part A, 2003. 67A(3): p. 813-827.

48. Storey, R. F., J. S. Wiggins, and A. D. Puckett, *Hydrolyzable poly(ester-urethane) networks from L-lysine diisocyanate and D,L-lactide/c-caprolactone homo-and copolyester triols*. Journal of Polymer Science Part A: Polymer Chemistry, 1994. 32(12): p. 2345-2363.

49. Wang, Z., et al., *Preparation and rapid degradation of nontoxic biodegradable polyurethanes based on poly(lactic acid)-poly(ethylene glycol)-poly(lactic acid) and l-lysine diisocyanate*. Polymer Chemistry, 2011. 2(3): p. 601-607.

50. Caracciolo, P., F. Buffa, and G. Abraham, *Effect of the hard segment chemistry and structure on the thermal and mechanical properties of novel biomedical segmented poly(esterurethanes)*. Journal of Materials Science: Materials in Medicine, 2009. 20(1): p. 145-155.

51. Guan, J., et al., *Biodegradable poly(ether ester urethane) urea elastomers based on poly(ether ester) triblock copolymers and putrescine: synthesis, characterization and cytocompatibility*. Biomaterials, 2004. 25(1): p. 85-96.

52. Hafeman, A., et al., *Injectable Biodegradable Polyurethane Scaffolds with Release of Platelet-derived Growth Factor for Tissue Repair and Regeneration*. Pharmaceutical Research, 2008. 25(10): p. 2387-2399.

53. Kretlow, J. D., et al., *Injectable Biomaterials for Regenerating Complex Craniofacial Tissues*. Advanced Materials, 2009. 21(32-33): p. 3368-3393.

54. Timmer, M. D., et al., *In vitro cytotoxicity of injectable and biodegradable poly(propylene fumarate)-based networks: Unreacted macromers, cross-linked networks, and degradation products*. Biomacromolecules, 2003. 4(4): p. 1026-1033.

55. Dumas, J. E., et al., *Synthesis of Allograft Bone/Polymer Composites and Evaluation of Remodeling in a Rabbit Femoral Condyle Model*. Acta Biomaterialia, 2010. 6: p. 2394-2406.
1. Li, B., et al., *Biomaterials,* 2009, 30(35), 6768-6779.
2. Belfrage, O., et al., *Acta Orthopaedica,* 2011, 82(2), 228-233.
3. Bashoor-Zedah, M., Baroud, G. and Bohner, M., *Biomaterials,* 2011, 32(27), 6362-6373.
1 D. Simpson, J. F. Keating, *Injury,* 2004, 35, 913.
2 J. Dumas, T. Davis, G. Holt, T. Yoshii, D. Perrien, J. Nyman, T. Boyce, S. Guelcher, *Acta Biomaterialia,* 2010, 6, 2394.
3 J. Blaker, A. Boccaccini, *Expert review of medical devices,* 2005, 2, 303.
4 E. Verne, C. Vitale-Brovarone, E. Bui, C. Bianchi, A. Boccaccini, *Journal of Biomedical Materials Research,* 2008, 90, 981.
5 C. Kunze, T. Freier, E. Helwig, B. Sandner, D. Reif, A. Wutzler, H. Radusch, *Biomaterials,* 2003, 24, 967.
6 Q. Chen, R. Rezwan, D. Armitage, S. Nazhat, A. Boccaccini, *J Mater Sci: Mater Med,* 2006, 17, 979.
7 G. Jiang, I. Jones, C. Rudd, G. Walker, *Journal of Applied Polymer Science,* 2009, 114, 658.
8 T. Kokubo, H. Takadama, *Biomaterials,* 2006, 27, 2907.
1. Russell T A, Leighton R K. Comparison of Autogenous Bone Graft and Endothermic Calcium Phosphate Cement for Defect Augmentation in Tibial Plateau Fractures. Journal of Bone and Joint Surgery-American Volume. 2008; 90A(10):2057-61.
2. Simpson D, Keating J F. Outcome of tibial plateau fractures managed with calcium phosphate cement. Injury-International Journal of the Care of the Injured. 2004; 35(9):913-8.
3. Amendola L, Gasbarrini A, Fosco M, Simoes C E, Terzi S, Delure F, et al. Fenestrated pedicle screws for cement-augmented purchase in patients with bone softening: a review of 21 cases. J Orthop Traumatol. 2011; 12(4):193-9.
4. Larsson S, Stadelmann V A, Arnoldi J, Behrens M, Hess B, Procter P, et al. Injectable calcium phosphate cement for augmentation around cancellous bone screws. In vivo biomechanical studies. Journal of Biomechanics. 2012; 45(7):1156-60.
5. Larsson S, Procter P. Optimising implant anchorage (augmentation) during fixation of osteoporotic fractures: Is there a role for bone-graft substitutes? Injury-International Journal of the Care of the Injured. 2011; 42:S72-S6.
6. Verlaan J J, Oner F C, Dhert W J A. Anterior spinal column augmentation with injectable bone cements. Biomaterials. 2006; 27(3):290-301.
7. Legeros R Z, Chohayeb A, Schulman A. Apatitic Calcium Phosphates Possible Dental Restorative Materials. Journal of Dental Research. 1982; 61(SPEC. ISSUE):343.
8. Chim H, Gosain A K. Biomaterials in Craniofacial Surgery Experimental Studies and Clinical Application. J Craniofac Surg. 2009; 20(1):29-33.
9. Hall J A, Beuerlein M J, McKee M D. Open reduction and internal fixation compared with circular fixator application for bicondylar tibial plateau fractures. Surgical technique. J Bone Joint Surg Am. 2009; 91 Suppl 2 Pt 1:74-88. Epub 2009/03/11.
10. Wagoner Johnson A J, Herschler B A. A review of the mechanical behavior of CaP and CaP/polymer composites for applications in bone replacement and repair. Acta Biomater. 2011; 7(1):16-30. Epub 2010/07/27.
11. Bohner M. Design of ceramic-based cements and putties for bone graft substitution. Eur Cell Mater. 2010; 20:1-12. Epub 2010/06/25.
12. Dumas J E, Davis T, Holt G E, Yoshii T, Perrien D S, Nyman J S, et al. Synthesis, characterization, and remodeling of weight-bearing allograft bone/polyurethane composites in the rabbit. Acta Biomaterialia. 2010; 6(7):2394-406.
13. Boccaccini A R, Blaker J J. Bioactive composite materials for tissue engineering scaffolds. Expert Review of Medical Devices. 2005; 2(3):303-17.
14. Hench L L, Wilson J. Bioceramics. Mrs Bulletin. 1991; 16(9):62-74.
15. Saravanapavan P, Jones J R, Pryce R S, Hench L L. Bioactivity of gel-glass powders in the CaO—SiO2 system: A comparison with ternary (CaO—P2O5-SiO2) and quaternary glasses (SiO2—CaO—P2O5-Na2O). J Biomed Mater Res Part A. 2003; 66A(1):110-9.
16. Hench L L. The story of Bioglass (R). J Mater Sci-Mater Med. 2006; 17(11):967-78.
17. Hoppe A, Gueldal N S, Boccaccini A R. A review of the biological response to ionic dissolution products from bioactive glasses and glass-ceramics. Biomaterials. 2011; 32(11):2757-74.
18. Tanner K E. Bioactive composites for bone tissue engineering. Proceedings of the Institution of Mechanical Engineers Part H-Journal of Engineering in Medicine. 2010; 224(H12): 1359-72.
19. Bretcanu O, Misra S, Roy I, Renghini C, Fiori F, Boccaccini A R, et al. In vitro biocompatibility of 45S5 Bioglass (R)-derived glass-ceramic scaffolds coated with poly(3-hydroxybutyrate). Journal of Tissue Engineering and Regenerative Medicine. 2009; 3(2):139-48.
20. Bil M, Ryszkowska J, Roether J A, Bretcanu O, Boccaccini A R. Bioactivity of polyurethane-based scaffolds coated with Bioglass((R)). Biomedical Materials. 2007; 2(2):93-101.
21. Ryszkowska J L, Auguscik M, Sheikh A, Boccaccini A R. Biodegradable polyurethane composite scaffolds containing Bioglass (R) for bone tissue engineering. Composites Science and Technology. 2010; 70(13):1894-908.
22. Chan C, Thompson I, Robinson P, Wilson J, Hench L. Evaluation of Bioglass/dextran composite as a bone graft substitute. International Journal of Oral and Maxillofacial Surgery. 2002; 31(1):73-7.
23. Neuendorf R E, Saiz E, Tomsia A P, Ritchie R O. Adhesion between biodegradable polymers and hydroxyapatite: Relevance to synthetic bone-like materials and tissue engineering scaffolds. Acta Biomaterialia. 2008; 4(5):1288-96.
24. Chen Q Z, Rezwan K, Armitage D, Nazhat S N, Boccaccini A R. The surface functionalization of 45S5 Bioglass (R)-based glass-ceramic scaffolds and its impact on bioactivity. J Mater Sci-Mater Med. 2006; 17(11):979-87.
25. Chen Q-Z, Rezwan K, Francon V, Armitage D, Nazhat S N, Jones F H, et al. Surface functionalization of Bioglass((R))-derived porous scaffolds. Acta Biomaterialia. 2007; 3(4):551-62.
26. Verne E, Vitale-Brovarone C, Bui E, Bianchi C L, Boccaccini A R. Surface functionalization of bioactive glasses. J Biomed Mater Res Part A. 2009; 90A(4):981-92.
27. Kunze C, Freier T, Helwig E, Sandner B, Reif D, Wutzler A, et al. Surface modification of tricalcium phosphate for improvement of the interfacial compatibility with biodegradable polymers. Biomaterials. 2003; 24(6):967-74.

28. Jiang G, Walker G S, Jones I A, Rudd C D. XPS identification of surface-initiated polymerisation during monomer transfer moulding of poly(epsilon-caprolactone)/Bioglass (R) fibre composite. Appl Surf Sci. 2005; 252(5):1854-62.
29. Jiang G, Evans M E, Jones I A, Rudd C D, Scotchford C A, Walker G S. Preparation of poly(epsilon-caprolactone)/continuous bioglass fibre composite using monomer transfer moulding for bone implant. Biomaterials. 2005; 26(15):2281-8.
30. Barsbay M, Gueven G, Stenzel M H, Davis T P, Barner-Kowollik C, Barner L. Verification of controlled grafting of styrene from cellulose via radiation-induced RAFT polymerization. Macromolecules. 2007; 40(20): 7140-7.
31. Kokubo T, Takadama H. How useful is SBF in predicting in vivo bone bioactivity? Biomaterials. 2006; 27(15): 2907-15.
32. Guelcher S A, Patel V, Gallagher K M, Connolly S, Didier J E, Doctor J S, et al. Synthesis and in vitro biocompatibility of injectable polyurethane foam scaffolds. Tissue Engineering. 2006; 12(5):1247-59.
33. Dumas J E, Zienkiewicz K, Tanner S A, Prieto E M, Bhattacharyya S, Guelcher S A. Synthesis and Characterization of an Injectable Allograft Bone/Polymer Composite Bone Void Filler with Tunable Mechanical Properties. Tissue Engineering Part A. 2010; 16(8):2505-18.
34. Garnier K B, Dumas R, Rumelhart C, Arlot M E. Mechanical characterization in shear of human femoral cancellous bone: torsion and shear tests. Medical Engineering & Physics. 1999; 21(9):641-9.
35. Ford C M, Keaveny T M. The dependence of shear failure properties of trabecular bone on apparent density and trabecular orientation. Journal of Biomechanics. 1996; 29(10):1309-17.
36. Penczek S, Duda A, Kowalski A, Libiszowski J, Majerska K, Biela T. On the mechanism of polymerization of cyclic esters induced by Tin(II) octoate. Macromolecular Symposia. 2000; 157:61-70.
37. Heiney P A, Gruneberg K, Fang J Y, Dulcey C, Shashidhar R. Structure and growth of chromophore-functionalized (3-aminopropyl)triethoxysilane self-assembled on silicon. Langmuir. 2000; 16(6):2651-7.
38. Yoon K R, Lee K B, Chi Y S, Yun W S, Joo S W, Choi I S. Surface-initiated, enzymatic polymerization of biodegradable polyesters. Advanced Materials. 2003; 15(24): 2063-+.
39. Wang X, Yang J, Zhou J. Crystallization behavior of poly(epsilon-caprolactone) grafted on silicon surface. E-Polymers. 2011.
40. Olivier A, Raquez J-M, Dubois P, Damman P. Semicrystalline poly(epsilon-caprolactone) brushes on gold substrate via "grafting from" method New insights with AFM characterization. European Polymer Journal. 2011; 47(1):31-9.
41. Adamson A W, Gast A P. Physical Chemistry of Surfaces. New York: Wiley; 1997.
42. Saeri M R, Afshar A, Ghorbani M, Ehsani N, Sorrell C C. The wet precipitation process of hydroxyapatite. Materials Letters. 2003; 57(24-25):4064-9.
43. Wang Z, Lu B, Chen L, Chang J. Evaluation of an osteostimulative putty in the sheep spine. J Mater Sci-Mater Med. 2011; 22(1):185-91.
44. Nazarian A, Meier D, Mueller R, Snyder B D. Functional Dependence of Cancellous Bone Shear Properties on Trabecular Microstructure Evaluated Using Time-Lapsed Micro-Computed Tomographic Imaging and Torsion Testing. Journal of Orthopaedic Research. 2009; 27(12): 1667-74.
45. Yoshii T, Dumas J E, Okawa A, Spengler D M, Guelcher S A. Synthesis, characterization of calcium phosphates/polyurethane composites for weight-bearing implants. Journal of Biomedical Materials Research Part B-Applied Biomaterials. 2012; 100B(1):32-40.
46. Mosse W K J, Koppens M L, Gengenbach T R, Scanlon D B, Gras S L, Ducker W A. Peptides Grafted from Solids for the Control of Interfacial Properties. Langmuir. 2009; 25(3):1488-94.
47. Allen M R, Hogan H A, Hobbs W A, Koivuniemi A S, Koivuniemi M C, Burr D B. Raloxifene enhances material-level mechanical properties of femoral cortical and trabecular bone. Endocrinology. 2007; 148(8):3908-13.
48. Libicher M, Hillmeier J, Liegibel U, Sommer U, Pyerin W, Vetter M, et al. Osseous integration of calcium phosphate in osteoporotic vertebral fractures after kyphoplasty: initial results from a clinical and experimental pilot study. Osteoporos Int. 2006; 17(8):1208-15. Epub 2006/06/13.
49. Maestretti G, Cremer C, Otten P, Jakob R P. Prospective study of standalone balloon kyphoplasty with calcium phosphate cement augmentation in traumatic fractures. Eur Spine J. 2007; 16(5):601-10. Epub 2006/11/23.
50. Ryszkowska J, Bil M, Wozniak P, Lewandowska-Szumiel M, Kurzydlowski K J. Influence of catalyst type on biocompatibility of polyurethanes. Advanced Materials Forum Iii, Pts 1 and 22006. p. 887-91.
51. Page J M, Prieto E M, Dumas J E, Zienkiewicz K J, Wenke J C, Brown-Baer P, et al. Biocompatibility and chemical reaction kinetics of injectable, settable polyurethane/allograft bone biocomposites. Acta Biomaterialia. 2012; 8(12):4405-16.
52. Pisanova E, Mader E. Acid-base interactions and covalent bonding at a fiber-matrix interface: contribution to the work of adhesion and measured adhesion strength. Journal of Adhesion Science and Technology. 2000; 14(3): 415-36.
53. Mangipudi V, Tirrell M, Pocius A V. Direct Measurement of Molecular-Level Adhesion between Poly(Ethylene-Terephthalate) and Polyethylene Films—Determination of Surface and Interfacial Energies. Journal of Adhesion Science and Technology. 1994; 8(11):1251-70.
54. Mader E. Study of fibre surface treatments for control of interphase properties in composites. Composites Science and Technology. 1997; 57(8):1077-88.
55. Ruppender N S, Merkel A R, Martin T J, Mundy G R, Sterling J A, Guelcher S A. Matrix Rigidity Induces Osteolytic Gene Expression of Metastatic Breast Cancer Cells. Plos One. 2010; 5(11).
56. Brown H R, Russell T P. Entanglements at polymer surfaces and interfaces. Macromolecules. 1996; 29(2): 798-800.
57. Gurarslan A, Shen J, Tonelli A E. Behavior of Poly (epsilon-caprolactone)s (PCLs) Coalesced from Their Stoichiometric Urea Inclusion Compounds and Their Use as Nucleants for Crystallizing PCL Melts: Dependence on PCL Molecular Weights. Macromolecules. 2012; 45(6): 2835-40.
58. Lu Q W, Hoye T R, Macosko C W. Reactivity of common functional groups with urethanes: Models for reactive compatibilization of thermoplastic polyurethane blends. Journal of Polymer Science Part a-Polymer Chemistry. 2002; 40(14):2310-28.

59. Flexible Polyurethane Foams. 2nd ed. Midland, Mich.: The Dow Chemical Company; 1997.

What is claimed is:

1. A composite, comprising:
a NCO-terminated prepolymer comprising a polyisocyanate that includes about 10 wt % to about 55 wt % NCO and a first polyol that includes a molecular weight of about 100 g/mol to about 1000 g/mol;
a second polyol; and
a bioceramic material;
wherein said composite is biodegradable.

2. The composite of claim 1, further comprising a bioactive agent.

3. The composite of claim 2, wherein the bioactive agent is at least one of an antiviral agent, antimicrobial agent, antibiotic agent, amino acid, peptide, protein, glycoprotein, lipoprotein, antibody, steroidal compound, antibiotic, antimycotic, cytokine, vitamin, carbohydrate, lipid, extracellular matrix, extracellular matrix component, chemotherapeutic agent, cytotoxic agent, growth factor, anti-rejection agent, analgesic, anti-inflammatory agent, viral vector, protein synthesis co-factor, hormone, endocrine tissue, synthesizer, enzyme, polymer-cell scaffolding agent with parenchymal cells, angiogenic drug, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, and penetraction enhancer; and combinations thereof.

4. The composite of claim 3, wherein the growth factor is recombinant human bone morphogenetic growth factor-2 (rhBMP-2).

5. The composite of claim 3, wherein the composite comprises about 50 to about 400 μg/mL of the growth factor.

6. The composite of claim 1, wherein the bioceramic material comprises β-tricalcium phosphate and derivatives thereof.

7. The composite of claim 6, wherein the bioceramic material is surface-modified.

8. The composite of claim 6, wherein the bioceramic material is surface-modified with polycaprolactone, 3-aminopropyl-triethoxysilane, or a combination thereof.

9. The composite of claim 1, wherein the composite has a porosity of about 0% to about 80%.

10. The composite of claim 1, wherein the composite comprises about 30 wt % to about 90 wt % bioceramic material.

11. The composite of claim 1, wherein the bioceramic material comprises particles that range from about 1 μm to about 500 μm in diameter.

12. The composite of claim 1, wherein the polyurethanes are degraded within approximately 4 weeks to approximately 12 months.

13. The composite of claim 1, further comprising a catalyst.

14. The composite of claim 13, wherein the catalyst comprises a tertiary amine.

15. The composite of claim 14, wherein the catalyst is selected from the group consisting of bis(2-demethylaminoethyl)ether (DMAEE), triethylene diamine (TEDA), Tegoamin33, stannous octoate, dibutyltin dilaurate, and Coscat organometallic catalysts manufactured by Vertullus (a bismuth based catalyst).

16. A method of preparing a composite, comprising:
providing a composition that comprises a second polyol, a catalyst and water;
contacting the composition with a NCO-terminated prepolymer comprising a polyisocyanate that includes about 10 wt % to about 55 wt % NCO and a first polyol that includes a molecular weight of about 100 g/mol to about 1000 g/mol;
adding at least 30 wt % of a bioceramic material to the composition;
wherein said composite is biodegradable.

17. The method of claim 16, wherein the bioceramic material comprises β-tricalcium phosphate and derivatives thereof.

18. The method of claim 16, further comprising:
contacting the bioceramic material with a modifying substance to surface modify the bioceramic material.

19. The method of claim 18, wherein the modifying substance is polycaprolactone, 3-aminopropyl-triethoxysilane, or a combination thereof.

20. The method of claim 16, further comprising:
adding a bioactive agent to the composition, wherein the bioactive agent is at least one of an antiviral agent, antimicrobial agent, antibiotic agent, amino acid, peptide, protein, glycoprotein, lipoprotein, antibody, steroidal compound, antibiotic, antimycotic, cytokine, vitamin, carbohydrate, lipid, extracellular matrix, extracellular matrix component, chemotherapeutic agent, cytotoxic agent, growth factor, anti-rejection agent, analgesic, anti-inflammatory agent, viral vector, protein synthesis co-factor, hormone, endocrine tissue, synthesizer, enzyme, polymer-cell scaffolding agent with parenchymal cells, angiogenic drug, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, and penetraction enhancer; and combinations thereof.

21. The method of claim 20, wherein the growth factor is recombinant human bone morphogenetic growth factor-2 (rhBMP-2).

22. A method of treating a bone condition of a subject, comprising:
administering to a bone site a biodegradable composite including a NCO-terminated prepolymer comprising a polyisocyanate that includes about 10 wt % to about 55 wt % NCO and a first polyol that includes a molecular weight of about 100 g/mol to about 1000 g/mol, a second polyol, and a bioceramic material.

23. The method of claim 22, wherein the bioceramic material comprises β-tricalcium phosphate and derivatives thereof.

24. The method of claim 23, wherein the bioceramic material is surface-modified.

25. The method of claim 24, wherein the bioceramic material surface-modified with polycaprolactone, 3-aminopropyl-triethoxysilane, or a combination thereof.

26. The method of claim 22, wherein the composite further comprises a bioactive agent that is at least one of an antiviral agent, antimicrobial agent, antibiotic agent, amino acid, peptide, protein, glycoprotein, lipoprotein, antibody, steroidal compound, antibiotic, antimycotic, cytokine, vitamin, carbohydrate, lipid, extracellular matrix, extracellular matrix component, chemotherapeutic agent, cytotoxic agent, growth factor, anti-rejection agent, analgesic, anti-inflammatory agent, viral vector, protein synthesis co-factor, hormone, endocrine tissue, synthesizer, enzyme, polymer-cell scaffolding agent with parenchymal cells, angiogenic drug, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, and penetraction enhancer; and combinations thereof.

27. The method of claim 23, wherein the growth factor is recombinant human bone morphogenetic growth factor-2 (rhBMP-2).

28. The method of claim 22, wherein the step of administering includes injecting the composite on to a bone site and allowing the composite to cure on the bone site.

29. The method of claim 22, wherein the step of administering includes molding the composite and then placing the molded composite on to the bone site.

30. The method of claim 24, wherein the bone site is a site on a ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bone, metacarpal bone, phalange, ilium, ischium, pubis, femur, tibia, fibula, patella, calcaneus, tarsal, or metatarsal bone.

31. The method of claim 22, wherein the bone condition is a simple fracture, a compound fracture, a non-union, a spinal injury, scoliosis, lordosis, or kyphosis.

32. The method of claim 22, wherein the method comprises joint reconstruction, arthrodesis, arthroplasty or cup arthroplasty of the hip, femoral or humeral head replacement, femoral head surface replacement or total joint replacement, repair of the vertebral column, spinal fusion, internal vertebral fixation, tumor surgery, deficit filling, discectomy, laminectomy, excision of a spinal tumor, anterior cervical or thoracic operation, intermaxillary fixation of a fracture, mentoplasty, temporomandibular joint replacement, alveolar ridge augmentation and reconstruction, sinus lift, a cosmetic procedure, revision surgery, or revision surgery of a total joint arthroplasty.

* * * * *